United States Patent [19]

Mitsuhashi

[11] Patent Number: 5,580,971

[45] Date of Patent: Dec. 3, 1996

[54] FUNGAL DETECTION SYSTEM BASED ON RRNA PROBES

[75] Inventor: Masato Mitsuhashi, Irvine, Calif.

[73] Assignees: Hitachi Chemical Company, Ltd., Tokyo, Japan; Hitachi Chemical Research Center, Inc., Irvine, Calif.

[21] Appl. No.: 379,081

[22] Filed: Jan. 26, 1995

Related U.S. Application Data

[63] Continuation of Ser. No. 922,522, Jul. 28, 1992, abandoned.

[51] Int. Cl.$^6$ ..................................................... C07H 21/04
[52] U.S. Cl. ........................ 536/24.32; 435/6; 536/24.33
[58] Field of Search .............................. 536/24.32, 24.3, 536/24.33; 435/6

[56] References Cited

U.S. PATENT DOCUMENTS

| | | | |
|---|---|---|---|
| 4,729,950 | 3/1988 | Kricka et al. | 435/28 |
| 4,734,363 | 3/1988 | Dattagupta et al. | 435/91.1 |
| 4,751,177 | 6/1988 | Stabinsky | 435/6 |
| 4,797,355 | 1/1989 | Stabinsky | 435/6 |
| 4,851,330 | 7/1989 | Kohne | 435/6 |
| 4,894,325 | 1/1990 | Englehardt et al. | 435/6 |
| 5,082,935 | 1/1992 | Cruickshank | 536/24.3 |
| 5,084,565 | 1/1992 | Parodos et al. | 536/24.32 |

FOREIGN PATENT DOCUMENTS

| | | |
|---|---|---|
| 0130515 | 6/1984 | European Pat. Off. . |
| 0152886 | 8/1985 | European Pat. Off. . |
| 0327390 | 2/1989 | European Pat. Off. . |
| 0329822 | 8/1989 | European Pat. Off. . |
| 0335633 | 10/1989 | European Pat. Off. .......... C12Q 1/68 |
| 0369775 | 11/1989 | European Pat. Off. . |
| 0370694 | 11/1989 | European Pat. Off. . |
| 9006042 | 6/1990 | European Pat. Off. . |
| 9006045 | 6/1990 | European Pat. Off. . |
| 0422872 | 10/1990 | European Pat. Off. . |
| 0469610 | 8/1991 | European Pat. Off. . |
| 2187283 | 9/1987 | United Kingdom . |
| 8603782 | 7/1986 | WIPO . |
| 8801302 | 2/1988 | WIPO . |
| 8803957 | 6/1988 | WIPO .............................. C12Q 1/68 |
| 9006044 | 6/1990 | WIPO . |
| 9102092 | 2/1991 | WIPO . |

OTHER PUBLICATIONS

Betzl et al., *App. Environ. Microbiol.* 56(9), 2927–2929 (1990).
Baldwin et al., *Science* 245, 1104–1107 (1989).
Martin et al., *Mol. Gen. Genet.* 208, 177–184 (1987).
C. B. Harley, "Hybridization of Oligo(dT) to RNA on Nitrocellulose", Gene Analysis Techniques, vol. 4, 1987, pp. 17–22.
A. Palva et al., "Laboratory Methods: Quantification of α–Amylase mRNA in *Bacillus subtilis* by Nucleic Acid Sandwich Hybridization", DNA, vol. 7, No. 2, 1988, pp. 135–142.
A. Ballagi–Pordany et al., "Quantitative determination of mRNA phenotypes by the polymerase chain reaction", Analytical Biochemistry, vol. 196, 1991, pp. 89–94.
C. Albretsen et al., "Optimal conditions for hybridization with oligonucleotides: a study with *myc*–oncogene DNA probes", Analytical Biochemistry, vol. 170, 1988, pp. 193–202.

(List continued on next page.)

*Primary Examiner*—Kenneth R. Horlick
*Attorney, Agent, or Firm*—Knobbe Martens Olson & Bear

[57] ABSTRACT

The invention includes methods for the detection of a particular genus or species of fungus in a biological sample. Some of these methods make use of a solid support-polynucleotide structure. This structure includes a solid support having immobilized thereto a polynucleotide probe that is complementary to a sequence of ribosomal RNA (rRNA) specific to the particular species of fungus. An rRNA sequence from the particular species of fungus is hybridized to the first probe, and a second polynucleotide probe is also hybridized to the rRNA.

2 Claims, 4 Drawing Sheets

OTHER PUBLICATIONS

R. J. Cano et al., "DNA hybridization assay using ATTOPHOS™, a fluorescent substrate for alkaline phosphatase", Biotechniques, vol. 12, No. 2, Feb. 1992, pp. 264–269.

Polsky–Cynkin et al., "Use of DNA Immobilized on Plastic and Agarose Supports to Detect DNA by Sandwich Hybridization", Clinical Chemistry, vol. 31, No. 9, 1985, pp. 1438–1443.

Hayashi et al., "A Novel Diagnostic Method of *Pneymocystis carinii*", Laboratory Investigation, vol. 63, No. 4, 1990, pp. 576–580.

Giovannoni et al., "Phylogenic Group–Specific Oligodeoxynucleotide Probes for Identification of Single Microbial Cells", Journal of Bacteriology, vol. 170, No. 2, Feb. 1988, pp. 720–726.

Saiki et al., "Primer–Directed Enzymatic Amplification of DNA with a Thermostable DNA Polymerase", Science, vol. 239, 29 Jan. 1988, pp. 487–491.

I. Raineri et al., "Improved Efficiency for Single–Sided PCR by Creating a Reusable Pool of First–Strand cDNA coupled to a Solid Phase", Nucleic Acids Research, vol. 19, No. 14, 1991, p. 4010.

S. Inouye et al., "Microplate Hybridization of Amplified Viral DNA Segment", Journal of Clinical Microbiology, vol. 28, No. 6, Jun. 1990, pp. 1469–1472.

R. Bischoff et al., "Introduction of 5'–Terminal Functional Groups into Synthetic Oligonucleotides for Selective Immobilization", Analytical Biochemistry, vol. 164, No. 2, 01 Aug. 1987, pp. 336–344.

J. Rey–Campos et al., "Synthesis of Thymosin $\alpha_1$ Precursor cDNA and Purification of Active mRNA by Affinity Chromatography", International Journal of Biochemistry, vol. 15, 1983, pp. 155–157.

T. Atkinson et al., "A convenient procedure for the synthesis of oligodeoxyribonucleotide affinity columns for the isolation of mRNA", Nucleic Acids Research, vol. 16, No. 13, 1988, p. 6232.

J. A. Arias et al., "Promoter–dependent Transcription by RNA Polymerase II Using Immobilized Enzyme Complexes", Journal of Biological Chemistry, vol. 264, No. 6, 1989, pp. 3223–3229.

C. R. Thrash et al., "Synthesis of RNA from Cellulose–bound Complementary DNA", Journal of Biological Chemistry, vol. 252, No. 16, 1977, pp. 5615–5618.

Y. Wataya et al., "Kagaku Ryoho no Ryoiki", vol. 8, No. 3, 1992, pp. 487–496.

M. S. Urdea et al., "A comparison of non–radiosotopic hybridization assay methods using fluorescent chemiluminescent and enzyme labeled synthetic oligodeoxyribonucleotide probes", Nucleic Acids Research, vol. 16, No. 11, 1988, pp. 4937–1956.

Bethesda Research Laboratories Life Technologies, Inc. Product: Vanadyl Ribonucleoxide Complex.

Biofeedback; "A Procedure for Productive Coupling of Synthetic Oligonucleotides to Polystyrene Microtier Wells for Hybridization Capture"; Biotechniques; vol. 8, pp. 278–279, 1990.

Pal Venetianer, et al., Pro Nat. Acad. Sci. USA, V1.71, No. 10, pp. 3892–3895, Oct. 1974; "Enzymatic Synthesis of Solid Phase–Bound DNA Sequences Corresponding to Specific Mammalian Gene".

P. T. Gilham, Journal of the American Chemical Society, vol. 86, pp. 4982–4985; "The Synthesis of Polynucleotide–Celluloses and Their use in the Fractionation of Polynucleotides".

M. R. Ven Murthy, et al., Nucleic Acids Research, vol. 14, No. 17, Jul. 24, 1986; "Preparation and Biochemical Manipulation of mRNAs and CDNAs on small Oligo(dt)–cellulose discs".

Jane A. Matthews, et al., Analytical Biochemistry 169, pp. 1–25 (1988); "Analytical Strategies for the Use of DNA Probes".

Stefan Stamm, et al., Nucleic Acids Research, vol. 19, No. 16, pp. 1350; "Sanchored PCR: PCR with cDNA Coupled to a Solid Phase".

R. Julian S. Duncan, et al., Analytical Biochemistry 132, pp. 68–73 (1983); "A New Regent Which May Be Used to Introduce Sulfhydryl Groups into Proteins, and Its Us in the Preparation of Conjugates for Immunoassay".

Seiichi Hashida, et al., Journal of Applied Biochemistry 6, pp. 56–63 (1984); "More Useful Maleimide Compounds for the Conjugation of Fab' to Horseradish Peroxidase through Thiol Groups in the Hinge".

Hidenori Yamada, et al., Biochemistry 1981, 20 pp. 4836–4842; "Selective Modification of Aspartic Acid–101 in Lysozyme by Carbodiimide Reaction".

James V. Staros, et al., Analytical Biochemistry 156, pp. 220–222 (1986); "Enhancement by N–Hydroxsulfosuccinimide of Water–Soluble Carbodiimide–Mediated Coupling reactions".

Norman Arnheim, et al., C&EN, Oct. 1, 1990, pp. 36–46; "Polymerase Chain Reaction".

Bowman, Barbara H.; Clinical Immunology Newsletter; "Designing a PCR/PRobe Detection System for Pathogenic Fungi". vol. 12, No. 5, May 1992; pp. 65–69.

FUNGAL DETECTION SYSTEM BASED ON RRNA PROBES

This application is a continuation of application Ser. No. 07/922,522, filed Jul. 28, 1992, abandoned.

FIELD OF THE INVENTION

The present invention comprises a method for detecting the presence of a particular species of fungus in a biological sample by identifying ribosomal RNA in the sample complementary to a specific polynucleotide probe which only hybridizes with a sequence contained in the ribosomal RNA of the particular species of fungus. A second, labeled probe complementary to another sequence on such ribosomal RNA can be used in order to facilitate detection. Common and specific sequences of fungal ribosomal RNA for use in the present method are also included.

BACKGROUND OF THE INVENTION

Although fungi are responsible for a number of serious disease conditions, they often parasitize humans without causing overt symptoms of disease. For example, the fungus *Candida albicans* is commonly found among the flora inhabiting the skin, mouth, and intestinal tract of a human. When fungi do produce detectable disease in otherwise healthy individuals, they usually cause mild infections such as athlete's foot, a topical fungal infection.

Individuals whose immune systems are compromised, however, are at much greater risk for contracting serious fungal infections. The normally harmless fungus *Candida albicans*, for example, is an opportunistic pathogen and can cause serious disease in immunocompromised patients. People who take immunosuppresive medication or who suffer from AIDS, therefore, are particularly susceptible to opportunistic fungal infections.

Heretofore, in order to diagnose a fungal infection, a diagnostician must have first observed symptoms or suspected other reasons in a patient that indicate that the patient might be suffering from a fungal infection. The presence of a fungal pathogenic agent and the identification of a particular species of fungus responsible for causing such symptoms can generally only be confirmed by taking a biological sample from the patient and culturing the sample. After a period of time, the culture is visually observed, and if a fungus grows in the culture in numbers sufficient to indicate a fungal infection, that fungus is identified by observing its morphological characteristics.

SUMMARY OF THE INVENTION

One aspect of the present invention involves a method of detecting the presence of a particular fungal genus or species in a biological sample containing ribosomal RNA (rRNA). This aspect of the invention involves bringing the rRNA present in the sample into contact with a first polynucleotide probe immobilized on a solid support. In one embodiment, the solid support is a microtiter plate having a plurality of wells, each of the wells having a first polynucleotide probe immobilized thereon. Thus, when using this embodiment, the rRNA in the sample can be brought into contact with a plurality of first polynucleotide probes, with each of the first polynucleotide probes being complementary to an rRNA sequence specific to a different fungal species. The first first polynucleotide probe has a sequence that is complementary to an rRNA sequence specific to the particular fungal genus or species. In a preferred embodiment, the first polynucleotide probe, when hybridized to a complementary sequence, has a melting temperature ($T_m$) (i.e. the temperature at which the two strands separate) within the range from approximately 48° C. to approximately 60° C., more preferably approximately 54° C. Thus, for example, the first polynucleotide probe can be a DNA sequence complementary to one of the following: SEQ ID NO:81, SEQ ID NO:104, SEQ ID NO:131 through SEQ ID NO:133, SEQ ID NO:154 through SEQ ID NO:156, SEQ ID NO:176, SEQ ID NO:199, SEQ ID NO:267, SEQ ID NO:290, SEQ ID NO:312, SEQ ID NO:335, SEQ ID NO:364 through SEQ ID NO:376, SEQ ID NO:391 through SEQ ID NO:392 or a sequence homologous to any of the foregoing. If there is rRNA in the sample that is complementary to the first polynucleotide probe it will hybridize with the first polynucleotide probe. Preferably, the solid support is washed after hybridizing the rRNA to the first polynucleotide probe so that substantially all of the biological sample not annealed to the first polynucleotide probe on the solid support is removed from the solid support. After hybridization of the rRNA to the first polynucleotide probe, a second polynucleotide probe is brought into contact with the solid support, and allowed to hybridize to any rRNA annealed to the first polynucleotide probe immobilized on the support. The second polynucleotide probe has a sequence that is complementary to a rRNA sequence common to a plurality of fungal species, preferably common to five or more fungal species. In a preferred embodiment, the second polynucleotide probe has the same or lower $T_m$ as the first polynucleotide probe. Thus, for example, the second polynucleotide probe can be a sequence complementary to any one of SEQ ID NO:1 through SEQ ID NO:80 or a sequence homologous thereto. Preferably, the solid support is washed after hybridizing the second polynucleotide probe with the rRNA so that substantially all of the first polynucleotide probe not hybridized with the rRNA is removed from the solid support. The presence of the particular fungal genus or species in the sample is determined by detecting the presence of the second polynucleotide probe hybridized to the rRNA from the sample which is hybridized to the first polynucleotide probe immobilized on the support. In a preferred embodiment, a label, such as a radionuclide, an enzyme, an enzyme substrate, a specific binding moiety, an binding partner for a specific binding moiety, biotin, avidin or a flouresecent material, is attached to the second polynucleotide probe, so that detection thereof can be made more easily.

In another aspect, the present invention provides a method of detecting the presence of minute quantities of a particular fungal genus or species in a biological sample containing ribosomal RNA (rRNA). In this aspect of the invention, A biological sample containing rRNA is obtained. This sample is contacted with a first common polynucleotide primer. The first common primer has a sequence that is complementary to a sequence of rRNA common to a plurality of fungal species. Thus, a sequence complementary to any one of SEQ ID NO:1 to SEQ ID NO:80 can be used. The first common polynucleotide primer hybridizes to fungal rRNA present in the sample, if rRNA complementary to the first common polynucleotide primer is present. Thus, if such rRNA is present, the primer can be extended, preferably using reverse transcriptase, thereby producing a double-stranded polynucleotide including a complementary strand having a sequence complementary to the rRNA. In a preferred embodiment, a second common polynucleotide primer that is complementary to the complementary strand is added and extended, thereby producing a double-stranded polynucleotide including a complementary strand having a sequence complementary to the rRNA and a strand having a sequence homologous to the rRNA. The primer can be annealed and extended a plurality of times to amplify any rRNA sequences having complementarity or homology to the two common primers. At least some of the sequences of the double-stranded polynucleotide can be reproduced by adding a first specific primer and a second specific primer and extending these specific primers. The first specific primer has a sequence complementary to an rRNA sequence specific to the particular fungal species, and the second specific primer has a sequence complementary to the complementary strand produced in the first extension step and is also homologous to a part of the rRNA that is specific to the particular fungal species. In a preferred embodiment, the first specific polynucleotide primer and/or the second specific polynucleotide primer has a $T_m$ the same as or less than the first common polynucleotide primer. Thus, in certain embodiments of this aspect of the present invention, such as where the first common polynucleotide primer is complementary to one of SEQ ID NO:1 through SEQ ID NO:80, at least one of the two specific polynucleotide primer is a polynucleotide strand comprising a sequence homologous or complementary to a sequence selected from the group consisting of SEQ ID NO:81, SEQ ID NO:104, SEQ ID NO:131 through SEQ ID NO:133, SEQ ID NO:154 through SEQ ID NO:156, SEQ ID NO:176, SEQ ID NO:199, SEQ ID NO:267, SEQ ID NO:290, SEQ ID NO:312, SEQ ID NO:335, SEQ ID NO:364 through SEQ ID NO:376, and SEQ ID NO:391 through SEQ ID NO:392. Preferably, DNA polymerase, especially one that has significant polymerase activity at temperatures above 50° C., and the four deoxynucleotide triphosphates (dNTP's) are used for these extensions. This results in the production of a double-stranded polynucleotide including a complementary strand having a sequence complementary to the rRNA and a homologous strand having a sequence homologous to the rRNA. These extension steps can be repeated a number of times to amplify the polynucleotide appreciably. The presence of the particular fungal species in the sample can then be detected by detecting the extension of at least one of the first or second specific polynucleotide primer. In one embodiment, this is done by labeling at least one of the first or second specific primers and detecting the extension of the labeled primer. The primers can be labeled with any of a variety of labels, including a radionuclide, an enzyme, an enzyme substrate, a specific binding moiety, an binding partner for a specific binding moiety, biotin, avidin or a flouresecent material. In some embodiments, the detection step involves hybridizing at least one of the complementary strand or the homologous strand with a polynucleotide probe that is complementary to the complementary strand or the homologous strand, and detecting the presence of the hybridization between the strand and the probe. This step preferably involves washing the solid support after the step of hybridizing the complementary polynucleotide with the specific polynucleotide probe immobilized on the solid support. The probe can have a sequence either homologous or complementary to a sequence specific to the rRNA of the particular fungal species. Thus, the probe can be a polynucleotide strand comprising a sequence homologous or complementary to one of the following sequences: SEQ ID NO:81, SEQ ID NO:104, SEQ ID NO:131 through SEQ ID NO:133, SEQ ID NO:154 through SEQ ID NO:156, SEQ ID NO:176, SEQ ID NO:199, SEQ ID NO:267, SEQ ID NO:290, SEQ ID NO:312, SEQ ID NO:335, SEQ ID NO:364 through SEQ ID NO:376, and SEQ ID NO:391 through SEQ ID NO:392. In a preferred embodiment, the probe is immobilized to a solid support and the strand hybridizing to the probe bears a label. Detection can then be accomplished by detecting the presence of label on the solid support.

Another aspect of the present invention provides a solid support-polynucleotide structure for identifying the presence of a particular genus or species of fungus in a biological sample. This structure includes a solid support having immobilized thereto a first polynucleotide probe. This first probe is complementary to a sequence of ribosomal RNA (rRNA) specific to the particular genus or species of fungus. The structure also includes an rRNA sequence from the particular genus or species of fungus. This rRNA sequence is hybridized to the first probe. The structure also includes a second polynucleotide probe complementary to a second sequence of rRNA present in the rRNA of the species of fungus. In a preferred embodiment, the second polynucleotide probe can include a label, such as a radionuclide, an enzyme, an enzyme substrate, a specific binding moiety, an binding partner for a specific binding moiety, biotin, avidin or a flouresecent material. The second polynucleotide probe can be specific to the rRNA of the specific species of fungus, or it can also be common to the rRNA of a plurality of pathogenic fungal species.

Other aspects of the present invention relate to an isolated segment of polynucleotide specific to the rRNA of a particular genus or species of fungus, and to sequences common to a plurality of fungal species. Thus, the present invention includes isolated sequences complementary or homologous to one of the following sequences: SEQ ID NO:1 through SEQ ID NO:81, SEQ ID NO:104, SEQ ID NO:131 through SEQ ID NO:133, SEQ ID NO:154 through SEQ ID NO:156, SEQ ID NO:176, SEQ ID NO:199, SEQ ID NO:267, SEQ ID NO:290, SEQ ID NO:312, SEQ ID NO:335, SEQ ID NO:364 through SEQ ID NO:376, SEQ ID NO:391 through SEQ ID NO:392

A further aspect of the present invention involves a kit for identifying the presence of a particular genus or species of fungus in a biological sample. The kit includes at least one specific polynucleotide probe. This specific probe is complementary to or homologous to a sequence of ribosomal RNA (rRNA) specific to the particular species or genus of fungus. In one embodiment, the specific polynucleotide probe includes a sequence complementary to or homologous to one of the following sequences: SEQ ID NO:81, SEQ ID NO:104, SEQ ID NO:131 through SEQ ID NO:133, SEQ ID NO:154 through SEQ ID NO:156, SEQ ID NO:176, SEQ ID NO:199, SEQ ID NO:267, SEQ ID NO:290, SEQ ID NO:312, SEQ ID NO:335, SEQ ID NO:364 through SEQ ID NO:376, and SEQ ID NO:391 through SEQ ID NO:392. The kit also includes a common polynucleotide probe complementary to or homologous to a second sequence of rRNA present in the rRNA of the genus or species of fungus. This common polynucleotide probe is complementary to rRNA from a plurality of fungal species. In certain embodiments, the common polynucleotide probe includes a sequence complementary to or homologous to any of SEQ ID NO:1 through SEQ ID NO:80. One or more of the probes can be labeled, such as with a radionuclide, an enzyme, an enzyme substrate, a specific binding moiety, an binding partner for a specific binding moiety, biotin, avidin or a flouresecent material. The kit can optionally also include a solid support to which a polynucleotide can be immobilized. Thus, in certain embodiments, the specific nucleotide probe is immobilized to the solid support. The solid support can have a plurality of specific nucleotide probes immobilized thereto, with each of the probes specific to a different species of fungus. Thus, in these embodiments, the common polynucleotide probe can be complementary to a sequence in the ribosomal rRNA of each of the different species of fungus. Further, in some embodiments, the solid support has a plurality of wells, with each of several specific nucleotide probes immobilized to a different one of the wells. The kit can also optionally include a buffer appropriate for hybridization of the probes to rRNA.

In an alternative embodiment of the kit, the specific polynucleotide probe is a first specific primer and the kit also includes second specific polynucleotide primer specific to a different part of the rRNA specific to the particular genus or species of fungus. The second specific primer is complementary to the rRNA if the first specific primer is homologous to the rRNA and is homologous to the rRNA if the first specific primer is complementary to the rRNA. In this alternative kit, the common polynucleotide probe can be a first common primer, with the kit including second common polynucleotide primer common to a plurality of fungal species. Similarly to the second specific primer, the second common primer is complementary to the rRNA if the first common primer is homologous to the rRNA and homologous to the rRNA if the first common primer is complementary to the rRNA. In a certain embodiment, the kit can also include at least one of the following: dNTP's, a reverse transcriptase, a polymerase, and a buffer appropriate for addition of dNTP's to a primer using a reverse transcriptase or polymerase. In a preferred form of this embodiment, the kit includes a DNA polymerase that has significant polymerase activity at temperatures above 50° C.

DETAILED DESCRIPTION OF THE INVENTION

Figure 1:
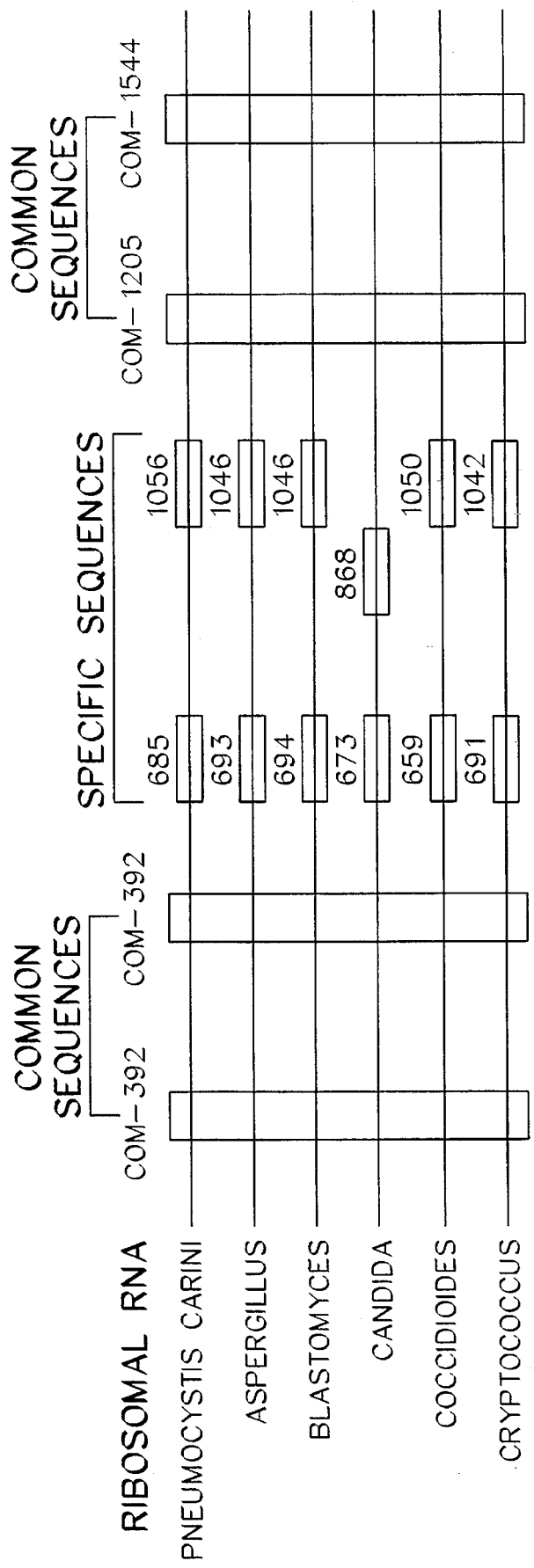
FIG. 1 is a schematic representation of one embodiment of the method of the present invention.

The recent prevalence of AIDS, a disease which compromises the immune system, has led to an increase in the number of opportunistic fungal infections encountered by health care providers. Prior art methods of detecting such fungal infections, however, have proven to be deficient in several respects. In prior art methods, a biological sample must be cultured in order to detect a fungus. This requires that the sample be grown in an appropriate media until a fungus present in the sample is visually detectable and can be categorized morphologically.

It can take days to culture a fungus with prior art methods, thus making such methods slow. Moreover, since the growth requirements of different fungi are different, a biological sample would have to be cultured on a variety of culture media in order to verify the presence of different pathogenic fungi. Further, prior art methods provide no means of quantifying the extent of a fungal infection. The need to rely on the expertise of a microbiologist in order to identify the fungal pathogen at work and to verify that the pathogen is fungal in origin is another disadvantage of prior art methods. There is therefore a great need for an improved way to quickly and accurately determine the presence of a fungus in a biological sample.

Common and Specific Sequences

We have discovered a number of specific sequences that are unique to the rRNA of a single fungal species or genus. These sequences arc SEQ ID NO:81, SEQ ID NO:104, SEQ ID NO:131 through SEQ ID NO:133, SEQ ID NO:154 through SEQ ID NO:156, SEQ ID NO:176, SEQ ID NO:199, SEQ ID NO:267, SEQ ID NO:290, SEQ ID NO:312, SEQ ID NO:335, SEQ ID NO:364 through SEQ ID NO:376, and SEQ ID NO:391 through SEQ ID NO:392. Reference can be made to Tables V through XVI for a comparison of these specific sequences to corresponding sequences in other species or genera.

SEQ ID NO:227 and SEQ ID NO:250 are sequences that are specific to the rRNA of certain strains of *C. albicans*. However, reported sequences in other strains of the same species have slight changes in these sequences in their rRNA, as seen in SEQ ID NO:226 and SEQ ID NO:249, respectively. Accordingly, these particular sequences are less preferred for use as specific sequences within the context of the present invention. However, these sequences can be useful for identifying the particular strain of *C. albicans* in a sample.

We have also discovered a number of common sequences that are common to the rRNA of several fungal species and genera. These sequences are SEQ ID NO:1 through SEQ ID NO:80. Reference can be made to Tables 1 through 4 to see that these sequences are common to all species shown.

Advantageously, all of these probes, both common and specific, have been designed to all have approximately, the same melting temperature ($T_m$)) when annealed to a complementary sequence; all are within 1° C. of 54° C. Thus, various procedures requiring annealing of these sequences can all be performed under the same conditions. Those of skill in the art will recognize that longer or shorter sequences, with a correspondingly higher or lower $T_m$, respectively, can also be obtained upon reference to the full-length sequences available from GenBank, as shown in Table 1 below. When the term "$T_m$" is used herein in connection with a single-stranded polynucleotide, this term refers to the melting temperature of that single-stranded polynucleotide when it is annealed to a complementary strand.

As is known to those of skill in the art, the $T_m$ of a polynucleotide strand can be determined using the following formulas:

(a) $T_m = 69.3 + 0.41 (G+C)\% - 650/L$
(where G is the number of guanine residues in the strand, C is the number of cytosine residues, and L is the total length, in bases, of the polynucleotide);

(b) $(T_m)u_2 - (T_m)u_1 = 18.5 \log_{10} u_2/u_1$
(where $u_1$ and $u_2$ are the ionic strengths of two solutions); and (c) The Tm of duplex DNA decreases 1° C. with every increase of 1% in the number of mismatched base pairs.

In a preferred embodiment of the present invention, a plurality of probes that have the same $T_m$ are immobilized to one or more solid supports. When probes having the same $T_m$ are used, such probes can be hybridized together under the same conditions because they require the same reaction temperatures. Preferably, the specific probes in this embodiment have a $T_m$ between approximately 48° C. and 60° C. Other probes that have the same $T_m$ and are within this range can be determined by using the formulas above and by performing routine experimentation.

Fungus Assay

We have discovered that the presence of a particular species of fungus in a biological sample can be determined by probing the ribosomal RNA of a sample for sequences specific to the ribosomal RNA of a particular species of fungus. It has been found that each one of a plurality of fungal species carries ribosomal RNA sequences specific to only one species of fungus. The presence of a particular species of fungus in a biological sample can thus be detected by probing that sample for a sequence of ribosomal RNA found only in the ribosomal RNA of that species of fungus.

The specific ribosomal RNA sequences found in a number of species of fungus appear to occur in regions that pick up mutations at a relatively high rate. Thus, many species of fungi are likely to have different nucleotide sequences in those regions. Although ribosomal RNA is not expressed, such regions would be analogous to unexpressed regions of genomic DNA, which pick up mutations at a relatively faster rate than expressed regions.

It has been further discovered that a number of species of fungi share sequences of ribosomal RNA common to all of those species. Thus, the presence of any of those fungal species in a biological sample can be determined by probing the sample for polynucleotides having such common sequences. If a fungus contains both specific and common sequences, probing for such common sequences can be used to detect the presence of a variety of that species of fungus which contains one or more mutations in its specific ribosomal RNA sequences. The existence of common sequences can also be exploited by annealing labeled probes to those sequences in order to facilitate the detection of polynucleotides which carry such common sequences.

In one group of pathogenic fungal species, two separate ribosomal RNA sequences have been identified in each of the species which are specific to the individual species carrying such sequences. This group comprises the following fungal species: *Pneumocystis carinii, Aspergillus fumagatus, Aspergillus fumigatus, Cryptococcus neoformans, Coccidiodes immitis, Blastomyces dermatitidis*, and a number of species in the Candida group, including *Candida albicans* and *Candida tropicalis*. The Genbank accession numbers of the ribosomal RNA of the fungal species of this group are shown in Table A below:

TABLE A

| Fungal Species | Accession No. |
| --- | --- |
| *Aspergillus fumagatus* | M55626 |
| *Aspergillus fumagatus* | M60300 |
| *Aspergillus fumagatus* | M60301 |
| *Blastomyces dermatitidis* | M55624 |
| *Candida albicans* | M60302 |
| *Candida albicans* | X53497 |
| *Candida guilliermondii* | M60304 |
| *Candida glabrata* | X51831 |
| *Candida kefyr* | M60303 |
| *Candida krusei* | M55528 |
| *Candida krusei* | M60305 |
| *Candida lusitaniae* | M55526 |
| *Candida lusitaniae* | M60306 |
| *Candida parapsilosis* | M60307 |
| *Candida tropicalis* | M55527 |
| *Candida tropicalis* | M60308 |
| *Candida viswanathii* | M60309 |
| *Pneumocystis carinii* | X12708 |
| *Coccidiodes immitis* | M55627 |
| *Cryptococcus neoformans* | M55625 |

As used in the present application, the term "specific sequence" denotes a sequence which is present only in the ribosomal RNA of one species of fungus. The sequence is specific to that fungus species and not found in the ribosomal RNA of any other fungal species. The sequence is also different from other RNA sequences found in the cells being tested. A probe which has a sequence complementary to one of these specific sequences will therefore anneal only to the ribosomal RNA of a particular species of fungus, or to a polynucleotide homologous to such ribosomal RNA. Such a probe is therefore said to be specific to the particular species of fungus.

Of course, the sequence complementary to a specific sequence can also be said to be specific. The term "complementary" is used to describe a polynucleotide sequence in which adenine is replaced by thymine or a nucleotide that reacts in an equivalent way to thymine such as uracil, and in which thymine (or uracil) is replaced by adenine or a nucleotide that reacts in a similar way to adenine. In such a complementary molecule the guanine residues would also be replaced by cytosines or equivalent nucleotide molecules, and the cytosine residues would be replaced by guanine or equivalent nucleotides.

In the present application, the term "homologous" is used to describe a polynucleotide having a sequence which contains the same nucleotides or equivalent nucleotides, in the same order, as another polynucleotide. For example, a second polynucleotide having the same sequence of nucleotides as a first polynucleotide but in which uracil residues have been substituted for the thymine residues is homologous to the first polynucleotide. Other equivalent nucleotide substitutions known to the art are also included.

In the group of pathogenic fungi containing specific sequences referred to above, four common sequences of ribosomal RNA have also been identified. As shown in FIG. 1, two of these common sequences occur 5' of the specific sequences identified in such fungi, while two other common sequences are located 3' of these specific sequences. Thus, in one embodiment of the present invention, primers complementary to the common sequences located 3' of the specific sequences in the ribosomal RNA of a fungal species of this group are used to create a polynucleotide, preferably a strand of cDNA, complementary to the portion of the ribosomal RNA of the species that contains the specific sequences. In another embodiment, a probe homologous to one of the common sequences located 5' of the specific sequences is anneal to a strand complementary to the ribosomal RNA of a species of fungus in order to create a polynucleotide strand homologous to the strand of fungal ribosomal RNA that contains at least one of the sequences specific to a particular fungus.

Obtaining a Biological Sample

In order to obtain a biological sample containing a fungus, an organism or tissue suspected of harboring a particular species of fungus can be identified. The identification can be made in any way known to the art. Preferably, the organism suspected of carrying a fungus is a human, and the identification is made by a physician who observes symptoms of a fungal infection in such a human. For example, a patient diagnosed as having AIDS who comes down with pneumonia and who does not respond to anti-bacterial agents is identified by a physician as possibly harboring the fungus *Pneumocystis carinii*.

Alternatively, a biological sample without overt signs of harboring a fungus can be tested for the presence of a fungal species. For example, a food sample or tissue from an AIDS patient without signs of a fungal growth can be tested for the presence of a fungus. In this embodiment, any biological sample can be tested, even though overt signs of the presence of a fungus are lacking in that sample. Appropriate action may thereby be taken if a fungus is in fact found in such a biological sample.

The biological sample to be tested can be obtained by any means known to the art. For example, if an AIDS patient is suspected of suffering from interstitial plasma pneumonia caused by the fungus *Pneumocystis carinii*, a sputum sample can be taken from the lungs of that patient. The sputum can be obtained by having the patient cough up phlegm from the lungs and deposit it into a cup. Alternatively, a sputum sample can be obtained by scraping the bronchial passage with a sterile swab, or by any other means known to the art. Any other biological sample which could possibly carry a fungus is likewise obtained in an appropriate fashion.

Preparing the Biological Sample

The biological sample is next prepared so that the ribosomal RNA of any fungi present in the sample can be probed in accordance with the methods of the present invention. In order to probe the ribosomal RNA of any fungal cells present, these cells should first be lysed. Lysis can be accomplished by any of a number of methods known to the art, including those set out in *Molecular Cloning: A Laboratory Manual* (1989) by Maniatis, et al., hereby incorporated by reference.

In one embodiment, the cells are lysed before they come into contact with the solid support. This embodiment might be used, for example, when the solid support is one which is not designed to hold a sample of lysed cells, such as a nitrocellulose filter. In this embodiment, the cells are contacted with the solid support after they have been lysed.

A variety of techniques can be used for cell lysis. Techniques that separate the ribsomal RNA from the ribosomal proteins are preferred. Example 1 is provided to show one technique believed to be useful in obtaining ribosomal RNA. However, techniques for obtaining ribosomal RNA are well known. Thus, the technique of Example 1 is not necessarily a preferred method of obtaining ribosomal RNA-containing samples. Example 1, like all of the examples provided herein, are provided merely to illustrate certain aspects of the present invention. As such, they are not intended to limit the invention in any way.

EXAMPLE 1

Lysing Cells in a Biological Sample

Cells present in a biological sample can be lysed by treatment with a solution of 10 mM ethylenediaminetetraacetic acid (EDTA) (pH 8.0), 0.2M NaCl, 0.5% of sodium dodecyl sulfate (SDS), 500 Unit/ml of RNase inhibitor, 10mM of Vanadyl Ribonucleosyl Complex and 200 µg/l of Proteinase K (hereafter called Lysis Buffer). After lysis of the cells, the NaCl concentration of the resulting cell lysate in solution is adjusted to 0.5M.

Solid Support

In a preferred embodiment, the solid support is capable of containing a biological sample and is resistant to the reagents used to lyse the cells in the biological sample. The sample can thus be lysed in the solid support. However, this is not necessary, as the sample can be obtained without lysis or can be lysed in a separate container. An example of a solid support that is resistant to a large number of treatments, the support can be a microtiter well or a plate made from a resistant plastic material.

The solid support can also be any of a variety of other solid supports known to the art, such as a membrane filter, a bead, or any other solid, insoluble support to which polynudeotides can be attached. The solid support is preferably made of a material which can immobilize a polynucleotide probe. Immobilization can be through covalent bonds or through any of a variety of interactions that are known to those having skill in the art. Plastic materials containing carboxyl or amino groups on their surfaces, such as polystyrene, are preferred for the solid support of the present invention because polynucleotide probes can be immobilized on their surfaces, because they are inexpensive and easy to make, and because they are resistant to the reagents used to lyse the cells of the biological samples used in the present invention. For example, the Sumilon microtiter plate MS-3796F made by Sumitomo Bakelite, which has a carboxyl group on its surface, can be used in such a preferred embodiment. A plastic plate having an amino group on its surface, such as the Sumilon microtiter plate MS-3696, can also be used.

Contacting the Sample and First Polynucleotide Probe

After the cells in the biological sample have been lysed, the ribosomal RNA contained in such cells is substantially released into solution or otherwise made available to being probed. If the biological sample was not lysed in the solid support, the cell lysate is next brought into contact with the solid support. Immobilized to the solid support is a first polynucleotide probe which contains a sequence complementary to a specific sequence in the ribosomal RNA of a particular genus or species of fungus. When the ribosomal RNA present in the cell lysate contacts the solid support, therefore, it also comes into contact with the first polynucleotide probe.

Preferably, the first polynucleotide probe is an oligodeoxyribonucleotide (DNA) rather than an oligoribonucleotide (RNA), since DNA is more stable than RNA. The number of nucleotides in the polynucleotide probe is not restricted. However, if an oligodeoxynucleotide is used as the specific polynucleotide probe, a preferred length for the oligodeoxynucleotide is from 15 to 100 nucleotides. Lengths longer than 100 nucleotides are usable within the scope of the present invention. However, lengths of 100 nucleotides or less are preferable because many automated polynucleotide synthesizers have a limit of 100 nucleotides. Longer sequences can be obtained by ligating two sequences of less than 100 nucleotides.

In one preferred embodiment, the first polynucleotide probe is an oligonucleotide complementary to one of the following sequences: SEQ ID NO:81, SEQ ID NO:104, SEQ ID NO:131 through SEQ ID NO:133, SEQ ID NO:154 through SEQ ID NO:156, SEQ ID NO:176, SEQ ID NO:199, SEQ ID NO:267, SEQ ID NO:290, SEQ ID NO:312, SEQ ID NO:335, SEQ ID NO:364 through SEQ ID NO:376, or SEQ ID NO:391 through SEQ ID NO:392. These sequences are specific to the ribosomal RNA of various pathogenic species of fungi, as listed in the sequence listing, and Tables V through XII.

Example 2 is provided to show one particular probe that is useful for determining the presence of *Pneumocystis carinii* in a biological sample.

EXAMPLE 2

Preparing the First Polynucleotide Probe

A first polynucleotide probe that is specific to a sequence of ribosomal RNA in *Pneumocystis carinii* is prepared. The probe is produced with a DNA synthesizer such as a DNA synthesizer made by Applied Biosystems of Menlo Park, Calif. The probe is complementary to a polynucleotide having the following sequence where A, T, G, and C stand for adenine, thymine, guanine and cytosine, respectively: 5'-GCGCAACTGATCCTTCCC-3' (SEQ ID NO:81).

Immobilizing the First Polynucleotide Probe

Various methods of immobilizing polynucleotides to a solid support are known to the art, including covalent binding, ionic binding, and the physical absorbance method. In certain embodiments of the present invention, the polynucleotides are immobilized to microtiter wells which exhibit functional groups such as carboxyl residues, amine residues, or hydroxyl residues on the surfaces thereof. Thus, in one procedure for the immobilization of the first polynucleotide probe to a solid support exhibiting a functional group, the 5'-terminal end of the polynucleotide is covalently linked to the functional group. Any of a variety of methods for the covalent binding of polynucleotides to these functional groups can be used. Examples of preferred, well-known methods include the maleimide method and the carbodiimide method.

The maleimide method involves a reaction between a substance containing a maleimide group and another material containing a sulfhydryl residue (SH). The 5' end of the specific polynucleotide probe is immobilized on a solid support in this method by reacting the 5' end of the polynucleotide with a maleimide compound. A suitable maleimide compound is sulfosuccinimidyl-4-(N-maleimidomethyl-)cyclohexane-1-carboxylate (sulfo-SMCC).

The SH residue is provided on the support by a reaction between a support having an amino group and succinimidyl-S-acetylthioacetate (SATA), followed by deacetylation using hydroxylamine ($NH_2OH$). Sulfo-SMCC and SATA are readily available from a variety of commercial sources, including the Pierce Company. The resulting SH group on the support is reacted with the maleimide group on the 5' end of the first polynucleotide probe when these groups are brought into contact under the appropriate conditions, thereby immobilizing the first polynucleotide probe to a solid support.

One problem we have experienced in the use of the maleimide method is that the SH group on the support can react not only with an amino group at the 5' end of the first polynucleotide probe, but also with primary amino groups on the purine bases, adenine and guanine. In order to assure that the polynucleotides are immobilized at their 5' ends, so that the sequences complementary to the ribosomal RNA sequences specific to a particular species of fungus are available for hybridization, the amino groups on the purine bases can be protected by pairing the specific polynucleotide probe to a complementary polynucleotide prior to immobilization. After immobilization, the complementary polynucleotide can be removed through denaturation, such as through heating, leaving the single-stranded probe immobilized to the solid support.

Another method of immobilizing a polynucleotide to a solid support is the carbodiimide method. This method involves a reaction between an amino group and a material containing a carboxyl residue using a carbodiimide compound. An example of a carbodiimide compound is 1-ethyl-3-(3-dimethylaminopropyl)carbodiimide hydrochloride (hereafter called EDC). This reaction can be enhanced with N-hydroxysulfosuccinimide (hereafter called Sulfo-NHS). Both EDC and Sulfo-NHS are available from well known commercial sources, including the Pierce Company.

In the practice of a preferred carbodiimide method for attaching polynucleotides to a solid support, a support having a carboxyl residue attached is used. Before contacting EDC with the support, the EDC is activated by reacting it with Sulfo-NHS. This activated EDC is then reacted with the solid support containing surface-bound carboxyl residues. The support, after being so treated, can be reacted with strands of the first polynucleotide probe, which have an amino group at their 5'-terminal ends, thereby immobilizing the specific polynucleotide probe to the support.

In order to assure that the first polynucleotide probe is immobilized at its 5' end, the primary amino groups on the probe (the adenyl, guanyl and cytosyl groups) can be protected by hybridizing the nucleotide to a complementary polynucleotide prior to immobilization. After immobilization, the complementary polynucleotide can then be removed through denaturation, such as through heating, leaving the single-stranded probe immobilized to the solid support. In order to further prevent the non-specific binding of activated amino or carboxyl residues on solid supports, the solid supports to which the specific polynucleotide probes are immobilized can be treated with a primary amine compound, preferably glycine.

Example 3 is provided as an indication to those of skill in the art of but a single method of immobilizing a probe to a solid support. Those of skill in the art will recognize that any of a variety of methods of so immobilizing the probe can be used, including those described above.

EXAMPLE 3

Immobilizing the First Polynucleotide Probe onto a Solid Support with the Carbodiimide Method Both EDC and sulfo-NHS (Pierce, Ill.) are dissolved in DEPC-treated water at concentrations of 20 mM and 10mM, respectively. EDC/Sulfo-NHS solution is then prepared by mixing equal volumes of both EDC and sulfo-NHS. The specific nucleotide probe is dissolved in DEPC-treated water at a concentration of 1 μg/μl and then mixed with the EDC/Sulfo-NHS solution in the ration 1:25 (Vol:Vol).

50 μl of this probe solution is added to each well of a microtiter plate (MS-3796F, Sumitomo Bakelite, JAPAN), which is known to have carboxyl groups on the surface of the plate. After incubation at room temperature overnight, the reaction solution is removed by aspiration.

Hybridizing the First Polynucleotide Probe

The ribosomal RNA of the particular fungal species being tested for, if present in the cell lysate, is next hybridized to the first, specific polynucleotide probe immobilized to the solid support. Hybridization can be accomplished by incubating the cell lysate and the first polynucleotide probe at a temperature dependent on a variety of factors, as is well known to those with ordinary skill in the art. These factors include the length of complementary nucleotide sequences, the ratio of guanine and cytosine bases to the entire base content in the complementary nucleotide sequences (the GC content), the NaCl concentration in the buffer solution, the number of bases which mismatch in the complementary nucleotide sequence, and the type of nucleotide. In a preferred form of this invention, the following equation can be used to calculate the preferred incubation temperature ($T_{inc}$):

$$T_{inc}=16.6 \times \log(M)+0.41(GC)+81.5-675/n-15(°C).$$

In the equation shown above, M is the NaCl concentration in solution, GC represents the GC content (the percentage of guanine and cytosine residues in the sequence), and n represents the length of the nucleotide sequences (the number of hybridizing nucleotides). The incubation temperature can also be determined according to methods described in *Molecular Cloning: A Laboratory Manual* (1989) by Maniatis, et al.

The time for incubation is preferably from 1 hour to overnight, and the sample is preferably gently rocked during incubation. Incubation is preferably performed in an appropriate buffer solution. The same buffer used to hybridize RNA and DNA in the Northern Blot or the Dot Blot Methods, as described in the Maniatis treatise, can be used. The buffer is preferably prepared in a way so as not to contaminate it with RNase. If any RNase contamination is present, the activation of RNase should be controlled so as to be as low as possible.

In order to eliminate RNase activity from water used in the methods of this invention, the water is preferably treated with Diethylpyrocarbonate (DEPC). The preferred DEPC treatment involves addition of 0.1% DEPC to the water, followed by storage overnight at 37° C. and sterilization in an autoclave. The DEPC is deactivated by such autoclaving so that it does not interfere with the enzymatic processes of the methods of the present invention. Alternatively, if the water is sterilized in some other manner, the DEPC in the water can be deactivated by other means known to the art.

Example 4 illustrates one method of hybridizing ribosomal RNA in the sample to an immobilized probe.

EXAMPLE 4

Hybridizing the First Polynucleotide Probe to Ribosomal RNA

RNase is removed from a microtiter well to which a first polynucleotide probe having a sequence complementary to SEQ ID NO:81 has been bound by adding 250 µl of Lysis Buffer containing 0.5M NaCl and incubating the well at 45° C. for one hour. The buffer is removed from individual webs by aspiration, and 50 µl of Lysis Buffer containing the biological sample is added to each well. These solutions are incubated at 39° C. for one hour ($T_m$=54°) to allow hybridization and then slowly cooled over the course of 20–30 minutes.

Washing the Solid Support

Following hybridization, the non-hybridized portions of the biological sample are preferably separated from the solid support, so that substantially all of the biological sample not annealed to the first polynucleotide probe is removed from the solid support. If the solid support is a microtiter well, for example, and the first polynucleotide probe is immobilized to the walls or bottom of the well, the non-hybridized cell lysate can be removed by pouring the lysate out of the well or by aspirating the cell lysate. The well itself can then be "washed" or rinsed with a washing solution such as the Lysis Buffer by applying the washing solution to the walls of the well and then removing the washing solution through aspiration.

Contacting and Hybridizing the Second Polynucleotide Probe

When the solid support has been washed, a second polynucleotide probe is then contacted with and hybridized to the strand of ribosomal RNA from the particular fungal species which is hybridized to the immobilized first polynucleotide probe, if such ribosomal RNA was present in the cell lysate. The contacting and hybridization steps are performed as with the first polynucleotide probe, above, or by any other methods known to the art.

In a preferred embodiment, the second polynucleotide probe contains a polynucleotide sequence complementary to a sequence which is common to the ribosomal RNA of a plurality of species of fungus being tested. In this way, the same second polynucleotide probe can be hybridized to the ribosomal RNA of a plurality of fungal species. In an even more preferred embodiment, the second, common probe has the same or lower $T_m$ as the first, specific probe so that the hybridization of the second probe can be performed under the same conditions as the conditions used to hybridize the first probe.

This embodiment of the present invention is preferred when a plurality of specific probes are used to assay for the presence of a plurality of fungal species, because then the same second probe can be annealed to the ribosomal RNA of a plurality of species. The common polynucleotide probe of this embodiment can also advantageously be included in a kit in which a plurality of specific probes are used to detect the presence of a plurality of fungal species. Not only can the same common probe thereby be used with the same The second polynucleotide probe can alternatively comprise a second sequence specific to the ribosomal RNA of the particular species of fungus sought to be identified in the biological sample. This second sequence is complementary to a different specific sequence of the ribosomal RNA of the particular fungal species from the sequence to which the first probe is complementary.

Label

The second polynucleotide probe is preferably labeled in order to easily detect its presence and facilitate the detection of the ribosomal RNA hybridized to the first probe. A variety of chemical substances are available which can label a polynucleotide probe when attached to that probe. For example, a variety of radionuclides can be used, such as the radioisotopes $^{32}P$, $^{35}S$, $^{3}H$, and $^{125}I$. Enzymes or enzyme substrates can also be attached to the second polynucleotide probe in order to label it. Suitable enzymes include alkaline phosphatase, luciferase, and peroxidase.

Other labels known to the art can also be used. For example, a specific binding moiety which binds to a binding partner for that moiety can be used. In this case, a binding moiety such as an antibody is labeled with a marker and then bound to a binding partner, such as an antigen, on the second polynucleotide probe. An agonist and its receptor can also be used, as is known to the art. A receptor such as the norepinephrine receptor attached to the second polynucleotide probe can be detected by the addition of a labeled agonist for that receptor, in this case norepinephrine. Other labels which can be used are chemical compounds such as fluorescein (an colorimetric label), biotin, avidin, streptavidin, and digoxigenin. Labels which provide a colorimetric or radioactive indication are preferred for use in the present invention because such markers allow quantification of the bound probes. Colorimetric labels are especially preferred because they avoid the health hazards and disposal problems associated with the use of radioactive materials.

Example 5 shows one method of using a labeled common polynucleotide probe to identify the presence of rRNA.

EXAMPLE 5

Preparing, Labeling, and Hybridizing the Second Nucleotide Probe

The second nucleotide probe is an oligodeoxynucleotide prepared as in Example 1 comprising a sequence complementary to the following sequence: 5'-GAGGGAGCCT-GAGAAACG-3' (SEQ ID NO:1). This sequence is complementary to the ribosomal RNA of a number of fungal species, including the ribosomal RNA to which the specific polynucleotide probe of Example 1 is complementary. This second nucleotide probe is labeled with fluorescein at either the 3' or 5' end of the probe. The 3' end is labeled using terminal transferase and FITC-dUTP. alternatively, the 5' end is labeled by chemical reaction with FITC. Fifty μl of Lysis Buffer including 0.5M NaCl and 1 μl of a solution containing the second polynucleotide probe to which fluorescein has been attached is added into each well and incubated at 39° for one hour, after which it is allowed to slowly cool (over 20–30 minutes).

Determining the Presence of Fungi in the Sample

After the second polynucleotide probe has been hybridized to any fungal ribosomal RNA that is present, substantially all of the solution containing the second probe is removed from the solid support by aspiration or in any other appropriate way, and the solid support is again washed to remove any unhybridized second polynucleotide. The presence of the particular species of fungus sought to be detected is then finally determined by detecting the presence of the second polynucleotide probe immobilized to the solid support via the ribosomal RNA strand and the first polynucleotide probe. If the second polynucleotide probe is detected, this indicates that the biological sample contained ribosomal RNA from the particular fungal species being tested for, and hence that the biological sample harbors that species of fungus.

In one embodiment of the present invention, a negative control experiment is also performed when the biological sample is tested. The control experiment is run by performing the present method with the same steps and the same materials as when a biological sample is tested, except that no first polynucleotide is attached to the solid support on which the control experiment is performed.

A positive control experiment is also preferably run when performing the methods of the present invention. A positive control is run by performing the present method with the same materials and using the same steps, with the exception that the first polynucleotide probe immobilized to the solid support contains a sequence common to the ribosomal RNA of the fungal species being tested for. Therefore, if any of the species of fungus being tested for are present in the biological sample, the solid support comprising the positive control will indicate the presence of a fungus in the sample.

Quantifying the Amount of Fungus in the Sample

The amount of ribosomal RNA in the biological sample from a particular fungal species can be quantitated by measuring the amount of second polynucleotide probe bound to the solid support after application thereto in accordance with the present invention. The amount of ribosomal RNA in the sample can give a rough measurement of the number of fungi of the particular species contained in the sample, and thus a rough estimate of the extent of an infection if the sample is from a diseased organism.

To quantify the amount of second polynucleotide probe attached to the solid support, a physical or chemical quantity or activity of the label on the second polynucleotide is measured. A number of techniques for measuring the label on a polynucleotide probe known to the art can be used, the technique used depending on the kind of label. Such techniques include measuring the optical density of the buffer solution, the emitted-light intensity of the buffer solution, or the amount of radiation given off by the immobilized second polynucleotide probe. The label itself can provide this indication or can require other compounds which bind thereto or which catalyze the label. Other mechanisms for detecting label include the use of compounds that can chemically react with the label, the detection of a colored label, the detection of light emission, the detection of radiation, or the catalytic ability of the label.

In one measurement technique, the label on the second polynucleotide is biotin. The presence of this label can be detected by reacting it with the enzymes peroxidase or alkaline phosphatase. These enzymes can be specifically directed to biotin by conjugation with avidin or streptavidin. The presence of the enzymes is then detected by the addition of an appropriate substrate to provide a detectable color-developing or light-emitting reaction. Alkaline phosphatase-labeled streptavidin can be read fly obtained from the commercial market. A preferred substrate for alkaline phosphatase is adamantyl-1,2-dioxetane phosphate (AMPPD). Upon reaction with the alkaline phosphatase, AMPPD will emit light at a wavelength of 447 nm. This light can be detected in accordance with techniques known in the art.

In the reaction between alkaline phosphatase and AMPPD, an enhancer such as 5-N-tetradecanoyl-amino-fluorescein can be added. 5-N-tetradecanoyl-amino-fluorescein has the ability to convert light of 477 nm wavelength to light of 530 nm wavelength, which is more readily detectable.

Other labels include an antigen, such as digoxigenin or an antibody. An antigen can be detected by its ability to bind to an antibody directed thereto. Such antibodies, or an antibody directly used to label the second polynucleotide probe, can be detected by their ability to bind a protein. The antibody itself can be labeled directly with a radionuclide, such as $^{125}I$, or can be labeled by binding thereto a protein labeled with the radionuclide. The radionuclide can then be detected in accordance with techniques well known in the art, such as using X-ray film or a radiation counter.

Well-known techniques for the detection of a label include detecting a label in a color-developing reaction with a spectrophotometer. For example, fluorescein, which gives off a fluorescent pigment, can be used as a label. The use of such color-developing reactions are preferred in the present methods because the problems associated with using radioactive nuclides are thereby avoided.

Other such techniques include the detection of a light emitting reaction using X-ray film or an instant camera. The emission reactions are recorded by X-ray film or instant camera film in the dark room. The X-ray film which is exposed by emission reactions is recorded as a blot, so that the shading of the blot can be measured by a densitometer. If one uses an instant camera such as a Polaroid, the picture is read by a scanner to decide the location of the blot on the computer, and the shading of the blot is determined using graphic analysis software.

Figure 2:
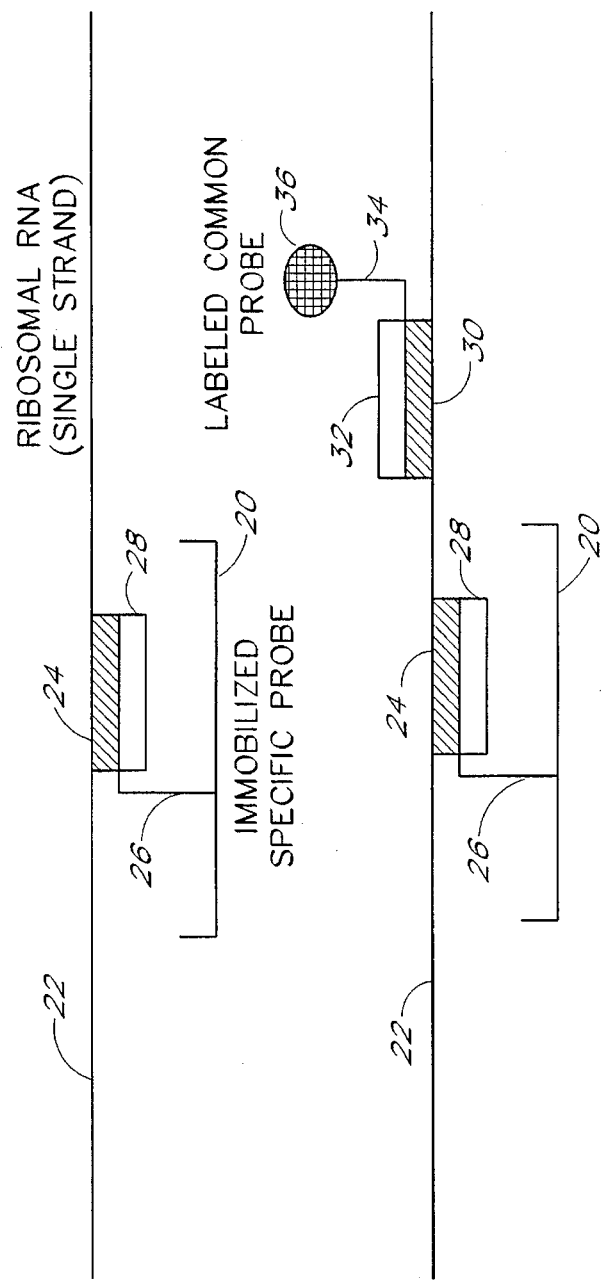
FIG. 2 is a schematic representation of the common and specific sequences identified in various species of fungi.
Figure 2:
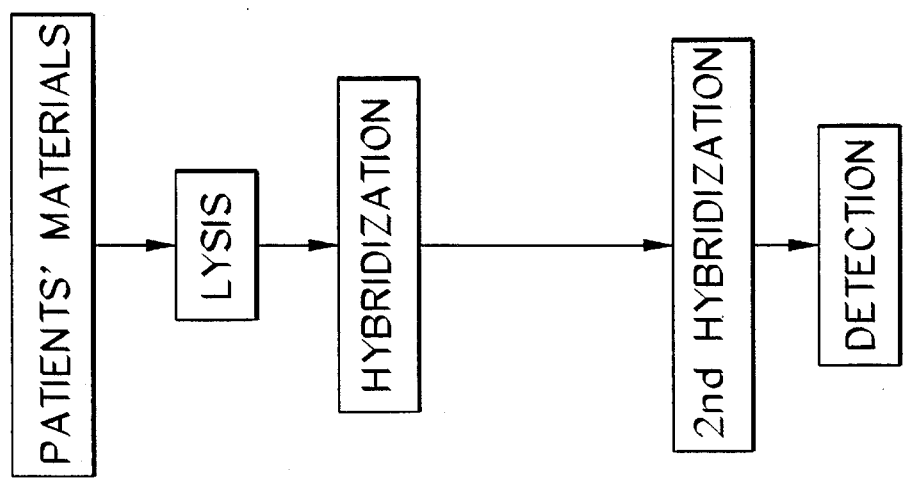

An example of the foregoing embodiment of the present invention is illustrated in FIG. 2. As shown in that Figure, following the collection and lysis of a sample of materials from a human patient, the ribosomal RNA of the species of fungus sought to be detected is hybridized. Following hybridization, a specific sequence 24 of the strand of ribosomal RNA 22 is annealed to a complementary sequence 28 on a first polynucleotide probe 26. The first probe 26 is immobilized on a solid support 20.

After removing substantially all of the unhybridized remains of the patient's materials, a second polynucleotide probe 34 is hybridized to the strand of ribosomal RNA 22 at a different sequence 30, which is preferably one that is common to a plurality of fungal species. The second probe 34 contains a sequence 32 that is complementary to the sequence 30. The second probe, in this diagram, also comprises a label 36 attached to the probe which facilitates the detection of the complex formed by the first probe 26, the second probe 34, the strand of ribosomal RNA 22, and the solid support 20.

Example 6 shows one method of measuring the amount of rRNA of a particular fungal species using a labeled common polynucleotide probe.

EXAMPLE 6

Measurement of Chemical Activities of the Labeled Second Nucleotide Probe

Following the hybridization described in Example 5, the hybridization solution (Lysis Buffer containing the labeled second polynucleotide probe) is removed by aspiration and the microtiter plate is washed once with 250 µl of fresh Lysis Buffer. A blocking buffer consisting of 0.05% (w/v) Tween 20, 500 mM NaCl, and 100 mM Tris-HCl, pH 7.5 is added into each well and incubated at room temperature for five minutes to reduced nonspecific binding. These solutions are then removed by aspiration.

The fluorescein on the second polynucleotide probe which is bound to the ribosomal RNA of the species of fungus being tested for, if present, is then visually detected to determine whether a fungus of that species was present in the biological sample. The approximate quantity of fungus present in the sample is then measured by determining the amount of fluorescein bound to the microtiter plate with a spectrophotometer or in a fluorimeter.

Using PCR to Detect Small Quantities of Fungus

Figure 3:
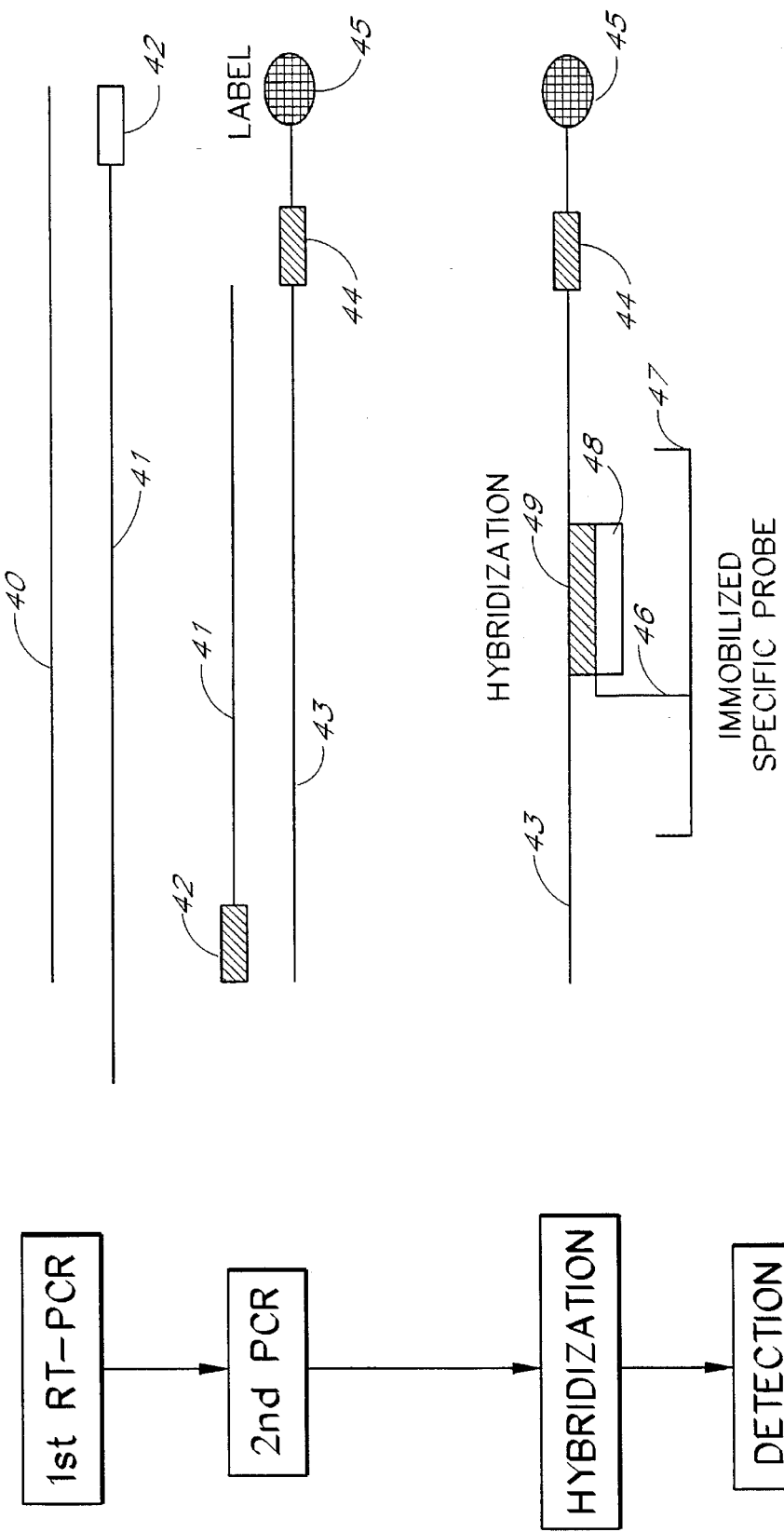
FIG. 3 is schematic representation of an embodiment of the method of the present invention in which PCR is used.

We have also discovered an alternative procedure which is especially useful in the detection of minute quantities of fungi in a sample. A preferred embodiment of this alternative procedure is schematically shown in FIG. 3. This alternative procedure makes use of a polymerase chain reaction (PCR) procedure to create multiple copies of a polynucleotide strand which is homologous to a strand of fungal ribosomal RNA. In this way, the number of polynucleotide strands in the sample that contain a polynucleotide sequence specific to the species of fungus being tested for can be amplified.

In the preferred embodiment shown in FIG. 3, a biological sample is first obtained as described previously. The sample is lysed so that the ribosomal RNA of any fungi present in the sample can be probed, and the lysed sample is contacted with a PCR primer 42. This primer 42 is complementary to a sequence of the ribosomal RNA of the fungal species to be detected in the sample. The primer 42 is then contacted with a ribosomal RNA strand 40 or a strand of cDNA 43 homologous to such ribosomal RNA and annealed to that strand. The annealing of the primer 42 can be accomplished in the same manner as was previously described in relation to the annealing of polynucleotide probes.

The primer 42 can comprise a sequence specific to the ribosomal RNA of the species of fungus. However, in a preferred embodiment, this primer can comprise any sequence located 5' to the specific sequence, so that the specific sequence is then incorporated when the primer 42 is extended. Preferably, when the primer 42 of the preferred embodiment is used, this primer has a sequence complementary to a sequence common to a plurality of fungal species. Thus, this primer can be referred to as a first common PCR primer 42.

After the first common PCR primer 42 has been annealed to the ribosomal RNA, this primer is extended using the four nucleotide triphosphates and a polymerase enzyme, thereby producing a double-stranded polynucleotide including a complementary strand having a sequence complementary to the ribosomal RNA. Preferably, the polymerase is a reverse transcriptase and the nucleotide triphosphates are deoxynucleotide triphosphates (dNTP's) so that cDNA to the rRNA is produced. Further rounds of amplification can be accomplished by reannealing additional primer 42 to the strand of ribosomal RNA 40 and then extending that primer.

Amplification can preferably be accomplished, though, by annealing to the strand of cDNA 41 a second PCR primer 44 that is complementary to the newly synthesized cDNA strand 41. Thus, this second primer 44 is homologous to a portion of the rRNA strand 40. This second primer 44 is also preferably common to the rRNA of a plurality of species such that the reaction will continue without regard to the species of origin of the ribosomal RNA in the sample. Thus, in a preferred embodiment, the second primer 44 is a second common PCR primer, and the ribosomal RNA of a plurality of species can be amplified with it. Amplification is completed then by extending the second primer 44 to produce a strand of cDNA 43 that is homologous to at least a portion of the fungal ribosomal RNA in a sample.

These later rounds of amplification preferably use the four dNTP's in combination with a DNA polymerase so that double-stranded DNA is amplified which contains one strand of cDNA 43 homologous to the fungal ribosomal RNA 40 present in the biological sample and one strand of cDNA 41 complementary to the fungal ribosomal RNA. Preferably, approximately 20 to 40 cycles of DNA synthesis are performed in order to produce an adequate amount of cDNA homologous to the rRNA present in the sample for later detection. A DNA polymerase is used in the synthesis of such cDNA. This polymerase preferably has significant polymerase activity at temperatures above 50° C., such as Taq DNA polymerase.

Following these rounds of amplification, preferably using the common primers, another round of amplification using specific primers is performed. Each of the two primers used in this later round is homologous either to the strand of cDNA created in the initial round of amplification that is homologous to the ribosomal RNA in the sample or to the strand that is complementary to such ribosomal RNA. At least one, and preferably both of, these specific primers contain a sequence that is specific to the fungal species or genus to be detected. It can be seen, therefore, that when PCR is performed using the foregoing primers, amplification will occur in significant amounts only if the rRNA of the species being tested for is present in the biological sample and the initial amplification has produced cDNA corresponding to such rRNA.

The amplification of the specific sequences contained in the rRNA of a specific species of fungus or in a polynucleotide strand complementary to such rRNA can be detected in several ways, as will be appreciated by those having ordinary skill in the art. For example, the primer itself can be labeled and the presence of the label in an extended polynucleotide can be detected. As shown in FIG. 3, for example, a label 45 can be attached to the primer 44, which is then extended to produce the homologous polynucleotide 43.

The homologous polynucleotide strand 43 can then be contacted with and hybridized to a sequence 48 complementary to a specific sequence 40 on a specific polynucleotide probe 46 which is immobilized on a solid support 47, as in other embodiments of the present invention. Following this, the unhybridized portions of the sample and any synthesized polynucleotides are preferably washed from the solid support 47, and the labeled homologous polynucleotide 43 immobilized on the solid support 47 is detected. Alternatively, following the washing of the solid support 47, a second polynucleotide probe (not shown in FIG. 3) carrying a label can be hybridized to the homologous strand 43. This can also be followed by washing. After washing unhybridized second probe from the solid support, the labeled second probe can be detected using any of a variety of techniques. For example, the homologous polynucleotide 43 can be detected as described previously in relation to the detection of the second polynucleotide probe of the foregoing embodiment of the method of the present invention. The homologous polynucleotide 43 will only be detected, of course, if it is hybridized to the immobilized probe 46. In order for the homologous polynucleotide to hybridize, the primer 44 generally should have been extended far enough so that the specific sequence 49 is synthesized and is therefore available to anneal to the probe 46.

In an another examplary method of detecting the presence of the rRNA of the species of interest, the complementary cDNA strand 41 rather than the homologous polynucleotide 43 can be annealed to a probe 46 immobilized on the solid support. In this method, the primer 42 is labeled rather than the primer 44. The primer 42 can be detected directly, such as through electrophoresis. Alternatively, a specific probe 46 homologous to a sequence specific to the particular species of fungus can be used to anneal the strand containing the labeled probe to a solid support. This can be detected as described above.

Example 7 illustrates one method of identifying small quantities of *Pneumocystis carinii* in a sample.

EXAMPLE 7

Amplifying Ribosomal RNA Present in Minute Quantities with PCR

A sputum sample from a patient suspected of having pneumonia caused by the fungus *Pneumocystis carinii* is first lysed with Lysis Buffer and brought to a total volume of sample and lysis buffer of 50 μl. This mixture is then added to a well of a microtiter plate to which a common probe (SEQ ID NO:1) has been immobilized, thereby contacting the probe with the mixture. The common probe is a polydeoxynucleotide complementary to a sequence common to the ribosomal RNA of a number of fungal species. The sequence on the ribosomal RNA of *Pneumocystis carinii* to which it is complementary is located 3' of a specific sequence (SEQ ID NO:81) of such ribosomal RNA.

The common probe can then be hybridized to the fungal ribosomal RNA in the sample by incubating the mixture in the well at 39° C. for one hour and then cooling the mixture over 20–30 minutes. Following the annealing of the common probe to the ribosomal RNA, the probe is extended with a reverse transcriptase to produce a cDNA strand having a sequence complementary to the ribosomal RNA. The complementary strand is then melted off of the ribosomal RNA by heating the mixture to 94° C. for 1 to 2 minutes. This process is repeated several times in order to amplify the number of complementary strands.

Following the denaturation of the complementary strand from the ribosomal RNA, a second primer homologous to a sequence of the ribosomal RNA that is specific to *Pneumocystis carinii* is added to the mixture. The four dNTP's and a DNA polymerase capable of polymerase activity above 50° C. is added to the mixture. The mixture is then heated to a temperature below the $T_m$ of the second primer but high enough to assure specific binding of the primer, in this case approximately 50° C. After allowing enough time for the second primer to be extended, about 1–2 minutes, the mixture is heated to 94° C. for 1 to 2 minutes to melt the newly synthesized strand homologous to the ribosomal RNA of the sample from the complementary strand. This process is repeated from between 20–40 times, with the addition of primer as necessary.

Following this round of amplification, two labeled, specific primers are added to the mixture. One is complementary to a specific sequence on complementary strand, while the other is complementary to a sequence on the homologous strand. After annealing such primers to the complementary and homologous strands, these primers are extended with a polymerase in the same fashion as the second primer, after which such strands are melted off by raising the temperature of the mixture to 94° C. for 1 to 2 minutes. This process is also repeated between 20–40 times.

After the final round of amplification, the mixture is heated to melt off any newly synthesized strands from the templates from which they were produced, and the mixture is cooled to 37° C. and incubated at that temperature for an hour in order to allow the strands present in the mixture to anneal to a specific probe immobilized on the microtiter well. This probe is complementary to a specific sequence in the ribosomal RNA of *Pneumocystis carinii* and anneals to the ribosomal RNA of that fungus in addition to the synthesized sequences homologous to such ribosomal RNA.

Once the polynucleotide strands in the mixture have been allowed to hybridize to the specific probe, the non-hybridized portions of the mixture are removed by aspiration. The walls of the microtiter plate are then washed with Lysis Buffer to remove any non-specifically bound nucleotide strands from the well. The label attached to the specific primer is next detected in order to detect the presence of *Pneumocystis carinii* in the biological sample. If the label is detected, this indicates that the biological sample contained this fungus.

Fungal Detection Kits

In one embodiment, the present invention comprises a kit for identifying the presence of a particular species of fungus in a biological sample. Such a kit includes at least one specific polynucleotide probe and a common probe, as described above. In a preferred embodiment, a plurality of specific probes are included, and such probes are preferably immobilized on one or more solid supports. In a more preferred embodiment, each of the plurality of specific probes is immobilized on a different solid support. For example, a microtiter plate having a plurality of wells can have a different polynucleotide probe immobilized to each well. If such probes contain sequences specific to the ribosomal RNA of different species of fungi, the kit can be used to test a single biological sample for the presence of a plurality of fungi.

Figure 4:
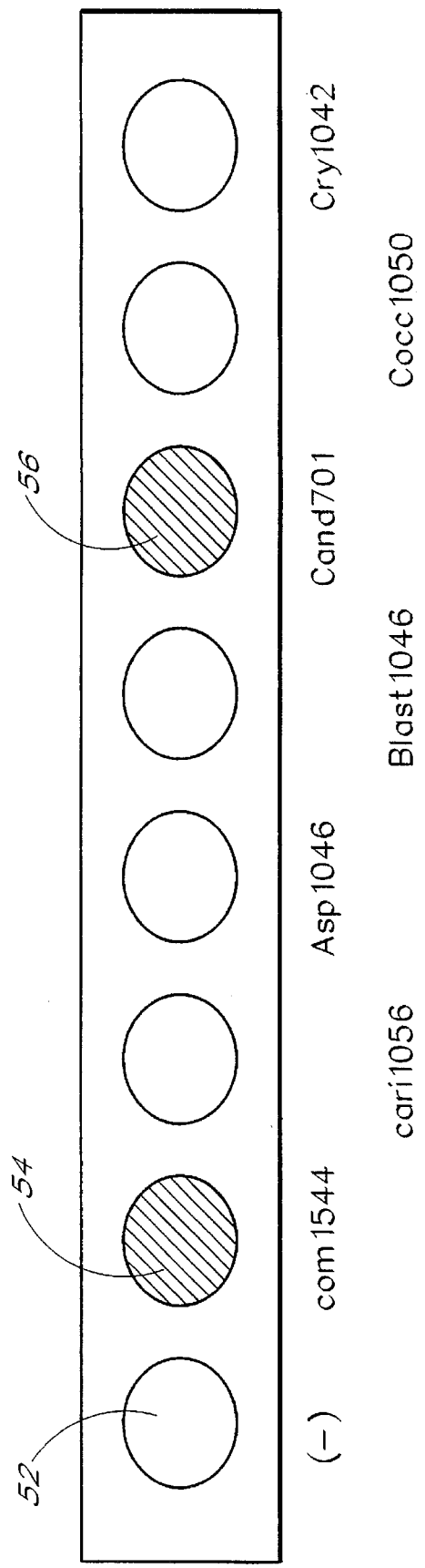
FIG. 4 is a schematic representation of an example of a microtiter plate used in the methods of the present invention.

An example of such a kit using microtiter wells as the solid supports is shown schematically in FIG. 4. In this figure, the presence of the ribosomal RNA of a particular species of fungus, in this case *Candida albicans*, is detected in a well 56, which is darkened to show a positive result. No probe has been immobilized to well 52 in order to provide a negative control. Well 54, on the other hand, has immobilized to its walls a common probe, such as SEQ ID NO:1, which is complementary to a sequence present in the ribosomal RNA of the fungi being tested for. This provides a positive control, since well 54 should show a positive result whenever a positive result is detected in well 56 or any of the other wells in this embodiment of the kit.

Well 54 also provides a means of detecting the presence of fungi which do not contain the specific ribosomal RNA sequences being probed by the specific polynucleotide probes. For example, if a mutant strain of *Candida albicans* which does not contain the specific sequence complementary to the probe used in well 56 is present in a sample tested with the kit illustrated in FIG. 4, well 56 would not show a positive result. Well 54 would, however, indicate the presence of a fungal pathogen, as long as the mutant strain did not contain a mutation in the common sequence detected in well 54 which interfered with the hybridization of that sequence to the common probe immobilized to the walls of well 54.

Other elements can also be included in the present kit. For example, appropriate buffers for hybridizing fungal ribosomal RNA to the probes in the kit can be included. Labels, as described above, can also be incorporated which are attached to a common probe.

The forgoing embodiments of the kit of the present invention can be adapted to perform the methods of the present invention that involve PCR as well. In this embodiment, the kit additionally includes a reverse transcriptase and a polymerase, preferably a DNA polymerase that has significant polymerase activity at temperatures above 50° C., such as Taq DNA polymerase.

Conclusion

All references cited herein are hereby explicitly incorporated by this reference thereto.

The invention has been described with reference to certain particular exemplary embodiments of various aspects. However, these embodiments are intended only to illustrate, rather than to limit the present invention. Accordingly, the scope of the present invention is to be determined upon reference to the appended claims.

TABLE I

| | Common probe (Com-392)* for Fungi | |
|---|---|---|
| Species | GenBank name | Com-392 GAGGGAGCCTGAGAAACG |
| I. Fungi | | |
| Pneumocystis carinii | PMC16SRR1 | ------------------ |
| Cryptococcus neoformans | CPCDA | ------------------ |
| Coccidiodes immitis | COIDA | ------------------ |
| Blastomyces dermatitidis | BLODA | ------------------ |
| Aspergillus fumagatus | ASNDA | ------------------ |
| fumigatus | ASNRR5SS | ------------------ |
| fumigatus | ASNRRSSB | ------------------ |
| Candida albicans | YSASRSUA | ------------------ |
| albicans | YSAL16S | ------------------ |
| lusitaniae | YSASRRNAA | ------------------ |
| lusitaniae | YSASRSUE | ------------------ |
| kefyr | YSASRSUB | ------------------ |
| krusei | YSASRRNAC | ------------------ |
| krusei | YSASRSUD | ------------------ |
| tropicalis | YSASRRNAB | ------------------ |
| tropicalis | YSASRSUG | ------------------ |
| viswanathii | YSASRSUH | ------------------ |
| parapsilosis | YSASRSUF | ------------------ |
| guilliermondii | YSASRSUC | ------------------ |
| glabrata | YS5CRRNAS | ------------------ |

*Com-392 is identical among 107 different rRNAs registered in GenBank

TABLE II

| | Common probe (Com-419)* for Fungi | |
|---|---|---|
| Species | GenBank name | Com-419 TCCAAGGAAGGCAGCAGG |
| I. Fungi | | |
| Pneumocystis carinii | PMC16SRR1 | ------------------ |
| Cryptococcus neoformans | CPCDA | ------------------ |
| Coccidiodes immitis | COIDA | ------------------ |
| Blastomyces dermatitidis | BLODA | ------------------ |
| Aspergillus fumagatus | ASNDA | ------------------ |
| fumigatus | ASNRR5SS | ------------------ |
| fumigatus | ASNRRSSB | ------------------ |
| Candida albicans | YSASRSUA | ------------------ |
| albicans | YSAL16S | ------------------ |
| lusitaniae | YSASRRNAA | ------------------ |
| lusitaniae | YSASRSUE | ------------------ |
| kefyr | YSASRSUB | ------------------ |
| krusei | YSASRRNAC | ------------------ |
| krusei | YSASRSUD | ------------------ |
| tropicalis | YSASRRNAB | ------------------ |
| tropicalis | YSASRSUG | ------------------ |
| viswanathii | YSASRSUH | ------------------ |

TABLE II-continued

Common probe (Com-419)* for Fungi

| Species | GenBank name | Com-419 TCCAAGGAAGGCAGCAGG |
|---|---|---|
| parapsilosis | YSASRSUF | ------------------ |
| guilliermondii | YSASRSUC | ------------------ |
| glabrata | YS5CRRNAS | ------------------ |

*Com-419 is identical among 123 different rRNAs registered in GenBank

TABLE III

Common probe (Com-1205)* for Fungi

| Species | GenBank name | Com-1205 ACGGGGAAACTCACCAGG |
|---|---|---|
| I. Fungi | | |
| Pneumocystis carinii | PMC16SRR1 | ------------------ |
| Cryptococcus neoformans | CPCDA | ------------------ |
| Coccidiodes immitis | COIDA | ------------------ |
| Blastomyces dermatitidis | BLODA | ------------------ |
| Aspergillus fumagatus | ASNDA | ------------------ |
| fumigatus | ASNRR5SS | ------------------ |
| fumigatus | ASNRRSSB | ------------------ |
| Candida albicans | YSASRSUA | ------------------ |
| albicans | YSAL16S | ------------------ |
| lusitaniae | YSASRRNAA | ------------------ |
| lusitaniae | YSASRSUE | ------------------ |
| kefyr | YSASRSUB | ------------------ |
| krusei | YSASRRNAC | ------------------ |
| krusei | YSASRSUD | ------------------ |
| tropicalis | YSASRRNAB | ------------------ |
| tropicalis | YSASRSUG | ------------------ |
| viswanathii | YSASRSUH | ------------------ |
| parapsilosis | YSASRSUF | ------------------ |
| guilliermondii | YSASRSUC | ------------------ |
| glabrata | YS5CRRNAS | ------------------ |

*Com-1205 is identical among 42 different rRNAs registered in GenBank

TABLE IV

Common probe (Com-1544)* for Fungi

| Species | GenBank name | Com-1544 TCGTGCTGGGGATAGAGC |
|---|---|---|
| I. Fungi | | |
| Pneumocystis carinii | PMC16SRR1 | ------------------ |
| Cryptococcus neoformans | CPCDA | ------------------ |
| Coccidiodes immitis | COIDA | ------------------ |
| Blastomyces dermatitidis | BLODA | ------------------ |
| Aspergillus fumagatus | ASNDA | ------------------ |
| fumigatus | ASNRR5SS | ------------------ |
| fumigatus | ASNRRSSB | ------------------ |
| Candida albicans | YSASRSUA | ------------------ |
| albicans | YSAL16S | ------------------ |
| lusitaniae | YSASRRNAA | ------------------ |
| lusitaniae | YSASRSUE | ------------------ |
| kefyr | YSASRSUB | ------------------ |
| krusei | YSASRRNAC | ------------------ |
| krusei | YSASRSUD | ------------------ |
| tropicalis | YSASRRNAB | ------------------ |
| tropicalis | YSASRSUG | ------------------ |
| viswanathii | YSASRSUH | ------------------ |
| parapsilosis | YSASRSUF | ------------------ |

TABLE IV-continued

Common probe (Com-1544)* for Fungi

| Species | GenBank name | Com-1544<br>TCGTGCTGGGGATAGAGC |
|---|---|---|
| guilliermondii | YSASRSUC | ------------------ |
| glabrata | YS5CRRNAS | ------------------ |

*Com-1544 is identical among 40 different rRNAs registered in GenBank

TABLE V

Probes for Pneumocystis carinii (Cari-685)

| Species | GenBank name | Cari-685<br>GCGCAACTGATCCTTCCC |
|---|---|---|
| I. Fungi | | |
| Pneumocystis carinii | PMC16SRR1 | ------------------ |
| Cryptococcus neoformans | CPCDA | -T--CGGC----G----AT |
| Coccidiodes immitis | COIDA | A-CTGGT-------G--A |
| Blastomyces dermatitidis | BLODA | A-CTGGT-------G--A |
| Aspergillus fumagatus | ASNDA | A-CTGGT-------G--A |
| fumigatus | ASNRR5SS | ----CGGC---GG---AT |
| fumigatus | ASNRRSSB | ----CGGC---GG---AT |
| Candida albicans | YSASRSUA | ------G-C---AGCTTG |
| albicans | YSAL16S | ------G-C---AGCTTG |
| lusitaniae | YSASRRNAA | ------G-C---AGCTTG |
| lusitaniae | YSASRSUE | ------G-C---AGCTTG |
| kefyr | YSASRSUB | ------G-C---AGCTTG |
| krusei | YSASRRNAC | ------G-C---AGCTTG |
| krusei | YSASRSUD | ------G-C---AGCTTG |
| tropicalis | YSASRRNAB | ------G-C---AGCTTG |
| tropicalis | YSASRSUG | ------G-C---AGCTTG |
| viswanathii | YSASRSUH | ------G-C---AGCTTG |
| parapsilosis | YSASRSUF | ------G-C---AGCTTG |
| guilliermondii | YSASRSUC | ------G-C---AGCTTG |
| glabrata | YS5CRRNAS | ------G-C---AGCTTG |
| II. Highest homologous sequence in GenBank | | |
| Human TAN-1 | HUMTAN1 | --------A-C-------- |
| Abccelsyn xylium | ABCCELSYN | -A-G-------------- |
| Human mRNA neuron | HUMNSEMRNA | CTC-C------------- |

TABLE VI

Probes for Pneumocystis Carinii (Cari-1056)

| Species | GenBank name | Cari-1056<br>GGCGATGTTTTTTTCTTGACTCG |
|---|---|---|
| I. Fungi | | |
| Pneumocystis carinii | PMC16SRR1 | ----------------------- |
| Cryptococcus neoformans | CPCDA | -------C=-CA---AAATA--T |
| Coccidiodes immitis | COIDA | -------C--CA---AAATA--T |
| Blastomyces dermatitidis | BLODA | -------C--CA---AAATA--T |
| Aspergillus fumagatus | ASNDA | ----G-----C-A-GA-----C-- |
| fumigatus | ASNRR5SS | ----G-----C-A-GA----C-- |
| fumigatus | ASNRRSSB | ----G-----C-A-GA----C-- |
| Candida albicans | YSASRSUA | -TT-T----C----A------G-A |
| albicans | YSAL16S | -TT-T----C----A------G-A |
| lusitaniae | YSASRRNAA | ----GC---CA---AG----G-- |
| lusitaniae | YSASRSUE | ----GC---CA---AG----G-- |
| kefyr | YSASRSUB | -------G--CA---AAATTCT |
| krusei | YSASRRNAC | ---CG-T---AG-C----GAGTG |
| krusei | YSASRSUD | TATTT----NG-----A-GACCA |
| tropicalis | YSASRRNAB | -TT-T----C----A------G-A |
| tropicalis | YSASRSUG | -TT-T----C----A------G-A |
| viswanathii | YSASRSUH | -TT-T----C----A------G-A |

TABLE VI-continued

Probes for Pneumocystis Carinii (Cari-1056)

| Species | GenBank name | Cari-1056<br>GGCGATGTTTTTTTCTTGACTCG |
|---|---|---|
| parapsilosis | YSASRSUF | −TT−T−−−−C−−−−A−−−−−G−A |
| guilliermondii | YSASRSUC | −−T−T−−−−C−K−−T−−−−−G−A |
| glabrata | YS5CRRNAS | −−T−G−−−−−−−−−AG−−−−C−A |
| II. Highest homologous sequence in GenBank | | |
| Tobacco chloroplast | TOBCPTGRG | C−A−CC−−−−−−−−−−−−−−−− |
| Aureobasidium pullulans | AURRR16S | −−−−−−−−−A−CA−T−−−−−−−− |
| N.tabacum | TOBCOCG | C−A−CC−−−−−−−−−−−−−−−− |

TABLE VII

Probes for Aspergillus (Asp-693)

| Species | GenBank name | Asp-693<br>CTTCTGGGGAACCTCATGG |
|---|---|---|
| I. Fungi | | |
| Pneumocystis carinii | PMC16SRR1 | AACAC−−−−−−A−−−−CCA |
| Cryptococcus neoformans | CPCDA | AACAC−−−−−−A−−−−CCA |
| Coccidiodes immitis | COIDA | −−−−−−−−−−−−−CT−−−− |
| Blastomyces dermatitidis | BLODA | −−C−−−−−A−G−−C−−−−− |
| Aspergillus fumagatus | ASNDA | −−−−−−−−−−−−−−−−−− |
| fumigatus | ASNRR5SS | −−−−−−−−−−−−−−−−−− |
| fumigatus | ASNRRSSB | −−−−−−−−−−−−−−−−−− |
| Candida albicans | YSASRSUA | AAAGG−−−C−−−−−−−−TC |
| albicans | YSAL16S | AACAC−−−−−−A−−−−CCA |
| lusitaniae | YSASRRNAA | AA−−−T−−−−−−A−−−−CGTC |
| lusitaniae | YSASRSUE | AA−−−T−−−−−A−−−−CGTC |
| kefyr | YSASRSUB | −−−−−−−CT−−−−−GTACT |
| krusei | YSASRRNAC | AACAC−−−−−−A−−−−CCA |
| krusei | YSASRSUD | −−−−−−−CT−S−−−−GG−C |
| tropicalis | YSASRRNAB | −−−−−−−CT−G−−−TT−−− |
| tropicalis | YSASRSUG | −−−−−−−CT−G−−−TT−−− |
| viswanathii | YSASRSUH | −−−−−−−CT−G−−−TT−−− |
| parapsilosis | YSASRSUF | AACAC−−−−−−A−−−−CCA |
| guilliermondii | YSASRSUC | −−−−−−−CT−−−−ATTC−C |
| glabrata | YS5CRRNAS | −−−−−−−CT−−−−C−−A−T |
| II. Highest homologous sequence in GenBank | | |
| Penniclium notatum sub | PNNDA | −−−−−−−−−−−−−−−−−− |
| Human HLA-B-AT3 | HUMBAT3A | −−−−−−−−−−−−−GC−A− |
| Rat olfactory protein | RATOLFPRON | −−C−−−−−−−−−−−−−CA |

TABLE VIII

Probes for Aspergillus (Asp-1046)

| Species | Genbank name | Asp-1046<br>GGCGGTGTTTCTATGATGACC |
|---|---|---|
| I. Fungi | | |
| Pneumocystis carinii | PMC16SRR1 | −−−−A−−−−−T−T−CT−−−−T |
| Cryptococcus neoformans | CPCDA | TTGTTG−−−−−−−G−−−CG−− |
| Coccidiodes immitis | COIDA | ACGT−−−G−−−−−−TT−−TTG |
| Blastomyces dermatitidis | BLODA | −A−−−G−−−CT−−−−−−−−−− |
| Aspergillus fumagatus | ASNDA | −−−−−−−−−−−−−−−−−−−− |
| fumigatus | ASNRR5SS | −−−−−−−−−−−−−−−−−−−− |
| fumigatus | ASNRRSSB | −−−−−−−−−−−−−−−−−−−− |
| Candida albicans | YSASRSUA | CCTTCG−GC−−−T−−−−−−TT |
| albicans | YSAL16S | CCTTCG−GC−−−T−−−−−−TT |
| lusitaniae | YSASRRNAA | −−−−−C−−−CA−T−AG−−−−G |
| lusitaniae | YSASRSUE | −−−−−C−−−CA−T−AG−−−−G |
| kefyr | YSASRSUB | −−T−−−−−−−−T−C−T−−−−−− |

TABLE VIII-continued

Probes for Aspergillus (Asp-1046)

| Species | Genbank name | Asp-1046<br>GGCGGTGTTTCTATGATGACC |
|---|---|---|
| krusei | YSASRRNAC | -A----C-AC-----G-A-G- |
| krusei | YSASRSUD | -A----C-AC-----G-A-G- |
| tropicalis | YSASRRNAB | TCTTCG-AC---T------TT |
| tropicalis | YSASRSUG | TCTTCG-AC---T------TT |
| viswanathii | YSASRSUH | CCTTCG-GC---T------TT |
| parapsilosis | YSASRSUF | ----A--G---AT-C-AATTT |
| guilliermondii | YSASRSUC | TCTTTGAGC---T------TT |
| glabrata | YS5CRRNAS | --T-------T-T-AG----- |

II. Highest homologous sequence in GenBank

| | | |
|---|---|---|
| Nanochlorum eucaryotum | NANRRN18S | -CG-------T-T--------- |
| Moraxella sp. MspI | MBOMSPI | TCTA-------A---------T |
| E. coli cvaA,B operon | ECOCVAB | -T--------G-G------TG |

TABLE IX

Probes for Blastomyces (Blast-694)

| Species | GenBank name | Blast-694<br>TCCTGGGAAGCCCCATG |
|---|---|---|
| I. Fungi | | |
| Pneumocystis carinii | PMC16SRR1 | GT---T--T----TTA- |
| Cryptococcus neoformans | CPCDA | -G---AA-------GAC |
| Coccidiodes immitis | COIDA | -T-----G-A---T--- |
| Blastomyces dermatitidis | BLODA | ----------------- |
| Aspergillus fumagatus | ASNDA | -T-----G-A--T---- |
| fumigatus | ASNRR5SS | -T-----G-A--T---- |
| fumigatus | ASNRRSSB | -T-----G-A--T---- |
| Candida albicans | YSASRSUA | -T-----T----ATT-A |
| albicans | YSAL16S | GT---T--T----TTA- |
| lusitaniae | YSASRRNAA | GT---T--T----TTA- |
| lusitaniae | YSASRSUE | GT---T--T----TTA- |
| kefyr | YSASRSUB | GT---T--T----TTA- |
| krusei | YSASRRNAC | GT---T--T----TTA- |
| krusei | YSASRSUD | GT---T--T----TTA- |
| tropicalis | YSASRRNAB | GT---T--T----TTA- |
| tropicalis | YSASRSUG | GT---T--T----TTA- |
| viswanathii | YSASRSUH | GT---T--T----TTA- |
| parapsilosis | YSASRSUF | GT---T--T----TTA- |
| guilliermondii | YSASRSUC | GT---T--T----TTA- |
| glabrata | YS5CRRNAS | G------T----GGTCC |

II. Highest homologous sequence in GenBank

| | | |
|---|---|---|
| Avian influenza | FLAHA5 | ---------A------- |
| Mouse perlecan | MUSPERPA | ------C--G------ |
| Mouse basement membrane | MUSPGCBMA | -------C--G------ |

TABLE X

Probes for Blastomyces (Blast-1046)

| Species | GenBank name | Blast-1046<br>GACGGGGTTCTTATGATGACC |
|---|---|---|
| I. Fungi | | |
| Pneumocystis carinii | PMC16SRR1 | CG----C------GAGG---T |
| Cryptococcus neoformans | CPCDA | -GT-AAA------GAT----G |
| Coccidiodes immitis | COIDA | ------CAA---TGA--A--- |
| Blastomyces dermatitidis | BLODA | --------------------- |
| Aspergillus fumagatus | ASNDA | -G---T---TC---------- |
| fumigatus | ASNRR5SS | -G---T---TC---------- |
| fumigatus | ASNRRSSB | -G---T---TC---------- |

TABLE X-continued

Probes for Blastomyces (Blast-1046)

| Species | GenBank name | Blast-1046<br>GACGGGGTTCTTATGATGACC |
|---|---|---|
| Candida albicans | YSASRSUA | -TT-TT------T-AT----G |
| albicans | YSAL16S | -TT-TT------T-AT----G |
| lusitaniae | YSASRRNAA | -G---C----A-T-AG----G |
| lusitaniae | YSASRSUE | -G---C----A-T-AG----G |
| kefyr | YSASRSUB | -GT--T---T--C-T------ |
| krusei | YSASRRNAC | -----TC-A-C----G-A-G- |
| krusei | YSASRSUD | -----TC-A-C----G-A-G- |
| tropicalis | YSASRRNAB | -TT-TT------T-AT----G |
| tropicalis | YSASRSUG | -TT-TT------T-AT----G |
| viswanathii | YSASRSUH | -TT-TT------T-AT----G |
| parapsilosis | YSASRSUF | -TT-TT------T-AT----G |
| guilliermondii | YSASRSUC | -GT-TT-----KT-TT----G |
| glabrata | YS5CRRNAS | -GT--T---T--T-AG----- |
| II. Highest homologous sequence in GenBank | | |
| Rat ITPR2 Type2inositol | RATITPR2R | ----------CC-CT------ |
| Canine mRNA | DOGSRPR | CTGCTAA-------------- |
| Mitochondrion Oenothera | OBEMTNAD12 | C-GTCTT-------------- |

TABLE XI

Probes for Candida (Cand-513)

| Species | GenBank name | Cand-513<br>GAGTACAATGTAAATACCTTAACGAG |
|---|---|---|
| I. Fungi | | |
| Pneumocystis carinii | PMC16SRR1 | ----------T--G-------------- |
| Cryptococcus neoformans | CPCDA | ---------T-----C------------ |
| Coccidiodes immitis | COIDA | ---------T-----C------------ |
| Blastomyces dermatitidis | BLODA | ---------C-----C------------ |
| Aspergillus fumagatus | ASNDA | ---------C-----C------------ |
| fumigatus | ASNRR5SS | ---------C-----C------------ |
| fumigatus | ASNRRSSB | ---------C-----C------------ |
| Candida albicans | YSASRSUA | ---------------------------- |
| albicans | YSAL16S | ---------------------------- |
| lusitaniae | YSASRRNAA | ---------------------------- |
| lusitaniae | YSASRSUE | ---------------------------- |
| kefyr | YSASRSUB | ---------------------------- |
| krusei | YSASRRNAC | ---------------------------- |
| krusei | YSASRSUD | ---------------------------- |
| tropicalis | YSASRRNAB | ---------------------------- |
| tropicalis | YSASRSUG | ---------------------------- |
| viswanathii | YSASRSUH | ---------------------------- |
| parapsilosis | YSASRSUF | ---------------------------- |
| guilliermondii | YSASRSUC | ---------------------------- |
| glabrata | YS5CRRNAS | ---------------------------- |
| II. Highest homologous sequence in GenBank | | |
| Yeast 18S rRNA | YSCRNA5 | ---------------------------- |
| Yeast (S. cerevisiae) | YSCRGEA | ---------------------------- |
| Kluyveromyces lactis | YSK17SRRNA | ---------------------------- |
| Torulaspora delbrueckii | TOUSRSR | ---------------------------- |
| T. glabrata rRNA | YSLSRSUA | ---------------------------- |
| H. polymorpha rRNA | HASSRSUA | ---------------------------- |
| S. pombe rRNA | YSPRRNASS | ---------------------------- |

TABLE XII

Probes for Candida (Cand-701)

| Species | GenBank name | Cand-701<br>GGTAGCCATTTATGGCGAACC |
|---|---|---|
| I. Fungi | | |
| Pneumocystis carinii | PMC16SRR1 | TTA------GC---T-T--GT |
| Cryptococcus neoformans | CPCDA | TTCG---C-C-----T---T- |
| Coccidiodes immitis | COIDA | TTA------GC---T-T--GT |
| Blastomyces dermatitidis | BLODA | TTA------GC---T-T--GT |
| Aspergillus fumagatus | ASNDA | ATA---A------ACG-TGAA |
| fumigatus | ASNRR5SS | ATA---A------ACG-TGAA |
| fumigatus | ASNRRSSB | ATA---A------ACG-TGAA |
| Candida albicans | YSASRSUA | --------------------- |
| albicans | YSAL16S | --------------------- |
| lusitaniae | YSASRRNAA | TTA------GC---T-T--GT |
| lusitaniae | YSASRSUE | -C-----TNG-C-----CG-N |
| kefyr | YSASRSUB | -C----NC--GC---TTN--T |
| krusei | YSASRRNAC | C--TTT----A--CAA----G |
| krusei | YSASRSUD | TTA------GC---T-T--GT |
| tropicalis | YSASRRNAB | -C----- --T--------- |
| tropicalis | YSASRSUG | -C----- --T--------- |
| viswanathii | YSASRSUH | -C----- --T--------- |
| parapsilosis | YSASRSUF | -C----- ---T-------- |
| guilliermondii | YSASRSUC | ---CCG-C---T------GTA |
| glabrata | YS5CRRNAS | ATA---A------ACA-TGAA |
| II. Highest homologous sequence in GenBank | | |
| S. enterica | STYRFB | -------G---------CGCTT |
| Clostridium pasterianum | CLONIFH5 | --------T-----------AA----GG |
| C. pasteurianum nifH | CLONIFH | ---------T-----------AA----GG |
| C. pasteurianum nifH | CLONIFH1 | --------T-----------AA----GG |

TABLE XIII

Probes for Coccidiodes (Cocc-659)

| Species | GenBank name | Cocc-659<br>CTTCGCGGCGTGCACTG |
|---|---|---|
| I. Fungi | | |
| Pneumocystis carinii | PMC16SRR1 | ---------ATC---TG- |
| Cryptococcus neoformans | CPCDA | -C--A---A-------- |
| Coccidiodes immitis | COIDA | ------------------ |
| Blastomyces dermatitidis | BLODA | -C--A-C---------- |
| Aspergillus fumagatus | ASNDA | -C--AT---C-T------ |
| fumigatus | ASNRR5SS | -C--AT---C-T------ |
| fumigatus | ASNRRSSB | -C--AT---C-T------ |
| Candida albicans | YSASRSUA | GCA----CGC-A----- |
| albicans | YSAL16S | GCA----CGC-A----- |
| lusitaniae | YSASRRNAA | -GCTTA----A------ |
| lusitaniae | YSASRSUE | TNGTCT----C--N--T |
| kefyr | YSASRSUB | GCA----CGC-A----- |
| krusei | YSASRRNAC | GCA----CGC-A----- |
| krusei | YSASRSUD | GCA----CGC-A----- |
| tropicalis | YSASRRNAB | GCA----CGC-A----- |
| tropicalis | YSASRSUG | GCA----CGC-A----- |
| viswanathii | YSASRSUH | GCA----CGC-A----- |
| parapsilosis | YSASRSUF | GCA----CGC-A----- |
| guilliermondii | YSASRSUC | ---TTT----A-T---- |
| glabrata | YS5CRRNAS | ---G------AA-CAG- |
| II. Highest homologous sequence in GenBank | | |
| Rabbit progest. recep. | RABPRG1 | ------A---------G- |
| Streptomyces lividans 66 | STMTRNGM | ------C---------GA |
| Human mRNA cysteine | HUMCYSTCR | G-GT-------------- |

TABLE XIV

Probes for Coccidiodes (Cocc-1050)

| Species | GenBank name | Cocc-1050<br>GGCAACTTTGAATAACCCGTTC |
|---|---|---|
| I. Fungi | | |
| Pneumocystis carinii | PMC16SRR1 | TTACTAC---G------GTGGT |
| Cryptococcus neoformans | CPCDA | CTGCC-----T-C-CA---CC-C |
| Coccidiodes immitis | COIDA | ---------------------- |
| Blastomyces dermatitidis | BLODA | --GTT---ATG--G-------- |
| Aspergillus fumagatus | ASNDA | CTGCC-----T-C-CA---CC- |
| fumigatus | ASNRR5SS | TT----G-G----GC-TA--AG |
| fumigatus | ASNRRSSB | TT----G-G----GC-TA--AG |
| Candida albicans | YSASRSUA | TTACTAC---G------GTGGT |
| albicans | YSAL16S | TTACTAC---G------GTGGT |
| lusitaniae | YSASRRNAA | T-TT-------G---ATGAGAG |
| lusitaniae | YSASRSUE | T-TT-------G---ATGAGAG |
| kefyr | YSASRSUB | TTTT--------A--ATTAGAG |
| krusei | YSASRRNAC | ---------CCCATGGGGCCGA |
| krusei | YSASRSUD | ---------CCCATGGGGCCGA |
| tropicalis | YSASRRNAB | TTACTAC---G------GTGGT |
| tropicalis | YSASRSUG | TTACTAC---G------GTGGT |
| viswanathii | YSASRSUH | TTACTAC---G------GTGGT |
| parapsilosis | YSASRSUF | TTACTAC---G------GTGGT |
| guilliermondii | YSASRSUC | TTACTAC---G------GTGGT |
| glabrata | YS5CRRNAS | TTTT--------A--ATTAGAG |
| II. Highest homologous sequence in GenBank | | |
| Genome bacteriophage T7 | PT7DOT7 | --ACTTC--------------- |
| Bacteriophage T7,comple. | PT7CG | --ACTTC--------------- |
| Staphylococcus aureus | STATOXA | -----------C------TCGA |

TABLE XV

Probes for Cryptococcus (Cryp-691)

| Species | GenBank name | Cryp-691<br>GTGGTCCTGTATGCTCTTTACT |
|---|---|---|
| I. Fungi | | |
| Pneumocystis carinii | PMC16SRR1 | -----GG--C---GC-G--CT- |
| Cryptococcus neoformans | CPCDA | ---------------------- |
| Coccidiodes immitis | COIDA | C------G-CTG-AC----C-- |
| Blastomyces dermatitidis | BLODA | C------G-CCG-AC----C-- |
| Aspergillus fumagatus | ASNDA | C------G-CTG-AC----C-- |
| fumigatus | ASNRR5SS | CA----TGTG----C---AGA- |
| fumigatus | ASNRRSSB | CA----TGTG----C---AGA- |
| Candida albicans | YSASRSUA | -----GG--C---GC-G--CT- |
| albicans | YSAL16S | -----GG--C---GC-G--CT- |
| lusitaniae | YSASRRNAA | -----GG--C---GC-G--CT- |
| lusitaniae | YSASRSUE | CA----TGTG----C---AGAC |
| kefyr | YSASRSUB | ----NNG--C---GC-G--CT- |
| krusei | YSASRRNAC | -----GG--C---GC-G--TT- |
| krusei | YSASRSUD | CA----TGTG----C---AGAC |
| tropicalis | YSASRRNAB | -----GG--C---GC-G--CT- |
| tropicalis | YSASRSUG | -----NG--C---GC-G--CT- |
| viswanathii | YSASRSUH | -----GG--C---GC-G--CT- |
| parapsilosis | YSASRSUF | -----NG--C---GC-G--CT- |
| guilliermondii | YSASRSUC | TAAAAAA-CA---------GAG |
| glabrata | YS5CRRNAS | -----GG--C---GC-G--CT- |
| II. Highest homologous sequence in GenBank | | |
| Rat α tropomyosin | RATTMA3 | T-------T---------CGT- |
| Human ribonucl/angio | HUMRAJ | C----------C-ACA------ |
| Human ribonucl/angio inh | HUMRAI | C----------C-ACA------ |

TABLE XVI

Probes for Cryptococcus (Cryp-1042)

| Species | GenBank name | Cryp-1042 CACGTCAATCTCTGACTGGG |
|---|---|---|
| I. Fungi | | |
| *Pneumocystis carinii* | PMC16SRR1 | TT–T–G–T–––A––GG–––T |
| *Cryptococcus neoformans* | CPCDA | ––––––––––––––––––– |
| *Coccidiodes immitis* | COIDA | GG–––––G–A–TC–G–––TC |
| *Blastomyces dermatitidis* | BLODA | GG–––––G–A–TC–G–––TC |
| *Aspergillus fumagatus* | ASNDA | –G––CGCTA–A–––––A––– |
| *fumigatus* | ASNRR5SS | –G––CGCTA–A–––––A––– |
| *fumigatus* | ASNRRSSB | –G––CGCTA–A–––––A––– |
| *Candida albicans* | YSASRSUA | GGG–G–––C–––ATT––––A |
| *albicans* | YSAL16S | ––TTCA–––T––––C–CTAT |
| *lusitaniae* | YSASRRNAA | ––TTCA–––T––––C–CTAT |
| *lusitaniae* | YSASRSUE | ––TTCA–––T––––C–CTAT |
| *kefyr* | YSASRSUB | A–AA–––––G–––TCGGACT |
| *krusei* | YSASRRNAC | TG–––A––G–C–C––––TC– |
| *krusei* | YSASRSUD | –T–––G––A–––C–T–GT–C |
| *tropicalis* | YSASRRNAB | A–AA–––––G–––TCGGACT |
| *tropicalis* | YSASRSUG | –TN–––––A––TG–N–ATTT |
| *viswanathii* | YSASRSUH | A–A–––NNNGGGNNCNN––– |
| *parapsilosis* | YSASRSUF | ––TTCA–––T––––C–CTAT |
| *guilliermondii* | YSASRSUC | ––TTCA–––T––––C–CTAT |
| *glabrata* | YS5CRRNAS | GTT–––C–CT–––T–GA––– |
| II. Highest homologous sequence in GenBank | | |
| Rat α-1-acid gly.pro. | RATAGPA1H | T–TTA–––––––––––––T |
| Rat α-1-acid gly(sp-daw) | RATAGPA1G | T–TTA–––––––––––––T |
| *S.pneumoniae* malX malM | STRMALMXP | T–ACC––––––A–––––––– |

What is claimed is:

1. A combination of isolated polynucleotides having about the same at selected ionic strength with their complementary polynucleotides, said combination a plurality of different specific polynucleotides, each of said different specific polynucleotides having a sequence selected from the group consisting of SEQ ID NO:81, SEQ ID NO:104, SEQ ID NO:131, SEQ ID NO:154, SEQ ID NO:176, SEQ ID NO:199, SEQ ID NO:267, SEQ ID NO:290, SEQ ID NO:312, SEQ ID NO:335, SEQ ID NO:364, SEQ ID NO:391, and a sequence complementary to any of the foregoing; and at least one common polynucleotide having a sequence selected from the group consisting of SEQ ID NO:1, SEQ ID NO:21, SEQ ID NO:41, and SEQ ID NO:61, and a sequence complementary to any of the foregoing.

2. The combination of isolated polynucleotides according to claim 1 wherein said $T_m$ at selected ionic strengths with their complementary polynucleotides is 54° C.±1° C.

* * * * *

SEQUENCE LISTING ( 1 ) GENERAL INFORMATION:

( i i i ) NUMBER OF SEQUENCES: 407

( 2 ) INFORMATION FOR SEQ ID NO:1:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:1:

GAGGGAGCCT GAGAAACG        18

( 2 ) INFORMATION FOR SEQ ID NO:2:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA (iii) HYPOTHETICAL: NO (iv) ANTI-SENSE: NO (vi) ORIGINAL SOURCE:
    (A) ORGANISM: Cryptococcus neoformans (vii) IMMEDIATE SOURCE:
    (B) CLONE: CPCDA (xi) SEQUENCE DESCRIPTION: SEQ ID NO:2:

GAGGGAGCCT GAGAAACG                                                                 18

(2) INFORMATION FOR SEQ ID NO:3:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Coccidiodes immitis (vii) IMMEDIATE SOURCE:
        (B) CLONE: COIDA (xi) SEQUENCE DESCRIPTION: SEQ ID NO:3:

GAGGGAGCCT GAGAAACG                                                                 18

(2) INFORMATION FOR SEQ ID NO:4:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Blastomyces dermatitidis (vii) IMMEDIATE SOURCE:
        (B) CLONE: BLODA (xi) SEQUENCE DESCRIPTION: SEQ ID NO:4:

GAGGGAGCCT GAGAAACG                                                                 18

(2) INFORMATION FOR SEQ ID NO:5:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:

(A) ORGANISM: Aspergillus fumagatus (v i i) IMMEDIATE SOURCE:
(B) CLONE: ASNDA (x i) SEQUENCE DESCRIPTION: SEQ ID NO:5:

GAGGGAGCCT GAGAAACG 18

(2) INFORMATION FOR SEQ ID NO:6:

(i) SEQUENCE CHARACTERISTICS:
(A) LENGTH: 18 bases
(B) TYPE: nucleic acid
(C) STRANDEDNESS: single
(D) TOPOLOGY: linear (i i) MOLECULE TYPE: cDNA to rRNA (i i i) HYPOTHETICAL: NO (i v) ANTI-SENSE: NO (v i) ORIGINAL SOURCE:
(A) ORGANISM: Aspergillus fumigatus (v i i) IMMEDIATE SOURCE:
(B) CLONE: ASNRR5SS (x i) SEQUENCE DESCRIPTION: SEQ ID NO:6:

GAGGGAGCCT GAGAAACG 18

(2) INFORMATION FOR SEQ ID NO:7:

(i) SEQUENCE CHARACTERISTICS:
(A) LENGTH: 18 bases
(B) TYPE: nucleic acid
(C) STRANDEDNESS: single
(D) TOPOLOGY: linear (i i) MOLECULE TYPE: cDNA to rRNA (i i i) HYPOTHETICAL: NO (i v) ANTI-SENSE: NO (v i) ORIGINAL SOURCE:
(A) ORGANISM: Aspergillus fumigatus (v i i) IMMEDIATE SOURCE:
(B) CLONE: ASNRRSSB (x i) SEQUENCE DESCRIPTION: SEQ ID NO:7:

GAGGGAGCCT GAGAAACG 18

(2) INFORMATION FOR SEQ ID NO:8:

(i) SEQUENCE CHARACTERISTICS:
(A) LENGTH: 18 bases
(B) TYPE: nucleic acid
(C) STRANDEDNESS: single
(D) TOPOLOGY: linear (i i) MOLECULE TYPE: cDNA to rRNA (i i i) HYPOTHETICAL: NO (i v) ANTI-SENSE: NO (v i) ORIGINAL SOURCE:
(A) ORGANISM: Candida albicans (v i i) IMMEDIATE SOURCE:
(B) CLONE: YSASRSUA ( x i ) SEQUENCE DESCRIPTION: SEQ ID NO:8:

GAGGGAGCCT GAGAAACG                                                                                                 18

( 2 ) INFORMATION FOR SEQ ID NO:9:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:9:

GAGGGAGCCT GAGAAACG                                                                                                 18

( 2 ) INFORMATION FOR SEQ ID NO:10:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:10:

GAGGGAGCCT GAGAAACG                                                                                                 18

( 2 ) INFORMATION FOR SEQ ID NO:11:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:11:

GAGGGAGCCT GAGAAACG                                                                                                 18

( 2 ) INFORMATION FOR SEQ ID NO:12:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:12:

GAGGGAGCCT GAGAAACG         18

( 2 ) INFORMATION FOR SEQ ID NO:13:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:13:

GAGGGAGCCT GAGAAACG         18

( 2 ) INFORMATION FOR SEQ ID NO:14:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:14:

GAGGGAGCCT GAGAAACG         18

( 2 ) INFORMATION FOR SEQ ID NO:15:

( i ) SEQUENCE CHARACTERISTICS:
        ( A ) LENGTH: 18 bases
        ( B ) TYPE: nucleic acid ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida tropicalis ( v i i ) IMMEDIATE SOURCE:
                    ( B ) CLONE: YSASRRNAB ( x i ) SEQUENCE DESCRIPTION: SEQ ID NO:15:

GAGGGAGCCT GAGAAACG            18

( 2 ) INFORMATION FOR SEQ ID NO:16:

( i ) SEQUENCE CHARACTERISTICS:
                    ( A ) LENGTH: 18 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida tropicalis ( v i i ) IMMEDIATE SOURCE:
                    ( B ) CLONE: YSASRSUG ( x i ) SEQUENCE DESCRIPTION: SEQ ID NO:16:

GAGGGAGCCT GAGAAACG            18

( 2 ) INFORMATION FOR SEQ ID NO:17:

( i ) SEQUENCE CHARACTERISTICS:
                    ( A ) LENGTH: 18 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida viswanathii ( v i i ) IMMEDIATE SOURCE:
                    ( B ) CLONE: YSASRSUH ( x i ) SEQUENCE DESCRIPTION: SEQ ID NO:17:

GAGGGAGCCT GAGAAACG            18

( 2 ) INFORMATION FOR SEQ ID NO:18:

( i ) SEQUENCE CHARACTERISTICS:
                    ( A ) LENGTH: 18 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Candida parapsilosis ( v i i ) IMMEDIATE SOURCE:
  ( B ) CLONE: YSASRSUF ( x i ) SEQUENCE DESCRIPTION: SEQ ID NO:18:

GAGGGAGCCT GAGAAACG 18

( 2 ) INFORMATION FOR SEQ ID NO:19:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida guilliermondii ( v i i ) IMMEDIATE SOURCE:
    ( B ) CLONE: YSASRSUC ( x i ) SEQUENCE DESCRIPTION: SEQ ID NO:19:

GAGGGAGCCT GAGAAACG 18

( 2 ) INFORMATION FOR SEQ ID NO:20:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida glabrata ( v i i ) IMMEDIATE SOURCE:
    ( B ) CLONE: YS5CRRNAS ( x i ) SEQUENCE DESCRIPTION: SEQ ID NO:20:

GAGGGAGCCT GAGAAACG 18

( 2 ) INFORMATION FOR SEQ ID NO:21:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

( A ) ORGANISM: Pneumocystis carinii ( v i i ) IMMEDIATE SOURCE:
                    ( B ) CLONE: PMC16SRR1

( x i ) SEQUENCE DESCRIPTION: SEQ ID NO:21:

TCCAAGGAAG GCAGCAGG                                                                                    18

( 2 ) INFORMATION FOR SEQ ID NO:22:

( i ) SEQUENCE CHARACTERISTICS:
                    ( A ) LENGTH: 18 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Cryptococcus neoformans ( v i i ) IMMEDIATE SOURCE:
                    ( B ) CLONE: CPCDA ( x i ) SEQUENCE DESCRIPTION: SEQ ID NO:22:

TCCAAGGAAG GCAGCAGG                                                                                    18

( 2 ) INFORMATION FOR SEQ ID NO:23:

( i ) SEQUENCE CHARACTERISTICS:
                    ( A ) LENGTH: 18 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Coccidiodes immitis ( v i i ) IMMEDIATE SOURCE:
                    ( B ) CLONE: COIDA ( x i ) SEQUENCE DESCRIPTION: SEQ ID NO:23:

TCCAAGGAAG GCAGCAGG                                                                                    18

( 2 ) INFORMATION FOR SEQ ID NO:24:

( i ) SEQUENCE CHARACTERISTICS:
                    ( A ) LENGTH: 18 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Blastomyces dermatitidis ( v i i ) IMMEDIATE SOURCE:
                    ( B ) CLONE: BLODA ( x i ) SEQUENCE DESCRIPTION: SEQ ID NO:24:

TCCAAGGAAG GCAGCAGG                                                                                      18

( 2 ) INFORMATION FOR SEQ ID NO:25:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:25:

TCCAAGGAAG GCAGCAGG                                                                                      18

( 2 ) INFORMATION FOR SEQ ID NO:26:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:26:

TCCAAGGAAG GCAGCAGG                                                                                      18

( 2 ) INFORMATION FOR SEQ ID NO:27:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:27:

TCCAAGGAAG GCAGCAGG                                                                                      18

( 2 ) INFORMATION FOR SEQ ID NO:28:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:28:

TCCAAGGAAG GCAGCAGG                18

( 2 ) INFORMATION FOR SEQ ID NO:29:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:29:

TCCAAGGAAG GCAGCAGG                18

( 2 ) INFORMATION FOR SEQ ID NO:30:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:30:

TCCAAGGAAG GCAGCAGG                18

( 2 ) INFORMATION FOR SEQ ID NO:31:

( i ) SEQUENCE CHARACTERISTICS:
        ( A ) LENGTH: 18 bases
        ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida lusitaniae ( v i i ) IMMEDIATE SOURCE:
( B ) CLONE: YSASRSUE ( x i ) SEQUENCE DESCRIPTION: SEQ ID NO:31:

TCCAAGGAAG GCAGCAGG   18

( 2 ) INFORMATION FOR SEQ ID NO:32:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida kefyr ( v i i ) IMMEDIATE SOURCE:
( B ) CLONE: YSASRSUB ( x i ) SEQUENCE DESCRIPTION: SEQ ID NO:32:

TCCAAGGAAG GCAGCAGG   18

( 2 ) INFORMATION FOR SEQ ID NO:33:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida krusei ( v i i ) IMMEDIATE SOURCE:
( B ) CLONE: YSASRRNAC ( x i ) SEQUENCE DESCRIPTION: SEQ ID NO:33:

TCCAAGGAAG GCAGCAGG   18

( 2 ) INFORMATION FOR SEQ ID NO:34:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( i i ) MOLECULE TYPE: cDNA to rRNA (i i i) HYPOTHETICAL: NO (i v) ANTI-SENSE: NO (v i) ORIGINAL SOURCE:
    (A) ORGANISM: Candida krusei (v i i) IMMEDIATE SOURCE:
    (B) CLONE: YSASRSUD (x i) SEQUENCE DESCRIPTION: SEQ ID NO:34:

TCCAAGGAAG GCAGCAGG                                    18

(2) INFORMATION FOR SEQ ID NO:35:

(i) SEQUENCE CHARACTERISTICS:
        (A) LENGTH: 18 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida tropicalis (v i i) IMMEDIATE SOURCE:
        (B) CLONE: YSASRRNAB (x i) SEQUENCE DESCRIPTION: SEQ ID NO:35:

TCCAAGGAAG GCAGCAGG                                    18

(2) INFORMATION FOR SEQ ID NO:36:

(i) SEQUENCE CHARACTERISTICS:
        (A) LENGTH: 18 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida tropicalis (v i i) IMMEDIATE SOURCE:
        (B) CLONE: YSASRSUG (x i) SEQUENCE DESCRIPTION: SEQ ID NO:36:

TCCAAGGAAG GCAGCAGG                                    18

(2) INFORMATION FOR SEQ ID NO:37:

(i) SEQUENCE CHARACTERISTICS:
        (A) LENGTH: 18 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:

(A) ORGANISM: Candida viswanathii (vii) IMMEDIATE SOURCE:
(B) CLONE: YSASRSUH (xi) SEQUENCE DESCRIPTION: SEQ ID NO:37:

TCCAAGGAAG GCAGCAGG                           18

(2) INFORMATION FOR SEQ ID NO:38:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida parapsilosis (vii) IMMEDIATE SOURCE:
(B) CLONE: YSASRSUF (xi) SEQUENCE DESCRIPTION: SEQ ID NO:38:

TCCAAGGAAG GCAGCAGG                           18

(2) INFORMATION FOR SEQ ID NO:39:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida guilliermondii (vii) IMMEDIATE SOURCE:
(B) CLONE: YSASRSUC (xi) SEQUENCE DESCRIPTION: SEQ ID NO:39:

TCCAAGGAAG GCAGCAGG                           18

(2) INFORMATION FOR SEQ ID NO:40:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida glabrata (vii) IMMEDIATE SOURCE:
(B) CLONE: YS5CRRNAS ( x i ) SEQUENCE DESCRIPTION: SEQ ID NO:40:

TCCAAGGAAG GCAGCAGG                                                                                    18

( 2 ) INFORMATION FOR SEQ ID NO:41:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:41:

ACGGGGAAAC TCACCAGG                                                                                    18

( 2 ) INFORMATION FOR SEQ ID NO:42:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:42:

ACGGGGAAAC TCACCAGG                                                                                    18

( 2 ) INFORMATION FOR SEQ ID NO:43:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:43:

ACGGGGAAAC TCACCAGG                                                                                    18

( 2 ) INFORMATION FOR SEQ ID NO:44:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:44:

ACGGGGAAAC TCACCAGG         18

( 2 ) INFORMATION FOR SEQ ID NO:45:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:45:

ACGGGGAAAC TCACCAGG         18

( 2 ) INFORMATION FOR SEQ ID NO:46:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:46:

ACGGGGAAAC TCACCAGG         18

( 2 ) INFORMATION FOR SEQ ID NO:47:

( i ) SEQUENCE CHARACTERISTICS:
        ( A ) LENGTH: 18 bases
        ( B ) TYPE: nucleic acid ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Aspergillus fumigatus ( v i i ) IMMEDIATE SOURCE:
            ( B ) CLONE: ASNRRSSB ( x i ) SEQUENCE DESCRIPTION: SEQ ID NO:47:

ACGGGGAAAC TCACCAGG                                                                               1 8

( 2 ) INFORMATION FOR SEQ ID NO:48:

( i ) SEQUENCE CHARACTERISTICS:
            ( A ) LENGTH: 18 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida albicans ( v i i ) IMMEDIATE SOURCE:
            ( B ) CLONE: YSASRSUA ( x i ) SEQUENCE DESCRIPTION: SEQ ID NO:48:

ACGGGGAAAC TCACCAGG                                                                               1 8

( 2 ) INFORMATION FOR SEQ ID NO:49:

( i ) SEQUENCE CHARACTERISTICS:
            ( A ) LENGTH: 18 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candidi albicans ( v i i ) IMMEDIATE SOURCE:
            ( B ) CLONE: YSAL16S ( x i ) SEQUENCE DESCRIPTION: SEQ ID NO:49:

ACGGGGAAAC TCACCAGG                                                                               1 8

( 2 ) INFORMATION FOR SEQ ID NO:50:

( i ) SEQUENCE CHARACTERISTICS:
            ( A ) LENGTH: 18 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Candida lusitaniae ( v i i ) IMMEDIATE SOURCE:
  ( B ) CLONE: YSASRRNAA ( x i ) SEQUENCE DESCRIPTION: SEQ ID NO:50:

ACGGGGAAAC TCACCAGG 18

( 2 ) INFORMATION FOR SEQ ID NO:51:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida lusitaniae ( v i i ) IMMEDIATE SOURCE:
    ( B ) CLONE: YSASRSUE ( x i ) SEQUENCE DESCRIPTION: SEQ ID NO:51:

ACGGGGAAAC TCACCAGG 18

( 2 ) INFORMATION FOR SEQ ID NO:52:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida kefyr ( v i i ) IMMEDIATE SOURCE:
    ( B ) CLONE: YSASRSUB ( x i ) SEQUENCE DESCRIPTION: SEQ ID NO:52:

ACGGGGAAAC TCACCAGG 18

( 2 ) INFORMATION FOR SEQ ID NO:53:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida krusei (vii) IMMEDIATE SOURCE:
  (B) CLONE: YSASRRNAC (xi) SEQUENCE DESCRIPTION: SEQ ID NO:53:

ACGGGGAAAC TCACCAGG                                                                                            18

(2) INFORMATION FOR SEQ ID NO:54:

(i) SEQUENCE CHARACTERISTICS:
    (A) LENGTH: 18 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida krusei (vii) IMMEDIATE SOURCE:
    (B) CLONE: YSASRSUD (xi) SEQUENCE DESCRIPTION: SEQ ID NO:54:

ACGGGGAAAC TCACCAGG                                                                                            18

(2) INFORMATION FOR SEQ ID NO:55:

(i) SEQUENCE CHARACTERISTICS:
    (A) LENGTH: 18 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida tropicalis (vii) IMMEDIATE SOURCE:
    (B) CLONE: YSASRRNAB (xi) SEQUENCE DESCRIPTION: SEQ ID NO:55:

ACGGGGAAAC TCACCAGG                                                                                            18

(2) INFORMATION FOR SEQ ID NO:56:

(i) SEQUENCE CHARACTERISTICS:
    (A) LENGTH: 18 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida tropicalis (vii) IMMEDIATE SOURCE:
    (B) CLONE: YSASRSUG ( x i ) SEQUENCE DESCRIPTION: SEQ ID NO:56:

ACGGGGAAAC TCACCAGG                                                                                    18

( 2 ) INFORMATION FOR SEQ ID NO:57:

( i ) SEQUENCE CHARACTERISTICS:
                ( A ) LENGTH: 18 bases
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Candida viswanathii ( v i i ) IMMEDIATE SOURCE:
                ( B ) CLONE: YSASRSUH ( x i ) SEQUENCE DESCRIPTION: SEQ ID NO:57:

ACGGGGAAAC TCACCAGG                                                                                    18

( 2 ) INFORMATION FOR SEQ ID NO:58:

( i ) SEQUENCE CHARACTERISTICS:
                ( A ) LENGTH: 18 bases
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Candida parapsilosis ( v i i ) IMMEDIATE SOURCE:
                ( B ) CLONE: YSASRSUF ( x i ) SEQUENCE DESCRIPTION: SEQ ID NO:58:

ACGGGGAAAC TCACCAGG                                                                                    18

( 2 ) INFORMATION FOR SEQ ID NO:59:

( i ) SEQUENCE CHARACTERISTICS:
                ( A ) LENGTH: 18 bases
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Candida guilliermondii ( v i i ) IMMEDIATE SOURCE:
                ( B ) CLONE: YSASRSUC ( x i ) SEQUENCE DESCRIPTION: SEQ ID NO:59:

ACGGGGAAAC TCACCAGG                                                                                    18

( 2 ) INFORMATION FOR SEQ ID NO:60:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:60:

ACGGGGAAAC TCACCAGG                                              1 8

( 2 ) INFORMATION FOR SEQ ID NO:61:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:61:

TCGTGCTGGG GATAGAGC                                              1 8

( 2 ) INFORMATION FOR SEQ ID NO:62:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:62:

TCGTGCTGGG GATAGAGC                                              1 8

( 2 ) INFORMATION FOR SEQ ID NO:63:

( i ) SEQUENCE CHARACTERISTICS:
        ( A ) LENGTH: 18 bases
        ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Coccidiodes immitis (vii) IMMEDIATE SOURCE:
(B) CLONE: COIDA (xi) SEQUENCE DES (i i i) HYPOTHETICAL: NO (i v) ANTI-SENSE: NO (v i) ORIGINAL SOURCE:
    (A) ORGANISM: Aspergillus fumigatus (v i i) IMMEDIATE SOURCE:
    (B) CLONE: ASNRR5SS (x i) SEQUENCE DESCRIPTION: SEQ ID NO:66:

TCGTGCTGGG GATAGAGC      18

(2) INFORMATION FOR SEQ ID NO:67:

(i) SEQUENCE CHARACTERISTICS:
        (A) LENGTH: 18 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Aspergillus fumigatus (v i i) IMMEDIATE SOURCE:
        (B) CLONE: ASNRRSSB (x i) SEQUENCE DESCRIPTION: SEQ ID NO:67:

TCGTGCTGGG GATAGAGC      18

(2) INFORMATION FOR SEQ ID NO:68:

(i) SEQUENCE CHARACTERISTICS:
        (A) LENGTH: 18 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida albicans (v i i) IMMEDIATE SOURCE:
        (B) CLONE: YSASRSUA (x i) SEQUENCE DESCRIPTION: SEQ ID NO:68:

TCGTGCTGGG GATAGAGC      18

(2) INFORMATION FOR SEQ ID NO:69:

(i) SEQUENCE CHARACTERISTICS:
        (A) LENGTH: 18 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:

(A) ORGANISM: Candidi albicans (vii) IMMEDIATE SOURCE:
                (B) CLONE: YSAL16S (xi) SEQUENCE DESCRIPTION: SEQ ID NO:69:

TCGTGCTGGG GATAGAGC                                                                                        18

(2) INFORMATION FOR SEQ ID NO:70:

(i) SEQUENCE CHARACTERISTICS:
                (A) LENGTH: 18 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Candida lusitaniae (vii) IMMEDIATE SOURCE:
                (B) CLONE: YSASRRNAA (xi) SEQUENCE DESCRIPTION: SEQ ID NO:70:

TCGTGCTGGG GATAGAGC                                                                                        18

(2) INFORMATION FOR SEQ ID NO:71:

(i) SEQUENCE CHARACTERISTICS:
                (A) LENGTH: 18 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Candida lusitaniae (vii) IMMEDIATE SOURCE:
                (B) CLONE: YSASRSUE (xi) SEQUENCE DESCRIPTION: SEQ ID NO:71:

TCGTGCTGGG GATAGAGC                                                                                        18

(2) INFORMATION FOR SEQ ID NO:72:

(i) SEQUENCE CHARACTERISTICS:
                (A) LENGTH: 18 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Candida kefyr (vii) IMMEDIATE SOURCE:
                (B) CLONE: YSASRSUB ( x i ) SEQUENCE DESCRIPTION: SEQ ID NO:72:

TCGTGCTGGG GATAGAGC 18

( 2 ) INFORMATION FOR SEQ ID NO:73:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:73:

TCGTGCTGGG GATAGAGC 18

( 2 ) INFORMATION FOR SEQ ID NO:74:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:74:

TCGTGCTGGG GATAGAGC 18

( 2 ) INFORMATION FOR SEQ ID NO:75:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:75:

TCGTGCTGGG GATAGAGC 18

( 2 ) INFORMATION FOR SEQ ID NO:76:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:76:

TCGTGCTGGG GATAGAGC        18

( 2 ) INFORMATION FOR SEQ ID NO:77:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:77:

TCGTGCTGGG GATAGAGC        18

( 2 ) INFORMATION FOR SEQ ID NO:78:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:78:

TCGTGCTGGG GATAGAGC        18

( 2 ) INFORMATION FOR SEQ ID NO:79:

( i ) SEQUENCE CHARACTERISTICS:
        ( A ) LENGTH: 18 bases
        ( B ) TYPE: nucleic acid ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida guilliermondii ( v i i ) IMMEDIATE SOURCE:
            ( B ) CLONE: YSASRSUC ( x i ) SEQUENCE DESCRIPTION: SEQ ID NO:79:

TCGTGCTGGG GATAGAGC                                                                     18

( 2 ) INFORMATION FOR SEQ ID NO:80:

( i ) SEQUENCE CHARACTERISTICS:
            ( A ) LENGTH: 18 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida glabrata ( v i i ) IMMEDIATE SOURCE:
            ( B ) CLONE: YS5CRRNAS ( x i ) SEQUENCE DESCRIPTION: SEQ ID NO:80:

TCGTGCTGGG GATAGAGC                                                                     18

( 2 ) INFORMATION FOR SEQ ID NO:81:

( i ) SEQUENCE CHARACTERISTICS:
            ( A ) LENGTH: 18 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Pneumocystis carinii ( v i i ) IMMEDIATE SOURCE:
            ( B ) CLONE: PMC16SRR1

( x i ) SEQUENCE DESCRIPTION: SEQ ID NO:81:

GCGCAACTGA TCCTTCCC                                                                     18

( 2 ) INFORMATION FOR SEQ ID NO:82:

( i ) SEQUENCE CHARACTERISTICS:
            ( A ) LENGTH: 18 bases
            ( B ) TYPE: nucleic acid
            ( C ) STRANDEDNESS: single
            ( D ) TOPOLOGY: linear ( i i ) MOLECULE TYPE: cDNA to rRNA (iii) HYPOTHETICAL: NO (iv) ANTI-SENSE: NO (vi) ORIGINAL SOURCE:
 (A) ORGANISM: Cryptococcus neoformans (vii) IMMEDIATE SOURCE:
 (B) CLONE: CPCDA (xi) SEQUENCE DESCRIPTION: SEQ ID NO:82:

GTGCCGGCGA TGCTTCAT 18

(2) INFORMATION FOR SEQ ID NO:83:

(i) SEQUENCE CHARACTERISTICS:
  (A) LENGTH: 18 bases
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Coccidiodes immitis (vii) IMMEDIATE SOURCE:
  (B) CLONE: COIDA (xi) SEQUENCE DESCRIPTION: SEQ ID NO:83:

ACCTGGTTGA TCCTGCCA 18

(2) INFORMATION FOR SEQ ID NO:84:

(i) SEQUENCE CHARACTERISTICS:
  (A) LENGTH: 18 bases
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Blastomyces dermatitidis (vii) IMMEDIATE SOURCE:
  (B) CLONE: BLODA (xi) SEQUENCE DESCRIPTION: SEQ ID NO:84:

ACCTGGTTGA TCCTGCCA 18

(2) INFORMATION FOR SEQ ID NO:85:

(i) SEQUENCE CHARACTERISTICS:
  (A) LENGTH: 18 bases
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:

(A) ORGANISM: Aspergillus fumagatus (vii) IMMEDIATE SOURCE:
(B) CLONE: ASNDA (xi) SEQUENCE DESCRIPTION: SEQ ID NO:85:

ACCTGGTTGA TCCTGCCA                                                                                          18

(2) INFORMATION FOR SEQ ID NO:86:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Aspergillus fumigatus (vii) IMMEDIATE SOURCE:
(B) CLONE: ASNRR5SS (xi) SEQUENCE DESCRIPTION: SEQ ID NO:86:

GCGCCGGCGA TGGTTCAT                                                                                          18

(2) INFORMATION FOR SEQ ID NO:87:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Aspergillus fumigatus (vii) IMMEDIATE SOURCE:
(B) CLONE: ASNRRSSB (xi) SEQUENCE DESCRIPTION: SEQ ID NO:87:

GCGCCGGCGA TGGTTCAT                                                                                          18

(2) INFORMATION FOR SEQ ID NO:88:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida albicans (vii) IMMEDIATE SOURCE:
(B) CLONE: YSASRSUA ( x i ) SEQUENCE DESCRIPTION: SEQ ID NO:88:

GCGCAAGTCA TCAGCTTG                                                                                          18

( 2 ) INFORMATION FOR SEQ ID NO:89:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:89:

GCGCAAGTCA TCAGCTTG                                                                                          18

( 2 ) INFORMATION FOR SEQ ID NO:90:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:90:

GCGCAAGTCA TCAGCTTG                                                                                          18

( 2 ) INFORMATION FOR SEQ ID NO:91:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:91:

GCGCAAGTCA TCAGCTTG                                                                                          18

( 2 ) INFORMATION FOR SEQ ID NO:92:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:92:

GCGCAAGTCA TCAGCTTG        18

( 2 ) INFORMATION FOR SEQ ID NO:93:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:93:

GCGCAAGTCA TCAGCTTG        18

( 2 ) INFORMATION FOR SEQ ID NO:94:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:94:

GCGCAAGTCA TCAGCTTG        18

( 2 ) INFORMATION FOR SEQ ID NO:95:

( i ) SEQUENCE CHARACTERISTICS:
        ( A ) LENGTH: 18 bases
        ( B ) TYPE: nucleic acid ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:95:

GCGCAAGTCA TCAGCTTG 18

( 2 ) INFORMATION FOR SEQ ID NO:96:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:96:

GCGCAAGTCA TCAGCTTG 18

( 2 ) INFORMATION FOR SEQ ID NO:97:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:97:

GCGCAAGTCA TCAGCTTG 18

( 2 ) INFORMATION FOR SEQ ID NO:98:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Candida parapsilosis ( v i i ) IMMEDIATE SOURCE:
                ( B ) CLONE: YSASRSUF ( x i ) SEQUENCE DESCRIPTION: SEQ ID NO:98:

GCGCAAGTCA TCAGCTTG                                                                          1 8

( 2 ) INFORMATION FOR SEQ ID NO:99:

( i ) SEQUENCE CHARACTERISTICS:
                ( A ) LENGTH: 18 bases
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Candida guilliermondii ( v i i ) IMMEDIATE SOURCE:
                ( B ) CLONE: YSASRSUC ( x i ) SEQUENCE DESCRIPTION: SEQ ID NO:99:

GCGCAAGTCA TCAGCTTG                                                                          1 8

( 2 ) INFORMATION FOR SEQ ID NO:100:

( i ) SEQUENCE CHARACTERISTICS:
                ( A ) LENGTH: 18 bases
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Candida glabrata ( v i i ) IMMEDIATE SOURCE:
                ( B ) CLONE: YS5CRRNAS ( x i ) SEQUENCE DESCRIPTION: SEQ ID NO:100:

GCGCAAGTCA TCAGCTTG                                                                          1 8

( 2 ) INFORMATION FOR SEQ ID NO:101:

( i ) SEQUENCE CHARACTERISTICS:
                ( A ) LENGTH: 18 bases
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Human TAN-1

(vii) IMMEDIATE SOURCE:
(B) CLONE: HUMTAN1

(xi) SEQUENCE DESCRIPTION: SEQ ID NO:101:

GCGCAACAGC TCCTTCCC                                                                                                18

(2) INFORMATION FOR SEQ ID NO:102:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Abccelsyn xylium (vii) IMMEDIATE SOURCE:
(B) CLONE: ABCCELSYN (xi) SEQUENCE DESCRIPTION: SEQ ID NO:102:

GAGGAACTGA TCCTTCCC                                                                                                18

(2) INFORMATION FOR SEQ ID NO:103:

(i) SEQUENCE CHARACTERISTICS:
(A) LENGTH: 18 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Human mRNA neuron (vii) IMMEDIATE SOURCE:
(B) CLONE: HUMNSEMRNA (xi) SEQUENCE DESCRIPTION: SEQ ID NO:103:

CTCCCACTGA TCCTTCCC                                                                                                18

(2) INFORMATION FOR SEQ ID NO:104:

(i) SEQUENCE CHARACTERISTICS:
(A) LENGTH: 23 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Pneumocystis carinii (vii) IMMEDIATE SOURCE:
(B) CLONE: PMC16SRR1

( x i ) SEQUENCE DESCRIPTION: SEQ ID NO:104:

GGCGATGTTT TTTTCTTGAC TCG  23

( 2 ) INFORMATION FOR SEQ ID NO:105:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:105:

GGCGATGCTT CATTCAAATA TCT  23

( 2 ) INFORMATION FOR SEQ ID NO:106:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:106:

GGCGATGGTT CATTCAAATT TCT  23

( 2 ) INFORMATION FOR SEQ ID NO:107:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:107:

GGCGATGGTT CATTCAAATT TCT  23

( 2 ) INFORMATION FOR SEQ ID NO:108:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:108:

GGCGGTGTTT CTATGATGAC CCG        23

( 2 ) INFORMATION FOR SEQ ID NO:109:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:109:

GGCGGTGTTT CTATGATGAC CCG        23

( 2 ) INFORMATION FOR SEQ ID NO:110:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:110:

GGCGGTGTTT CTATGATGAC CCG        23

( 2 ) INFORMATION FOR SEQ ID NO:111:

( i ) SEQUENCE CHARACTERISTICS:
        ( A ) LENGTH: 23 bases
        ( B ) TYPE: nucleic acid ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida albicans ( v i i ) IMMEDIATE SOURCE:
                    ( B ) CLONE: YSASRSUA ( x i ) SEQUENCE DESCRIPTION: SEQ ID NO:111:

GTTGTTGTTC TTTTATTGAC GCA                                                                     23

( 2 ) INFORMATION FOR SEQ ID NO:112:

( i ) SEQUENCE CHARACTERISTICS:
                    ( A ) LENGTH: 23 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candidi albicans ( v i i ) IMMEDIATE SOURCE:
                    ( B ) CLONE: YSAL16S ( x i ) SEQUENCE DESCRIPTION: SEQ ID NO:112:

GTTGTTGTTC TTTTATTGAC GCA                                                                     23

( 2 ) INFORMATION FOR SEQ ID NO:113:

( i ) SEQUENCE CHARACTERISTICS:
                    ( A ) LENGTH: 23 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida lusitaniae ( v i i ) IMMEDIATE SOURCE:
                    ( B ) CLONE: YSASRRNAA ( x i ) SEQUENCE DESCRIPTION: SEQ ID NO:113:

GGCGGCGTTC ATTTAGTGAC GCG                          .                                          23

( 2 ) INFORMATION FOR SEQ ID NO:114:

( i ) SEQUENCE CHARACTERISTICS:
                    ( A ) LENGTH: 23 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
  ( A ) ORGANISM: Candida lusitaniae ( v i i ) IMMEDIATE SOURCE:
  ( B ) CLONE: YSASRSUE ( x i ) SEQUENCE DESCRIPTION: SEQ ID NO:114:

GGCGGCGTTC ATTTAGTGAC GCG  23

( 2 ) INFORMATION FOR SEQ ID NO:115:

( i ) SEQUENCE CHARACTERISTICS:
    ( A ) LENGTH: 23 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida kefyr ( v i i ) IMMEDIATE SOURCE:
    ( B ) CLONE: YSASRSUB ( x i ) SEQUENCE DESCRIPTION: SEQ ID NO:115:

GGCGATGGTT CATTCAAATT TCT  23

( 2 ) INFORMATION FOR SEQ ID NO:116:

( i ) SEQUENCE CHARACTERISTICS:
    ( A ) LENGTH: 23 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida krusei ( v i i ) IMMEDIATE SOURCE:
    ( B ) CLONE: YSASRRNAC ( x i ) SEQUENCE DESCRIPTION: SEQ ID NO:116:

GGCCGTTTTT AGTCCTTGGA GTG  23

( 2 ) INFORMATION FOR SEQ ID NO:117:

( i ) SEQUENCE CHARACTERISTICS:
    ( A ) LENGTH: 23 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida krusei (vii) IMMEDIATE SOURCE:
                (B) CLONE: YSASRSUD (xi) SEQUENCE DESCRIPTION: SEQ ID NO:117:

TATTTTGTTN GTTTCTAGGA CCA                                                                                          23

(2) INFORMATION FOR SEQ ID NO:118:

(i) SEQUENCE CHARACTERISTICS:
                (A) LENGTH: 23 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Candida tropicalis (vii) IMMEDIATE SOURCE:
                (B) CLONE: YSASRRNAB (xi) SEQUENCE DESCRIPTION: SEQ ID NO:118:

GTTGTTGTTC TTTTATTGAC GCA                                                                                          23

(2) INFORMATION FOR SEQ ID NO:119:

(i) SEQUENCE CHARACTERISTICS:
                (A) LENGTH: 23 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Candida tropicalis (vii) IMMEDIATE SOURCE:
                (B) CLONE: YSASRSUG (xi) SEQUENCE DESCRIPTION: SEQ ID NO:119:

GTTGTTGTTC TTTTATTGAC GCA                                                                                          23

(2) INFORMATION FOR SEQ ID NO:120:

(i) SEQUENCE CHARACTERISTICS:
                (A) LENGTH: 23 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Candida viswanathii (vii) IMMEDIATE SOURCE:
                (B) CLONE: YSASRSUH ( x i ) SEQUENCE DESCRIPTION: SEQ ID NO:120:

GTTGTTGTTC TTTTATTGAC GCA                                    23

( 2 ) INFORMATION FOR SEQ ID NO:121:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:121:

GTTGTTGTTC TTTTATTGAC GCA                                    23

( 2 ) INFORMATION FOR SEQ ID NO:122:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:122:

GGTGTTGTTC TKTTTTGAC GCA                                     23

( 2 ) INFORMATION FOR SEQ ID NO:123:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:123:

GGTGGTGTTT TTTTAGTGAC CCA                                    23

( 2 ) INFORMATION FOR SEQ ID NO:124:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Tobacco chloroplast ( v i i ) IMMEDIATE SOURCE:
        ( B ) CLONE: TOBCPTGRG ( x i ) SEQUENCE DESCRIPTION: SEQ ID NO:124:

CGAGCCGTTT TTTTCTTGAC TCG        23

( 2 ) INFORMATION FOR SEQ ID NO:125:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aureobasidium pullulans ( v i i ) IMMEDIATE SOURCE:
        ( B ) CLONE: AURRR16S ( x i ) SEQUENCE DESCRIPTION: SEQ ID NO:125:

GGCGATGTTA TCATTTTGAC TCG        23

( 2 ) INFORMATION FOR SEQ ID NO:126:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: N. Tabacum ( v i i ) IMMEDIATE SOURCE:
        ( B ) CLONE: TOBCOCG ( x i ) SEQUENCE DESCRIPTION: SEQ ID NO:126:

CGAGCCGTTT TTTTCTTGAC TCG        23

( 2 ) INFORMATION FOR SEQ ID NO:127:

( i ) SEQUENCE CHARACTERISTICS:
        ( A ) LENGTH: 19 bases
        ( B ) TYPE: nucleic acid

```
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Pneumocystis carinii ( v i i ) IMMEDIATE SOURCE:
            ( B ) CLONE: PMC16SRR1

( x i ) SEQUENCE DESCRIPTION: SEQ ID NO:127:
```

AACACGGGGA AACTCACCA                                                                  19

```
( 2 ) INFORMATION FOR SEQ ID NO:128:

( i ) SEQUENCE CHARACTERISTICS:
            ( A ) LENGTH: 19 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Cryptococcus neoformans ( v i i ) IMMEDIATE SOURCE:
            ( B ) CLONE: CPCDA ( x i ) SEQUENCE DESCRIPTION: SEQ ID NO:128:
```

AACACGGGGA AACTCACCA                                                                  19

```
( 2 ) INFORMATION FOR SEQ ID NO:129:

( i ) SEQUENCE CHARACTERISTICS:
            ( A ) LENGTH: 19 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Coccidiodes immitis ( v i i ) IMMEDIATE SOURCE:
            ( B ) CLONE: COIDA ( x i ) SEQUENCE DESCRIPTION: SEQ ID NO:129:
```

CTTCTGGGGA ACCCTATGG                                                                  19

```
( 2 ) INFORMATION FOR SEQ ID NO:130:

( i ) SEQUENCE CHARACTERISTICS:
            ( A ) LENGTH: 19 bases
            ( B ) TYPE: nucleic acid
            ( C ) STRANDEDNESS: single
            ( D ) TOPOLOGY: linear ( i i ) MOLECULE TYPE: cDNA to rRNA
```

( i i i ) HYPOTHETICAL: NO ( i v ) ANTI-SENSE: NO ( v i ) ORIGINAL SOURCE:
    ( A ) ORGANISM: Blastomyces dermatitidis ( v i i ) IMMEDIATE SOURCE:
    ( B ) CLONE: BLODA ( x i ) SEQUENCE DESCRIPTION: SEQ ID NO:130:

CTCCTGGGAA GCCCCATGG 19

( 2 ) INFORMATION FOR SEQ ID NO:131:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:131:

CTTCTGGGGA ACCTCATGG 19

( 2 ) INFORMATION FOR SEQ ID NO:132:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:132:

CTTCTGGGGA ACCTCATGG 19

( 2 ) INFORMATION FOR SEQ ID NO:133:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Aspergillus fumigatus (vii) IMMEDIATE SOURCE:
(B) CLONE: ASNRRSSB (xi) SEQUENCE DESCRIPTION: SEQ ID NO:133:

CTTCTGGGGA ACCTCATGG     19

(2) INFORMATION FOR SEQ ID NO:134:

(i) SEQUENCE CHARACTERISTICS:
(A) LENGTH: 19 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida albicans (vii) IMMEDIATE SOURCE:
(B) CLONE: YSASRSUA (xi) SEQUENCE DESCRIPTION: SEQ ID NO:134:

AAAGGGGCA ACCTCATTC     19

(2) INFORMATION FOR SEQ ID NO:135:

(i) SEQUENCE CHARACTERISTICS:
(A) LENGTH: 19 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candidi albicans (vii) IMMEDIATE SOURCE:
(B) CLONE: YSAL16S (xi) SEQUENCE DESCRIPTION: SEQ ID NO:135:

AACACGGGGA AACTCACCA     19

(2) INFORMATION FOR SEQ ID NO:136:

(i) SEQUENCE CHARACTERISTICS:
(A) LENGTH: 19 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida lusitaniae (vii) IMMEDIATE SOURCE:
(B) CLONE: YSASRRNAA ( x i ) SEQUENCE DESCRIPTION: SEQ ID NO:136:

AATCTTGGGA AACTCCGTC                                                                                                        1 9

( 2 ) INFORMATION FOR SEQ ID NO:137:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:137:

AATCTTGGGA AACTCCGTC                                                                                                        1 9

( 2 ) INFORMATION FOR SEQ ID NO:138:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:138:

CTTCTGGCTA ACCTGTACT                                                                                                        1 9

( 2 ) INFORMATION FOR SEQ ID NO:139:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:139:

AACACGGGGA AACTCACCA                                                                                                        1 9

( 2 ) INFORMATION FOR SEQ ID NO:140:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:140:

CTTCTGGCTA SCCTCGGGC                                  19

( 2 ) INFORMATION FOR SEQ ID NO:141:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:141:

CTTCTGGCTA GCCTTTTGG                                  19

( 2 ) INFORMATION FOR SEQ ID NO:142:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:142:

CTTCTGGCTA GCCTTTTGG                                  19

( 2 ) INFORMATION FOR SEQ ID NO:143:

( i ) SEQUENCE CHARACTERISTICS:
        ( A ) LENGTH: 19 bases
        ( B ) TYPE: nucleic acid (C) STRANDEDNESS: single
(D) TOPOLOGY: linear (i i) MOLECULE TYPE: cDNA to rRNA (i i i) HYPOTHETICAL: NO (i v) ANTI-SENSE: NO (v i) ORIGINAL SOURCE:
   (A) ORGANISM: Candida viswanathii (v i i) IMMEDIATE SOURCE:
   (B) CLONE: YSASRSUH (x i) SEQUENCE DESCRIPTION: SEQ ID NO:143:

CTTCTGGCTA GCCTTTTGG                            19

(2) INFORMATION FOR SEQ ID NO:144:

(i) SEQUENCE CHARACTERISTICS:
      (A) LENGTH: 19 bases
      (B) TYPE: nucleic acid
      (C) STRANDEDNESS: single
      (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
      (A) ORGANISM: Candida parapsilosis (v i i) IMMEDIATE SOURCE:
      (B) CLONE: YSASRSUF (x i) SEQUENCE DESCRIPTION: SEQ ID NO:144:

AACACGGGGA AACTCACCA                            19

(2) INFORMATION FOR SEQ ID NO:145:

(i) SEQUENCE CHARACTERISTICS:
      (A) LENGTH: 19 bases
      (B) TYPE: nucleic acid
      (C) STRANDEDNESS: single
      (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
      (A) ORGANISM: Candida guilliermondii (v i i) IMMEDIATE SOURCE:
      (B) CLONE: YSASRSUC (x i) SEQUENCE DESCRIPTION: SEQ ID NO:145:

CTTCTGGCTA ACCATTCGC                            19

(2) INFORMATION FOR SEQ ID NO:146:

(i) SEQUENCE CHARACTERISTICS:
      (A) LENGTH: 19 bases
      (B) TYPE: nucleic acid
      (C) STRANDEDNESS: single
      (D) TOPOLOGY: linear (i i) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida glabrata ( v i i ) IMMEDIATE SOURCE:
    ( B ) CLONE: YS5CRRNAS ( x i ) SEQUENCE DESCRIPTION: SEQ ID NO:146:

CTTCTGGCTA ACCCCAAGT  19

( 2 ) INFORMATION FOR SEQ ID NO:147:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Penniclium notatum sub ( v i i ) IMMEDIATE SOURCE:
        ( B ) CLONE: PNNDA ( x i ) SEQUENCE DESCRIPTION: SEQ ID NO:147:

CTTCTGGCTA ACCTCATGG  19

( 2 ) INFORMATION FOR SEQ ID NO:148:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Human HLA-B-AT3

( v i i ) IMMEDIATE SOURCE:
        ( B ) CLONE: HUMBAT3A ( x i ) SEQUENCE DESCRIPTION: SEQ ID NO:148:

CTTCTGGCTA ACCTGCTAG  19

( 2 ) INFORMATION FOR SEQ ID NO:149:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Rat Olfactory protein (vii) IMMEDIATE SOURCE:
  (B) CLONE: RATOLFPRON (xi) SEQUENCE DESCRIPTION: SEQ ID NO:149:

CTCCTGGCTA ACCTCATCA         19

(2) INFORMATION FOR SEQ ID NO:150:

(i) SEQUENCE CHARACTERISTICS:
    (A) LENGTH: 21 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Pneumocystis carinii (vii) IMMEDIATE SOURCE:
    (B) CLONE: PMC16SRR1

(xi) SEQUENCE DESCRIPTION: SEQ ID NO:150:

GGCGATGTTT TTTTCTTGAG T         21

(2) INFORMATION FOR SEQ ID NO:151:

(i) SEQUENCE CHARACTERISTICS:
    (A) LENGTH: 21 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Cryptococcus neoformans (vii) IMMEDIATE SOURCE:
    (B) CLONE: CPCDA (xi) SEQUENCE DESCRIPTION: SEQ ID NO:151:

TTGTTGGTTT CTAGGATCGC C         21

(2) INFORMATION FOR SEQ ID NO:152:

(i) SEQUENCE CHARACTERISTICS:
    (A) LENGTH: 21 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Coccidiodes immitis (vii) IMMEDIATE SOURCE:
    (B) CLONE: COIDA ( 2 ) INFORMATION FOR SEQ ID NO:156:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:156:

GGCGGTGTTT CTATGATGAC C            21

( 2 ) INFORMATION FOR SEQ ID NO:157:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:157:

CCTTCGGGCT CTTTGATGAT T            21

( 2 ) INFORMATION FOR SEQ ID NO:158:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:158:

CCTTCGGGCT CTTTGATGAT T            21

( 2 ) INFORMATION FOR SEQ ID NO:159:

( i ) SEQUENCE CHARACTERISTICS:
        ( A ) LENGTH: 21 bases
        ( B ) TYPE: nucleic acid ( x i ) SEQUENCE DESCRIPTION: SEQ ID NO:152:

ACGTGTGGTT CTATTTGTT G 21

( 2 ) INFORMATION FOR SEQ ID NO:153:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:153:

GACGGGGTTC TTATGATGAC C 21

( 2 ) INFORMATION FOR SEQ ID NO:154:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:154:

GGCGGTGTTT CTATGATGAC C 21

( 2 ) INFORMATION FOR SEQ ID NO:155:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:155:

GGCGGTGTTT CTATGATGAC C 21

( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida lusitaniae ( v i i ) IMMEDIATE SOURCE:
    ( B ) CLONE: YSASRRNAA ( x i ) SEQUENCE DESCRIPTION: SEQ ID NO:159:

GGCGGCGTTC ATTTAGTGAC G      21

( 2 ) INFORMATION FOR SEQ ID NO:160:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:160:

GGCGGCGTTC ATTTAGTGAC G      21

( 2 ) INFORMATION FOR SEQ ID NO:161:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:161:

GGTGGTGTTT TTCTTATGAC C      21

( 2 ) INFORMATION FOR SEQ ID NO:162:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida krusei ( v i i ) IMMEDIATE SOURCE:
                    ( B ) CLONE: YSASRRNAC ( x i ) SEQUENCE DESCRIPTION: SEQ ID NO:162:

GACGGTCTAC CTATGGTAAG C            21

( 2 ) INFORMATION FOR SEQ ID NO:163:

( i ) SEQUENCE CHARACTERISTICS:
                    ( A ) LENGTH: 21 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida krusei ( v i i ) IMMEDIATE SOURCE:
                    ( B ) CLONE: YSASRSUD ( x i ) SEQUENCE DESCRIPTION: SEQ ID NO:163:

GACGGTCTAC CTATGGTAAG C            21

( 2 ) INFORMATION FOR SEQ ID NO:164:

( i ) SEQUENCE CHARACTERISTICS:
                    ( A ) LENGTH: 21 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Candida tropicalis ( v i i ) IMMEDIATE SOURCE:
                    ( B ) CLONE: YSASRRNAB ( x i ) SEQUENCE DESCRIPTION: SEQ ID NO:164:

TCTTCGGACT CTTTGATGAT T            21

( 2 ) INFORMATION FOR SEQ ID NO:165:

( i ) SEQUENCE CHARACTERISTICS:
                    ( A ) LENGTH: 21 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida tropicalis (vii) IMMEDIATE SOURCE:
(B) CLONE: YSASRSUG (xi) SEQUENCE DESCRIPTION: SEQ ID NO:165:

TCTTCGGACT CTTTGATGAT T 21

(2) INFORMATION FOR SEQ ID NO:166:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida viswanathii (vii) IMMEDIATE SOURCE:
(B) CLONE: YSASRSUH (xi) SEQUENCE DESCRIPTION: SEQ ID NO:166:

CCTTCGGGCT CTTTGATGAT T 21

(2) INFORMATION FOR SEQ ID NO:167:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida parapsilosis (vii) IMMEDIATE SOURCE:
(B) CLONE: YSASRSUF (xi) SEQUENCE DESCRIPTION: SEQ ID NO:167:

GGCGATGGTT CATTCAAATT T 21

(2) INFORMATION FOR SEQ ID NO:168:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida guilliermondii (vii) IMMEDIATE SOURCE:
(B) CLONE: YSASRSUC ( x i ) SEQUENCE DESCRIPTION: SEQ ID NO:168:

TCTTTGAGCT CTTTGATGAT T                                            21

( 2 ) INFORMATION FOR SEQ ID NO:169:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:169:

GGTGGTGTTT TTTTAGTGAC C                                            21

( 2 ) INFORMATION FOR SEQ ID NO:170:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Nanochlorum eucaryotum ( v i i ) IMMEDIATE SOURCE:
        ( B ) CLONE: NANRRN18S ( x i ) SEQUENCE DESCRIPTION: SEQ ID NO:170:

GCGGGTGTTT TTTTGATGAC C                                            21

( 2 ) INFORMATION FOR SEQ ID NO:171:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Moraxella sp. MspI ( v i i ) IMMEDIATE SOURCE:
        ( B ) CLONE: MBOMSPI ( x i ) SEQUENCE DESCRIPTION: SEQ ID NO:171:

TCTAGTGTTT CAATGATGAC T                                            21

( 2 ) INFORMATION FOR SEQ ID NO:172:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: E. Coli cvaA,B operon ( v i i ) IMMEDIATE SOURCE:
        ( B ) CLONE: ECOCVAB ( x i ) SEQUENCE DESCRIPTION: SEQ ID NO:172:

GTCGGTGTTT GTGTGATGAT G        21

( 2 ) INFORMATION FOR SEQ ID NO:173:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:173:

GTCTGTGATG CCCTTAG        17

( 2 ) INFORMATION FOR SEQ ID NO:174:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:174:

TGCTGAAAAG CCCCGAC        17

( 2 ) INFORMATION FOR SEQ ID NO:175:

( i ) SEQUENCE CHARACTERISTICS:
        ( A ) LENGTH: 17 bases
        ( B ) TYPE: nucleic acid ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Coccidiodes immitis ( v i i ) IMMEDIATE SOURCE:
            ( B ) CLONE: COIDA ( x i ) SEQUENCE DESCRIPTION: SEQ ID NO:175:

TTCTGGGGAA CCCTAGT 17

( 2 ) INFORMATION FOR SEQ ID NO:176:

( i ) SEQUENCE CHARACTERISTICS:
            ( A ) LENGTH: 17 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Blastomyces dermatitidis ( v i i ) IMMEDIATE SOURCE:
            ( B ) CLONE: BLODA ( x i ) SEQUENCE DESCRIPTION: SEQ ID NO:176:

TCCTGGGAAG CCCCATG 17

( 2 ) INFORMATION FOR SEQ ID NO:177:

( i ) SEQUENCE CHARACTERISTICS:
            ( A ) LENGTH: 17 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Aspergillus fumagatus ( v i i ) IMMEDIATE SOURCE:
            ( B ) CLONE: ASNDA ( x i ) SEQUENCE DESCRIPTION: SEQ ID NO:177:

TTCTGGGGAA CCTCATG 17

( 2 ) INFORMATION FOR SEQ ID NO:178:

( i ) SEQUENCE CHARACTERISTICS:
            ( A ) LENGTH: 17 bases
            ( B ) TYPE: nucleic acid
            ( C ) STRANDEDNESS: single
            ( D ) TOPOLOGY: linear ( i i ) MOLECULE TYPE: cDNA to rRNA (iii) HYPOTHETICAL: NO (iv) ANTI-SENSE: NO (vi) ORIGINAL SOURCE:
 (A) ORGANISM: Aspergillus fumigatus (vii) IMMEDIATE SOURCE:
 (B) CLONE: ASNRR5SS (xi) SEQUENCE DESCRIPTION: SEQ ID NO:178:

TTCTGGGGAA CCTCATG   17

(2) INFORMATION FOR SEQ ID NO:179:

(i) SEQUENCE CHARACTERISTICS:
  (A) LENGTH: 17 bases
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Aspergillus fumigatus (vii) IMMEDIATE SOURCE:
  (B) CLONE: ASNRRSSB (xi) SEQUENCE DESCRIPTION: SEQ ID NO:179:

TTCTGGGGAA CCTCATG   17

(2) INFORMATION FOR SEQ ID NO:180:

(i) SEQUENCE CHARACTERISTICS:
  (A) LENGTH: 17 bases
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Candida albicans (vii) IMMEDIATE SOURCE:
  (B) CLONE: YSASRSUA (xi) SEQUENCE DESCRIPTION: SEQ ID NO:180:

TTCTGGGTAG CCATTTA   17

(2) INFORMATION FOR SEQ ID NO:181:

(i) SEQUENCE CHARACTERISTICS:
  (A) LENGTH: 17 bases
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:

( A ) ORGANISM: Candidi albicans ( v i i ) IMMEDIATE SOURCE:
            ( B ) CLONE: YSAL16S ( x i ) SEQUENCE DESCRIPTION: SEQ ID NO:181:

GTCTGTGATG CCCTTAG        17

( 2 ) INFORMATION FOR SEQ ID NO:182:

( i ) SEQUENCE CHARACTERISTICS:
            ( A ) LENGTH: 17 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida lusitaniae ( v i i ) IMMEDIATE SOURCE:
            ( B ) CLONE: YSASRRNAA ( x i ) SEQUENCE DESCRIPTION: SEQ ID NO:182:

GTCTGTGATG CCCTTAG        17

( 2 ) INFORMATION FOR SEQ ID NO:183:

( i ) SEQUENCE CHARACTERISTICS:
            ( A ) LENGTH: 17 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida lusitaniae ( v i i ) IMMEDIATE SOURCE:
            ( B ) CLONE: YSASRSUE ( x i ) SEQUENCE DESCRIPTION: SEQ ID NO:183:

GTCTGTGATG CCCTTAG        17

( 2 ) INFORMATION FOR SEQ ID NO:184:

( i ) SEQUENCE CHARACTERISTICS:
            ( A ) LENGTH: 17 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida kefyr ( v i i ) IMMEDIATE SOURCE:
            ( B ) CLONE: YSASRSUB (x i) SEQUENCE DESCRIPTION: SEQ ID NO:184:

GTCTGTGATG CCCTTAG 17

(2) INFORMATION FOR SEQ ID NO:185:

(i) SEQUENCE CHARACTERISTICS:
        (A) LENGTH: 17 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida krusei (v i i) IMMEDIATE SOURCE:
        (B) CLONE: YSASRRNAC (x i) SEQUENCE DESCRIPTION: SEQ ID NO:185:

GTCTGTGATG CCCTTAG 17

(2) INFORMATION FOR SEQ ID NO:186:

(i) SEQUENCE CHARACTERISTICS:
        (A) LENGTH: 17 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida krusei (v i i) IMMEDIATE SOURCE:
        (B) CLONE: YSASRSUD (x i) SEQUENCE DESCRIPTION: SEQ ID NO:186:

GTCTGTGATG CCCTTAG 17

(2) INFORMATION FOR SEQ ID NO:187:

(i) SEQUENCE CHARACTERISTICS:
        (A) LENGTH: 17 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida tropicalis (v i i) IMMEDIATE SOURCE:
        (B) CLONE: YSASRRNAB (x i) SEQUENCE DESCRIPTION: SEQ ID NO:187:

GTCTGTGATG CCCTTAG 17

( 2 ) INFORMATION FOR SEQ ID NO:188:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:188:

GTCTGTGATG CCCTTAG        17

( 2 ) INFORMATION FOR SEQ ID NO:189:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:189:

GTCTGTGATG CCCTTAG        17

( 2 ) INFORMATION FOR SEQ ID NO:190:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:190:

GTCTGTGATG CCCTTAG        17

( 2 ) INFORMATION FOR SEQ ID NO:191:

( i ) SEQUENCE CHARACTERISTICS:
        ( A ) LENGTH: 17 bases
        ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida guilliermondii (vii) IMMEDIATE SOURCE:
    (B) CLONE: YSASRSUC (xi) SEQUENCE DESCRIPTION: SEQ ID NO:191:

GTCTGTGATG CCCTTAG                                                                              17

(2) INFORMATION FOR SEQ ID NO:192:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida glabrata (vii) IMMEDIATE SOURCE:
        (B) CLONE: YS5CRRNAS (xi) SEQUENCE DESCRIPTION: SEQ ID NO:192:

GCCTGGGTAG CCGGTCC                                                                              17

(2) INFORMATION FOR SEQ ID NO:193:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Avian influenza (vii) IMMEDIATE SOURCE:
        (B) CLONE: FLAHA5

(xi) SEQUENCE DESCRIPTION: SEQ ID NO:193:

TCCTGGGAAA CCCCATG                                                                              17

(2) INFORMATION FOR SEQ ID NO:194:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Mouse perlecan ( v i i ) IMMEDIATE SOURCE:
    ( B ) CLONE: MUSPERPA ( x i ) SEQUENCE DESCRIPTION: SEQ ID NO:194:

TCCTGGGCAG GCCCATG 17

( 2 ) INFORMATION FOR SEQ ID NO:195:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Mouse basement membrane ( v i i ) IMMEDIATE SOURCE:
        ( B ) CLONE: MUSPGCBMA ( x i ) SEQUENCE DESCRIPTION: SEQ ID NO:195:

TCCTGGGCAG GCCCATG 17

( 2 ) INFORMATION FOR SEQ ID NO:196:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:196:

CGCGGGCTTC TTAGAGGGAC T 21

( 2 ) INFORMATION FOR SEQ ID NO:197:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Cryptococcus neoformans (vii) IMMEDIATE SOURCE:
(B) CLONE: CPCDA (xi) SEQUENCE DESCRIPTION: SEQ ID NO:197:

GGTGAAATTC TTAGATTGAC G　　　　　　　　　　　　　　　　　　　　　　　　　　21

(2) INFORMATION FOR SEQ ID NO:198:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Coccidiodes immitis (vii) IMMEDIATE SOURCE:
(B) CLONE: COIDA (xi) SEQUENCE DESCRIPTION: SEQ ID NO:198:

GACGGGCAAC TTTGAATAAC C　　　　　　　　　　　　　　　　　　　　　　　　　　21

(2) INFORMATION FOR SEQ ID NO:199:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Blastomyces dermatitidis (vii) IMMEDIATE SOURCE:
(B) CLONE: BLODA (xi) SEQUENCE DESCRIPTION: SEQ ID NO:199:

GACGGGGTTC TTATGATGAC C　　　　　　　　　　　　　　　　　　　　　　　　　　21

(2) INFORMATION FOR SEQ ID NO:200:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Aspergillus fumagatus (vii) IMMEDIATE SOURCE:
(B) CLONE: ASNDA ( x i ) SEQUENCE DESCRIPTION: SEQ ID NO:200:

GGCGGTGTTT CTATGATGAC C                                                                                            21

( 2 ) INFORMATION FOR SEQ ID NO:201:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:201:

GGCGGTGTTT CTATGATGAC C                                                                                            21

( 2 ) INFORMATION FOR SEQ ID NO:202:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:202:

GGCGGTGTTT CTATGATGAC C                                                                                            21

( 2 ) INFORMATION FOR SEQ ID NO:203:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:203:

GTTGTTGTTC TTTTATTGAC G                                                                                            21

(2) INFORMATION FOR SEQ ID NO:204:

(i) SEQUENCE CHARACTERISTICS:
  (A) LENGTH: 21 bases
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Candidi albicans (vii) IMMEDIATE SOURCE:
  (B) CLONE: YSAL16S (xi) SEQUENCE DESCRIPTION: SEQ ID NO:204:

GTTGTTGTTC TTTTATTGAC G  21

(2) INFORMATION FOR SEQ ID NO:205:

(i) SEQUENCE CHARACTERISTICS:
  (A) LENGTH: 21 bases
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Candida lusitaniae (vii) IMMEDIATE SOURCE:
  (B) CLONE: YSASRRNAA (xi) SEQUENCE DESCRIPTION: SEQ ID NO:205:

GGCGGCGTTC ATTTAGTGAC G  21

(2) INFORMATION FOR SEQ ID NO:206:

(i) SEQUENCE CHARACTERISTICS:
  (A) LENGTH: 21 bases
  (B) TYPE: nucleic acid
  (C) STRANDEDNESS: single
  (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Candida lusitaniae (vii) IMMEDIATE SOURCE:
  (B) CLONE: YSASRSUE (xi) SEQUENCE DESCRIPTION: SEQ ID NO:206:

GGCGGCGTTC ATTTAGTGAC G  21

(2) INFORMATION FOR SEQ ID NO:207:

(i) SEQUENCE CHARACTERISTICS:
  (A) LENGTH: 21 bases
  (B) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida kefyr ( v i i ) IMMEDIATE SOURCE:
    ( B ) CLONE: YSASRSUB ( x i ) SEQUENCE DESCRIPTION: SEQ ID NO:207:

GGTGGTGTTT TTCTTATGAC C     21

( 2 ) INFORMATION FOR SEQ ID NO:208:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida krusei ( v i i ) IMMEDIATE SOURCE:
    ( B ) CLONE: YSASRRNAC ( x i ) SEQUENCE DESCRIPTION: SEQ ID NO:208:

GACGGTCTAC CTATGGTAAG C     21

( 2 ) INFORMATION FOR SEQ ID NO:209:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida krusei ( v i i ) IMMEDIATE SOURCE:
    ( B ) CLONE: YSASRSUD ( x i ) SEQUENCE DESCRIPTION: SEQ ID NO:209:

GACGGTCTAC CTATGGTAAG C     21

( 2 ) INFORMATION FOR SEQ ID NO:210:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: cDNA to rRNA (i i i) HYPOTHETICAL: NO (i v) ANTI-SENSE: NO (v i) ORIGINAL SOURCE:
    (A) ORGANISM: Candida tropicalis (v i i) IMMEDIATE SOURCE:
    (B) CLONE: YSASRRNAB (x i) SEQUENCE DESCRIPTION: SEQ ID NO:210:

GTTGTTGTTC TTTTATTGAC G    21

(2) INFORMATION FOR SEQ ID NO:211:

(i) SEQUENCE CHARACTERISTICS:
        (A) LENGTH: 21 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida tropicalis (v i i) IMMEDIATE SOURCE:
        (B) CLONE: YSASRSUG (x i) SEQUENCE DESCRIPTION: SEQ ID NO:211:

GTTGTTGTTC TTTTATTGAC G    21

(2) INFORMATION FOR SEQ ID NO:212:

(i) SEQUENCE CHARACTERISTICS:
        (A) LENGTH: 21 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida viswanathii (v i i) IMMEDIATE SOURCE:
        (B) CLONE: YSASRSUH (x i) SEQUENCE DESCRIPTION: SEQ ID NO:212:

GTTGTTGTTC TTTTATTGAC G    21

(2) INFORMATION FOR SEQ ID NO:213:

(i) SEQUENCE CHARACTERISTICS:
        (A) LENGTH: 21 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:

(A) ORGANISM: Candida parapsilosis (vii) IMMEDIATE SOURCE:
(B) CLONE: YSASRSUF (xi) SEQUENCE DESCRIPTION: SEQ ID NO:213:

GTTGTTGTTC TTTTATTGAC G   21

(2) INFORMATION FOR SEQ ID NO:214:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida guilliermondii (vii) IMMEDIATE SOURCE:
(B) CLONE: YSASRSUC (xi) SEQUENCE DESCRIPTION: SEQ ID NO:214:

GGTGTTGTTC TKTTTTTGAC G   21

(2) INFORMATION FOR SEQ ID NO:215:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida glabrata (vii) IMMEDIATE SOURCE:
(B) CLONE: YS5CRRNAS (xi) SEQUENCE DESCRIPTION: SEQ ID NO:215:

GGTGGTGTTT TTTTAGTGAC C   21

(2) INFORMATION FOR SEQ ID NO:216:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Rat ITPR2 Type 2 inositol (vii) IMMEDIATE SOURCE:
(B) CLONE: RATITPR2R ( x i ) SEQUENCE DESCRIPTION: SEQ ID NO:216:

GACGGGGTTC CCACTATGAC C 21

( 2 ) INFORMATION FOR SEQ ID NO:217:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Canine mRNA ( v i i ) IMMEDIATE SOURCE:
        ( B ) CLONE: DOGSRPR ( x i ) SEQUENCE DESCRIPTION: SEQ ID NO:217:

CTGCTAATTC TTATGATGAC C 21

( 2 ) INFORMATION FOR SEQ ID NO:218:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Mitochondrion Oenothera ( v i i ) IMMEDIATE SOURCE:
        ( B ) CLONE: OBEMTNAD12

( x i ) SEQUENCE DESCRIPTION: SEQ ID NO:218:

CAGTCTTTTC TTATGATGAC C 21

( 2 ) INFORMATION FOR SEQ ID NO:219:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:219:

TTTCTGGANA AGTTGATC 18

( 2 ) INFORMATION FOR SEQ ID NO:220:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Cryptococcus neoformans ( v i i ) IMMEDIATE SOURCE:
    ( B ) CLONE: CPCDA ( x i ) SEQUENCE DESCRIPTION: SEQ ID NO:220:

TGTCTGAGNC CAGCGAGT                                                        18

( 2 ) INFORMATION FOR SEQ ID NO:221:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Coccidiodes immitis ( v i i ) IMMEDIATE SOURCE:
    ( B ) CLONE: COIDA ( x i ) SEQUENCE DESCRIPTION: SEQ ID NO:221:

GGTCTGGCNT CAGGGAGG                                                        18

( 2 ) INFORMATION FOR SEQ ID NO:222:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Blastomyces dermatitidis ( v i i ) IMMEDIATE SOURCE:
    ( B ) CLONE: BLODA ( x i ) SEQUENCE DESCRIPTION: SEQ ID NO:222:

GCTCTGGTNC CGGCCGGA                                                        18

( 2 ) INFORMATION FOR SEQ ID NO:223:

( i ) SEQUENCE CHARACTERISTICS:
    ( A ) LENGTH: 18 bases
    ( B ) TYPE: nucleic acid ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Aspergillus fumagatus ( v i i ) IMMEDIATE SOURCE:
                    ( B ) CLONE: ASNDA ( x i ) SEQUENCE DESCRIPTION: SEQ ID NO:223:

GGTCTGGCNT CAGGGGAG 18

( 2 ) INFORMATION FOR SEQ ID NO:224:

( i ) SEQUENCE CHARACTERISTICS:
                    ( A ) LENGTH: 18 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Aspergillus fumigatus ( v i i ) IMMEDIATE SOURCE:
                    ( B ) CLONE: ASNRR5SS ( x i ) SEQUENCE DESCRIPTION: SEQ ID NO:224:

GGTCTGGCNT CAGGGGAG 18

( 2 ) INFORMATION FOR SEQ ID NO:225:

( i ) SEQUENCE CHARACTERISTICS:
                    ( A ) LENGTH: 18 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Aspergillus fumigatus ( v i i ) IMMEDIATE SOURCE:
                    ( B ) CLONE: ASNRRSSB ( x i ) SEQUENCE DESCRIPTION: SEQ ID NO:225:

GGTCTGGCNT CAGGGGAG 18

( 2 ) INFORMATION FOR SEQ ID NO:226:

( i ) SEQUENCE CHARACTERISTICS:
                    ( A ) LENGTH: 18 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida albicans ( v i i ) IMMEDIATE SOURCE:
    ( B ) CLONE: YSASRSUA ( x i ) SEQUENCE DESCRIPTION: SEQ ID NO:226:

GTTCTGGACC CAGCCGAG 18

( 2 ) INFORMATION FOR SEQ ID NO:227:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candidi albicans ( v i i ) IMMEDIATE SOURCE:
        ( B ) CLONE: YSAL16S ( x i ) SEQUENCE DESCRIPTION: SEQ ID NO:227:

GTTCTGGANC CAGCCGAG 18

( 2 ) INFORMATION FOR SEQ ID NO:228:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:228:

GATTTGTCNT AAGCCGAG 18

( 2 ) INFORMATION FOR SEQ ID NO:229:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida lusitaniae (vii) IMMEDIATE SOURCE:
    (B) CLONE: YSASRSUE (xi) SEQUENCE DESCRIPTION: SEQ ID NO:229:

GATTTGTCNT AAGCCGAG 18

(2) INFORMATION FOR SEQ ID NO:230:

(i) SEQUENCE CHARACTERISTICS:
    (A) LENGTH: 18 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida kefyr (vii) IMMEDIATE SOURCE:
    (B) CLONE: YSASRSUB (xi) SEQUENCE DESCRIPTION: SEQ ID NO:230:

TGTCGGAGNC CAGCGAGT 18

(2) INFORMATION FOR SEQ ID NO:231:

(i) SEQUENCE CHARACTERISTICS:
    (A) LENGTH: 18 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida krusei (vii) IMMEDIATE SOURCE:
    (B) CLONE: YSASRRNAC (xi) SEQUENCE DESCRIPTION: SEQ ID NO:231:

GCTCTGTTNG CGGCCGGG 18

(2) INFORMATION FOR SEQ ID NO:232:

(i) SEQUENCE CHARACTERISTICS:
    (A) LENGTH: 18 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida krusei (vii) IMMEDIATE SOURCE:
    (B) CLONE: YSASRSUD ( x i ) SEQUENCE DESCRIPTION: SEQ ID NO:232:

GCTCTGTTNG CGGCCGGG 18

( 2 ) INFORMATION FOR SEQ ID NO:233:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:233:

GTTCTGGACC CAACCGAG 18

( 2 ) INFORMATION FOR SEQ ID NO:234:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:234:

GTTCTGGACC CAACCGAG 18

( 2 ) INFORMATION FOR SEQ ID NO:235:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:235:

GTTCTGGACC CAACCGAG 18

( 2 ) INFORMATION FOR SEQ ID NO:236:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:236:

GTTCTGGACC CAGCCGAG         18

( 2 ) INFORMATION FOR SEQ ID NO:237:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:237:

GTTCTGGACC CAACCGAG         18

( 2 ) INFORMATION FOR SEQ ID NO:238:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:238:

GTTCTGGANA TGCACCCG         18

( 2 ) INFORMATION FOR SEQ ID NO:239:

( i ) SEQUENCE CHARACTERISTICS:
        ( A ) LENGTH: 18 bases
        ( B ) TYPE: nucleic acid ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: A. vinelandii major nif ( v i i ) IMMEDIATE SOURCE:
            ( B ) CLONE: AVINIFC ( x i ) SEQUENCE DESCRIPTION: SEQ ID NO:239:

GTTCTGGANC CAGCCAGG 18

( 2 ) INFORMATION FOR SEQ ID NO:240:

( i ) SEQUENCE CHARACTERISTICS:
            ( A ) LENGTH: 18 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Mouse MHC II A beta ( v i i ) IMMEDIATE SOURCE:
            ( B ) CLONE: MUSMHABMO8

( x i ) SEQUENCE DESCRIPTION: SEQ ID NO:240:

GTTCTGGANC CAGCCAGC 18

( 2 ) INFORMATION FOR SEQ ID NO:241:

( i ) SEQUENCE CHARACTERISTICS:
            ( A ) LENGTH: 18 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Human DRB1 transplant ( v i i ) IMMEDIATE SOURCE:
            ( B ) CLONE: HUMDRB1L ( x i ) SEQUENCE DESCRIPTION: SEQ ID NO:241:

GTTCTGGANA CAGCCGGA 18

( 2 ) INFORMATION FOR SEQ ID NO:242:

( i ) SEQUENCE CHARACTERISTICS:
            ( A ) LENGTH: 23 bases
            ( B ) TYPE: nucleic acid
            ( C ) STRANDEDNESS: single
            ( D ) TOPOLOGY: linear ( i i ) MOLECULE TYPE: cDNA to rRNA (i i i) HYPOTHETICAL: NO (i v) ANTI-SENSE: NO (v i) ORIGINAL SOURCE:
    (A) ORGANISM: Pneumocystis carinii (v i i) IMMEDIATE SOURCE:
    (B) CLONE: PMC16SRR1

(x i) SEQUENCE DESCRIPTION: SEQ ID NO:242:

TAGTATTCAA TTGTCNAGAG GTG    23

(2) INFORMATION FOR SEQ ID NO:243:

(i) SEQUENCE CHARACTERISTICS:
        (A) LENGTH: 23 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Cryptococcus neoformans (v i i) IMMEDIATE SOURCE:
        (B) CLONE: CPCDA (x i) SEQUENCE DESCRIPTION: SEQ ID NO:243:

GTTAATTCCG ATAACGAACG AGA    23

(2) INFORMATION FOR SEQ ID NO:244:

(i) SEQUENCE CHARACTERISTICS:
        (A) LENGTH: 23 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Coccidiodes immitis (v i i) IMMEDIATE SOURCE:
        (B) CLONE: COIDA (x i) SEQUENCE DESCRIPTION: SEQ ID NO:244:

TAGTATTCGG CTGTCNAGAG GTG    23

(2) INFORMATION FOR SEQ ID NO:245:

(i) SEQUENCE CHARACTERISTICS:
        (A) LENGTH: 23 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:

(A) ORGANISM: Blastomyces dermatitidis (vii) IMMEDIATE SOURCE:
                (B) CLONE: BLODA (xi) SEQUENCE DESCRIPTION: SEQ ID NO:245:

TAGTATTCGG CTGTCNAGAG GTG                                                          23

(2) INFORMATION FOR SEQ ID NO:246:

(i) SEQUENCE CHARACTERISTICS:
                (A) LENGTH: 23 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Aspergillus fumagatus (vii) IMMEDIATE SOURCE:
                (B) CLONE: ASNDA (xi) SEQUENCE DESCRIPTION: SEQ ID NO:246:

TAGTATTCAG CTGTCNAGAG GTG                                                          23

(2) INFORMATION FOR SEQ ID NO:247:

(i) SEQUENCE CHARACTERISTICS:
                (A) LENGTH: 23 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Aspergillus fumigatus (vii) IMMEDIATE SOURCE:
                (B) CLONE: ASNRR5SS (xi) SEQUENCE DESCRIPTION: SEQ ID NO:247:

TAGTATTCAG CTGTCNAGAG GTG                                                          23

(2) INFORMATION FOR SEQ ID NO:248:

(i) SEQUENCE CHARACTERISTICS:
                (A) LENGTH: 23 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Aspergillus fumigatus (vii) IMMEDIATE SOURCE:
                (B) CLONE: ASNRRSSB ( x i ) SEQUENCE DESCRIPTION: SEQ ID NO:248:

TAGTATTCAG CTGTCNAGAG GTG                                                                          23

( 2 ) INFORMATION FOR SEQ ID NO:249:

( i ) SEQUENCE CHARACTERISTICS:
           ( A ) LENGTH: 23 bases
           ( B ) TYPE: nucleic acid
           ( C ) STRANDEDNESS: single
           ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
           ( A ) ORGANISM: Candida albicans ( v i i ) IMMEDIATE SOURCE:
           ( B ) CLONE: YSASRSUA ( x i ) SEQUENCE DESCRIPTION: SEQ ID NO:249:

TAGTATTCAG TTGTCNAGAG GTG                                                                          23

( 2 ) INFORMATION FOR SEQ ID NO:250:

( i ) SEQUENCE CHARACTERISTICS:
           ( A ) LENGTH: 23 bases
           ( B ) TYPE: nucleic acid
           ( C ) STRANDEDNESS: single
           ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
           ( A ) ORGANISM: Candidi albicans ( v i i ) IMMEDIATE SOURCE:
           ( B ) CLONE: YSAL16S ( x i ) SEQUENCE DESCRIPTION: SEQ ID NO:250:

TAGTATTCAG ATGTCGAGAA GTG                                                                          23

( 2 ) INFORMATION FOR SEQ ID NO:251:

( i ) SEQUENCE CHARACTERISTICS:
           ( A ) LENGTH: 23 bases
           ( B ) TYPE: nucleic acid
           ( C ) STRANDEDNESS: single
           ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
           ( A ) ORGANISM: Candida lusitaniae ( v i i ) IMMEDIATE SOURCE:
           ( B ) CLONE: YSASRRNAA ( x i ) SEQUENCE DESCRIPTION: SEQ ID NO:251:

TAGTATTCAG TTGTCNAGAG GTG                                                                          23

( 2 ) INFORMATION FOR SEQ ID NO:252:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:252:

TAGTATTCAG TTGTCNAGAG GTG     23

( 2 ) INFORMATION FOR SEQ ID NO:253:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:253:

TAGTATTCAA TTGTCNAGAG GTG     23

( 2 ) INFORMATION FOR SEQ ID NO:254:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:254:

TAGTATTCAG TCGTCNAGAG GTG     23

( 2 ) INFORMATION FOR SEQ ID NO:255:

( i ) SEQUENCE CHARACTERISTICS:
        ( A ) LENGTH: 23 bases
        ( B ) TYPE: nucleic acid ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida krusei ( v i i ) IMMEDIATE SOURCE:
            ( B ) CLONE: YSASRSUD ( x i ) SEQUENCE DESCRIPTION: SEQ ID NO:255:

TAGTATTCAG TCGTCNAGAG GTG  23

( 2 ) INFORMATION FOR SEQ ID NO:256:

( i ) SEQUENCE CHARACTERISTICS:
            ( A ) LENGTH: 23 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida tropicalis ( v i i ) IMMEDIATE SOURCE:
            ( B ) CLONE: YSASRRNAB ( x i ) SEQUENCE DESCRIPTION: SEQ ID NO:256:

TAGTATTCAG TTGTCNAGAG GTG  23

( 2 ) INFORMATION FOR SEQ ID NO:257:

( i ) SEQUENCE CHARACTERISTICS:
            ( A ) LENGTH: 23 bases
            ( B ) TYPE: nucleic acid
            ( C ) STRANDEDNESS: single
            ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
            ( A ) ORGANISM: Candida tropicalis ( v i i ) IMMEDIATE SOURCE:
            ( B ) CLONE: YSASRSUG ( x i ) SEQUENCE DESCRIPTION: SEQ ID NO:257:

TAGTATTCAG TTGTCNAGAG GTG  23

( 2 ) INFORMATION FOR SEQ ID NO:258:

( i ) SEQUENCE CHARACTERISTICS:
            ( A ) LENGTH: 23 bases
            ( B ) TYPE: nucleic acid
            ( C ) STRANDEDNESS: single
            ( D ) TOPOLOGY: linear ( i i ) MOLECULE TYPE: cDNA to rRNA (iii) HYPOTHETICAL: NO (iv) ANTI-SENSE: NO (vi) ORIGINAL SOURCE:
    (A) ORGANISM: Candida viswanathii (vii) IMMEDIATE SOURCE:
    (B) CLONE: YSASRSUH (xi) SEQUENCE DESCRIPTION: SEQ ID NO:258:

TAGTATTCAG TTGTCNAGAG GTG  23

(2) INFORMATION FOR SEQ ID NO:259:

(i) SEQUENCE CHARACTERISTICS:
    (A) LENGTH: 23 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida parapsilosis (vii) IMMEDIATE SOURCE:
    (B) CLONE: YSASRSUF (xi) SEQUENCE DESCRIPTION: SEQ ID NO:259:

TAGTATTCAG TAGTCNAGAG GTG  23

(2) INFORMATION FOR SEQ ID NO:260:

(i) SEQUENCE CHARACTERISTICS:
    (A) LENGTH: 23 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida guilliermondii (vii) IMMEDIATE SOURCE:
    (B) CLONE: YSASRSUC (xi) SEQUENCE DESCRIPTION: SEQ ID NO:260:

TAGTATTCAG TTGTCNAGAG GTG  23

(2) INFORMATION FOR SEQ ID NO:261:

(i) SEQUENCE CHARACTERISTICS:
    (A) LENGTH: 23 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:

(A) ORGANISM: Candida glabrata (vii) IMMEDIATE SOURCE:
(B) CLONE: YS5CRRNAS (xi) SEQUENCE DESCRIPTION: SEQ ID NO:261:

TAGTATTCAA TTGTCNAGAG GTG 23

(2) INFORMATION FOR SEQ ID NO:262:

(i) SEQUENCE CHARACTERISTICS:
(A) LENGTH: 23 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Vesicular stomatitis (vii) IMMEDIATE SOURCE:
(B) CLONE: VSVGPNJAD (xi) SEQUENCE DESCRIPTION: SEQ ID NO:262:

TTGATATCAG ATGTCGAAAG GAT 23

(2) INFORMATION FOR SEQ ID NO:263:

(i) SEQUENCE CHARACTERISTICS:
(A) LENGTH: 23 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Vesicular stomatis (vii) IMMEDIATE SOURCE:
(B) CLONE: VSVGPNJAC (xi) SEQUENCE DESCRIPTION: SEQ ID NO:263:

TTGATATCAG ATGTCGAAAG GAT 23

(2) INFORMATION FOR SEQ ID NO:264:

(i) SEQUENCE CHARACTERISTICS:
(A) LENGTH: 23 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Human glutatione S- tra.

(vii) IMMEDIATE SOURCE:
(B) CLONE: HUMGSTPIA ( x i ) SEQUENCE DESCRIPTION: SEQ ID NO:264:

TTTTATTCAG AAGTAGAAAG GGA  23

( 2 ) INFORMATION FOR SEQ ID NO:265:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:265:

CTTCGCGGAT CGCATGG  17

( 2 ) INFORMATION FOR SEQ ID NO:266:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Cryptococcus neoformans ( v i i ) IMMEDIATE SOURCE:
        ( B ) CLONE: CPCDA ( x i ) SEQUENCE DESCRIPTION: SEQ ID NO:266:

CCTCACGGAG TGCACTG  17

( 2 ) INFORMATION FOR SEQ ID NO:267:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:267:

CTTCGCGGCG TGCACTG  17

( 2 ) INFORMATION FOR SEQ ID NO:268:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:268:

CCTCACCGCG TGCACTG 17

( 2 ) INFORMATION FOR SEQ ID NO:269:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:269:

CCTCATGGCC TTCACTG 17

( 2 ) INFORMATION FOR SEQ ID NO:270:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:270:

CCTCATGGCC TTCACTG 17

( 2 ) INFORMATION FOR SEQ ID NO:271:

( i ) SEQUENCE CHARACTERISTICS:
        ( A ) LENGTH: 17 bases
        ( B ) TYPE: nucleic acid (C) STRANDEDNESS: single
(D) TOPOLOGY: linear (i i) MOLECULE TYPE: cDNA to rRNA (i i i) HYPOTHETICAL: NO (i v) ANTI-SENSE: NO (v i) ORIGINAL SOURCE:
    (A) ORGANISM: Aspergillus fumigatus (v i i) IMMEDIATE SOURCE:
    (B) CLONE: ASNRRSSB (x i) SEQUENCE DESCRIPTION: SEQ ID NO:271:

CCTCATGGCC TTCACTG                    17

(2) INFORMATION FOR SEQ ID NO:272:

(i) SEQUENCE CHARACTERISTICS:
    (A) LENGTH: 17 bases
    (B) TYPE: nucleic acid
    (C) STRANDEDNESS: single
    (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
    (A) ORGANISM: Candida albicans (v i i) IMMEDIATE SOURCE:
    (B) CLONE: YSASRSUA (x i) SEQUENCE DESCRIPTION: SEQ ID NO:272:

GCACGCGCGC TACACTG                    17

(2) INFORMATION FOR SEQ ID NO:273:

(i) SEQUENCE CHARACTERISTICS:
    (A) LENGTH: 17 bases
    (B) TYPE: nucleic acid
    (C) STRANDEDNESS: single
    (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
    (A) ORGANISM: Candidi albicans (v i i) IMMEDIATE SOURCE:
    (B) CLONE: YSAL16S (x i) SEQUENCE DESCRIPTION: SEQ ID NO:273:

GCACGCGCGC TACACTG                    17

(2) INFORMATION FOR SEQ ID NO:274:

(i) SEQUENCE CHARACTERISTICS:
    (A) LENGTH: 17 bases
    (B) TYPE: nucleic acid
    (C) STRANDEDNESS: single
    (D) TOPOLOGY: linear (i i) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida lusitaniae ( v i i ) IMMEDIATE SOURCE:
    ( B ) CLONE: YSASRRNAA ( x i ) SEQUENCE DESCRIPTION: SEQ ID NO:274:

CGCTTAGGCG AGCACTG                                                                                               17

( 2 ) INFORMATION FOR SEQ ID NO:275:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:275:

TNGTCTGGCG CGCNCTT                                                                                         17

( 2 ) INFORMATION FOR SEQ ID NO:276:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:276:

GCACGCGCGC TACACTG                                                                                     17

( 2 ) INFORMATION FOR SEQ ID NO:277:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

( A ) ORGANISM: Candida krusei ( v i i ) IMMEDIATE SOURCE:
            ( B ) CLONE: YSASRRNAC ( x i ) SEQUENCE DESCRIPTION: SEQ ID NO:277:

GCACGCGCGC TACACTG                                                                17

( 2 ) INFORMATION FOR SEQ ID NO:278:

( i ) SEQUENCE CHARACTERISTICS:
                ( A ) LENGTH: 17 bases
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Candida krusei ( v i i ) IMMEDIATE SOURCE:
                ( B ) CLONE: YSASRSUD ( x i ) SEQUENCE DESCRIPTION: SEQ ID NO:278:

GCACGCGCGC TACACTG                                                                17

( 2 ) INFORMATION FOR SEQ ID NO:279:

( i ) SEQUENCE CHARACTERISTICS:
                ( A ) LENGTH: 17 bases
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Candida tropicalis ( v i i ) IMMEDIATE SOURCE:
                ( B ) CLONE: YSASRRNAB ( x i ) SEQUENCE DESCRIPTION: SEQ ID NO:279:

GCACGCGCGC TACACTG                                                                17

( 2 ) INFORMATION FOR SEQ ID NO:280:

( i ) SEQUENCE CHARACTERISTICS:
                ( A ) LENGTH: 17 bases
                ( B ) TYPE: nucleic acid
                ( C ) STRANDEDNESS: single
                ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                ( A ) ORGANISM: Candida tropicalis ( v i i ) IMMEDIATE SOURCE:
                ( B ) CLONE: YSASRSUG ( x i ) SEQUENCE DESCRIPTION: SEQ ID NO:280:

GCACGCGCGC TACACTG                                                                                          17

( 2 ) INFORMATION FOR SEQ ID NO:281:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:281:

GCACGCGCGC TACACTG                                                                                          17

( 2 ) INFORMATION FOR SEQ ID NO:282:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:282:

GCACGCGCGC TACACTG                                                                                          17

( 2 ) INFORMATION FOR SEQ ID NO:283:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:283:

CTTTTTGGCG AGTACTG                                                                                          17

( 2 ) INFORMATION FOR SEQ ID NO:284:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:284:

CTTGGCGGCG AACCAGG         17

( 2 ) INFORMATION FOR SEQ ID NO:285:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Rabbit progest. recept ( v i i ) IMMEDIATE SOURCE:
        ( B ) CLONE: RABPRG1

( x i ) SEQUENCE DESCRIPTION: SEQ ID NO:285:

CTTCGCAGCG TGCACGG         17

( 2 ) INFORMATION FOR SEQ ID NO:286:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Streptomyces lividans 66

( v i i ) IMMEDIATE SOURCE:
        ( B ) CLONE: STMTRNGM ( x i ) SEQUENCE DESCRIPTION: SEQ ID NO:286:

CTTCGCCGCG TGCACGA         17

( 2 ) INFORMATION FOR SEQ ID NO:287:

( i ) SEQUENCE CHARACTERISTICS:
        ( A ) LENGTH: 17 bases
        ( B ) TYPE: nucleic acid (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Human mRNA cysteine (vii) IMMEDIATE SOURCE:
                (B) CLONE: HUMCYSTCR (xi) SEQUENCE DESCRIPTION: SEQ ID NO:287:

GTGTGCGGCG TGCACTG 17

(2) INFORMATION FOR SEQ ID NO:288:

(i) SEQUENCE CHARACTERISTICS:
                (A) LENGTH: 22 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Pneumocystis carinii (vii) IMMEDIATE SOURCE:
                (B) CLONE: PMC16SRR1

(xi) SEQUENCE DESCRIPTION: SEQ ID NO:288:

TTACTACTTG GATAACCGTG GT 22

(2) INFORMATION FOR SEQ ID NO:289:

(i) SEQUENCE CHARACTERISTICS:
                (A) LENGTH: 22 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
                (A) ORGANISM: Cryptococcus neoformans (vii) IMMEDIATE SOURCE:
                (B) CLONE: CPCDA (xi) SEQUENCE DESCRIPTION: SEQ ID NO:289:

CTGCCCTTTG TACACACCGC CC 22

(2) INFORMATION FOR SEQ ID NO:290:

(i) SEQUENCE CHARACTERISTICS:
                (A) LENGTH: 22 bases
                (B) TYPE: nucleic acid
                (C) STRANDEDNESS: single
                (D) TOPOLOGY: linear (ii) MOLECULE TYPE: cDNA to rRNA (iii) HYPOTHETICAL: NO (iv) ANTI-SENSE: NO (vi) ORIGINAL SOURCE:
  (A) ORGANISM: Coccidiodes immitis (vii) IMMEDIATE SOURCE:
  (B) CLONE: COIDA (xi) SEQUENCE DESCRIPTION: SEQ ID NO:290:

GGCAACTTTG AATAACCCGT TC    22

(2) INFORMATION FOR SEQ ID NO:291:

(i) SEQUENCE CHARACTERISTICS:
    (A) LENGTH: 22 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Blastomyces dermatitidis (vii) IMMEDIATE SOURCE:
    (B) CLONE: BLODA (xi) SEQUENCE DESCRIPTION: SEQ ID NO:291:

GGGTTCTTAT GATGACCCGT TC    22

(2) INFORMATION FOR SEQ ID NO:292:

(i) SEQUENCE CHARACTERISTICS:
    (A) LENGTH: 22 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Aspergillus fumagatus (vii) IMMEDIATE SOURCE:
    (B) CLONE: ASNDA (xi) SEQUENCE DESCRIPTION: SEQ ID NO:292:

CTGCCCTTTG TACACACCGC CC    22

(2) INFORMATION FOR SEQ ID NO:293:

(i) SEQUENCE CHARACTERISTICS:
    (A) LENGTH: 22 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:

(A) ORGANISM: Aspergillus fumigatus (vii) IMMEDIATE SOURCE:
   (B) CLONE: ASNRR5SS (xi) SEQUENCE DESCRIPTION: SEQ ID NO:293:

TTCAACGTGG AATGCCTAGT AG    22

(2) INFORMATION FOR SEQ ID NO:294:

(i) SEQUENCE CHARACTERISTICS:
      (A) LENGTH: 22 bases
      (B) TYPE: nucleic acid
      (C) STRANDEDNESS: single
      (D) TOPOLOGY: linear (ii) MOLECULE TYPE: cDNA to rRNA (iii) HYPOTHETICAL: NO (iv) ANTI-SENSE: NO (vi) ORIGINAL SOURCE:
      (A) ORGANISM: Aspergillus fumigatus (vii) IMMEDIATE SOURCE:
      (B) CLONE: ASNRRSSB (xi) SEQUENCE DESCRIPTION: SEQ ID NO:294:

TTCAACGTGG AATGCCTAGT AG    22

(2) INFORMATION FOR SEQ ID NO:295:

(i) SEQUENCE CHARACTERISTICS:
      (A) LENGTH: 22 bases
      (B) TYPE: nucleic acid
      (C) STRANDEDNESS: single
      (D) TOPOLOGY: linear (ii) MOLECULE TYPE: cDNA to rRNA (iii) HYPOTHETICAL: NO (iv) ANTI-SENSE: NO (vi) ORIGINAL SOURCE:
      (A) ORGANISM: Candida albicans (vii) IMMEDIATE SOURCE:
      (B) CLONE: YSASRSUA (xi) SEQUENCE DESCRIPTION: SEQ ID NO:295:

TTACTACTTG GATAACCGTG GT    22

(2) INFORMATION FOR SEQ ID NO:296:

(i) SEQUENCE CHARACTERISTICS:
      (A) LENGTH: 22 bases
      (B) TYPE: nucleic acid
      (C) STRANDEDNESS: single
      (D) TOPOLOGY: linear (ii) MOLECULE TYPE: cDNA to rRNA (iii) HYPOTHETICAL: NO (iv) ANTI-SENSE: NO (vi) ORIGINAL SOURCE:
      (A) ORGANISM: Candidi albicans (vii) IMMEDIATE SOURCE:
      (B) CLONE: YSAL16S ( x i ) SEQUENCE DESCRIPTION: SEQ ID NO:296:

TTACTACTTG GATAACCGTG GT 22

( 2 ) INFORMATION FOR SEQ ID NO:297:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRRNAA ( x i ) SEQUENCE DESCRIPTION: SEQ ID NO:297:

TGTTACTTTG AGTAAATGAG AG 22

( 2 ) INFORMATION FOR SEQ ID NO:298:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida lusitaniae ( v i i ) IMMEDIATE SOURCE:
        ( B ) CLONE: YSASRSUE ( x i ) SEQUENCE DESCRIPTION: SEQ ID NO:298:

TGTTACTTTG AGTAAATGAG AG 22

( 2 ) INFORMATION FOR SEQ ID NO:299:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:299:

TTTTACTTTG AAAAAATTAG AG 22

( 2 ) INFORMATION FOR SEQ ID NO:300:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:300:

GGCAACTTTC CCATGGGGCC GA     22

( 2 ) INFORMATION FOR SEQ ID NO:301:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:301:

GGCAACTTTC CCATGGGGCC GA     22

( 2 ) INFORMATION FOR SEQ ID NO:302:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:302:

TTACTACTTG GATAACCGTG GT     22

( 2 ) INFORMATION FOR SEQ ID NO:303:

( i ) SEQUENCE CHARACTERISTICS:
        ( A ) LENGTH: 22 bases
        ( B ) TYPE: nucleic acid ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:303:

TTACTACTTG GATAACCGTG GT 22

( 2 ) INFORMATION FOR SEQ ID NO:304:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:304:

TTACTACTTG GATAACCGTG GT 22

( 2 ) INFORMATION FOR SEQ ID NO:305:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida parapsilosis ( v i i ) IMMEDIATE SOURCE:
        ( B ) CLONE: YSASRSUF ( x i ) SEQUENCE DESCRIPTION: SEQ ID NO:305:

TTACTACTTG GATAACCGTG GT 22

( 2 ) INFORMATION FOR SEQ ID NO:306:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA (i i i) HYPOTHETICAL: NO (i v) ANTI-SENSE: NO (v i) ORIGINAL SOURCE:
                (A) ORGANISM: Candida guillicrmondii (v i i) IMMEDIATE SOURCE:
                (B) CLONE: YSASRSUC (x i) SEQUENCE DESCRIPTION: SEQ ID NO:306:

TTACTACTTG GATAACCGTG GT                                                                22

(2) INFORMATION FOR SEQ ID NO:307:

(i) SEQUENCE CHARACTERISTICS:
                (A) LENGTH: 22 bases
                (B) TYPE: nucleic acid
                (C) STRANDEDNESS: single
                (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
                (A) ORGANISM: Candida glabrata (v i i) IMMEDIATE SOURCE:
                (B) CLONE: YS5CRRNAS (x i) SEQUENCE DESCRIPTION: SEQ ID NO:307:

TTTTACTTTG AAAAAATTAG AG                                                                22

(2) INFORMATION FOR SEQ ID NO:308:

(i) SEQUENCE CHARACTERISTICS:
                (A) LENGTH: 22 bases
                (B) TYPE: nucleic acid
                (C) STRANDEDNESS: single
                (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
                (A) ORGANISM: Genome bacteriophage T7

(v i i) IMMEDIATE SOURCE:
                (B) CLONE: PT7DOT7

(x i) SEQUENCE DESCRIPTION: SEQ ID NO:308:

GGACTTCTTG AATAACCCGT TC                                                                22

(2) INFORMATION FOR SEQ ID NO:309:

(i) SEQUENCE CHARACTERISTICS:
                (A) LENGTH: 22 bases
                (B) TYPE: nucleic acid
                (C) STRANDEDNESS: single
                (D) TOPOLOGY: linear (i i) MOLECULE TYPE: cDNA to rRNA (i i i) HYPOTHETICAL: NO (i v) ANTI-SENSE: NO (v i) ORIGINAL SOURCE:

(A) ORGANISM: Bacteriophage T7, comple.

(vii) IMMEDIATE SOURCE:
    (B) CLONE: PT7CG (xi) SEQUENCE DESCRIPTION: SEQ ID NO:309:

GGACTTCTTG AATAACCCGT TC  22

(2) INFORMATION FOR SEQ ID NO:310:

(i) SEQUENCE CHARACTERISTICS:
    (A) LENGTH: 22 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Staphylococcus aureus (vii) IMMEDIATE SOURCE:
    (B) CLONE: STATOXA (xi) SEQUENCE DESCRIPTION: SEQ ID NO:310:

GGCAACTTTG ACTAACCCTC GA  22

(2) INFORMATION FOR SEQ ID NO:311:

(i) SEQUENCE CHARACTERISTICS:
    (A) LENGTH: 22 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Pneumocystis carinii (vii) IMMEDIATE SOURCE:
    (B) CLONE: PMC16SRR1

(xi) SEQUENCE DESCRIPTION: SEQ ID NO:311:

GTGGTGGTGC ATGGCCGTTC TT  22

(2) INFORMATION FOR SEQ ID NO:312:

(i) SEQUENCE CHARACTERISTICS:
    (A) LENGTH: 22 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Cryptococcus neoformans (vii) IMMEDIATE SOURCE:
    (B) CLONE: CPCDA ( x i ) SEQUENCE DESCRIPTION: SEQ ID NO:312:

GTGGTCCTGT ATGCTCTTTA CT 22

( 2 ) INFORMATION FOR SEQ ID NO:313:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Coccidiodes immitis ( v i i ) IMMEDIATE SOURCE:
        ( B ) CLONE: COIDA ( x i ) SEQUENCE DESCRIPTION: SEQ ID NO:313:

CTGGTCCGGC CGGACCTTTC CT 22

( 2 ) INFORMATION FOR SEQ ID NO:314:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Blastomyces dermatitidis ( v i i ) IMMEDIATE SOURCE:
        ( B ) CLONE: BLODA ( x i ) SEQUENCE DESCRIPTION: SEQ ID NO:314:

CTGGTCCGGC TGGACCTTTC CT 22

( 2 ) INFORMATION FOR SEQ ID NO:315:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:315:

CTGCCCTTTG TACACACCGC CC 22

( 2 ) INFORMATION FOR SEQ ID NO:316:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:316:

CAGGTCTGTG ATGCCCTTAG AT        22

( 2 ) INFORMATION FOR SEQ ID NO:317:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:317:

CAGGTCTGTG ATGCCCTTAG AT        22

( 2 ) INFORMATION FOR SEQ ID NO:318:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida albicans ( v i i ) IMMEDIATE SOURCE:
        ( B ) CLONE: YSASRSUA ( x i ) SEQUENCE DESCRIPTION: SEQ ID NO:318:

GTGGTGGTGC ATGGCCGTTC TT        22

( 2 ) INFORMATION FOR SEQ ID NO:319:

( i ) SEQUENCE CHARACTERISTICS:
        ( A ) LENGTH: 22 bases
        ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candidi albicans (vii) IMMEDIATE SOURCE:
(B) CLONE: YSAL16S (xi) SEQUENCE DESCRIPTION: SEQ ID NO:319:

GTGGTGGTGC ATGGCCGTTC TT 22

(2) INFORMATION FOR SEQ ID NO:320:

(i) SEQUENCE CHARACTERISTICS:
(A) LENGTH: 22 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida lusitaniae (vii) IMMEDIATE SOURCE:
(B) CLONE: YSASRRNAA (xi) SEQUENCE DESCRIPTION: SEQ ID NO:320:

GTGGTGGTGC ATGGCCGTTC TT 22

(2) INFORMATION FOR SEQ ID NO:321:

(i) SEQUENCE CHARACTERISTICS:
(A) LENGTH: 22 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida lusitaniae (vii) IMMEDIATE SOURCE:
(B) CLONE: YSASRSUE (xi) SEQUENCE DESCRIPTION: SEQ ID NO:321:

CAGGTCTGTG ATGCCCTTAG AC 22

(2) INFORMATION FOR SEQ ID NO:322:

(i) SEQUENCE CHARACTERISTICS:
(A) LENGTH: 22 bases
(B) TYPE: nucleic acid
(C) STRANDEDNESS: single
(D) TOPOLOGY: linear (ii) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida kefyr ( v i i ) IMMEDIATE SOURCE:
    ( B ) CLONE: YSASRSUB ( x i ) SEQUENCE DESCRIPTION: SEQ ID NO:322:

GTGGNNGTGC ATGGCCGTTC TT    22

( 2 ) INFORMATION FOR SEQ ID NO:323:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:323:

GTGGTGGTGC ATGGCCGTTT TT    22

( 2 ) INFORMATION FOR SEQ ID NO:324:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:324:

CAGGTCTGTG ATGCCCTTAG AC    22

( 2 ) INFORMATION FOR SEQ ID NO:325:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida tropicalis (vii) IMMEDIATE SOURCE:
(B) CLONE: YSASRRNAB (xi) SEQUENCE DESCRIPTION: SEQ ID NO:325:

GTGGTGGTGC ATGGCCGTTC TT    22

(2) INFORMATION FOR SEQ ID NO:326:

(i) SEQUENCE CHARACTERISTICS:
(A) LENGTH: 22 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida tropicalis (vii) IMMEDIATE SOURCE:
(B) CLONE: YSASRSUG (xi) SEQUENCE DESCRIPTION: SEQ ID NO:326:

GTGGTNGTGC ATGGCCGTTC TT    22

(2) INFORMATION FOR SEQ ID NO:327:

(i) SEQUENCE CHARACTERISTICS:
(A) LENGTH: 22 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida viswanathii (vii) IMMEDIATE SOURCE:
(B) CLONE: YSASRSUH (xi) SEQUENCE DESCRIPTION: SEQ ID NO:327:

GTGGTGGTGC ATGGCCGTTC TT    22

(2) INFORMATION FOR SEQ ID NO:328:

(i) SEQUENCE CHARACTERISTICS:
(A) LENGTH: 22 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida parapsilosis (vii) IMMEDIATE SOURCE:
(B) CLONE: YSASRSUF ( x i ) SEQUENCE DESCRIPTION: SEQ ID NO:328:

GTGGTNGTGC ATGGCCGTTC TT 22

( 2 ) INFORMATION FOR SEQ ID NO:329:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida guilliermondii ( v i i ) IMMEDIATE SOURCE:
        ( B ) CLONE: YSASRSUC ( x i ) SEQUENCE DESCRIPTION: SEQ ID NO:329:

TAAAAAATCA ATGCTCTTTG AG 22

( 2 ) INFORMATION FOR SEQ ID NO:330:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:330:

GTGGTGGTGC ATGGCCGTTC TT 22

( 2 ) INFORMATION FOR SEQ ID NO:331:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Rat alpha tropomyosin ( v i i ) IMMEDIATE SOURCE:
        ( B ) CLONE: RATTMA3

( x i ) SEQUENCE DESCRIPTION: SEQ ID NO:331:

TTGGTCCTTT ATGCTCTTCG TT 22

( 2 ) INFORMATION FOR SEQ ID NO:332:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Human ribonucl/angio ( v i i ) IMMEDIATE SOURCE:
        ( B ) CLONE: HUMRAJ ( x i ) SEQUENCE DESCRIPTION: SEQ ID NO:332:

CTGGTCCTGT ACGACATTTA CT        22

( 2 ) INFORMATION FOR SEQ ID NO:333:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Human ribonucl/angio inh ( v i i ) IMMEDIATE SOURCE:
        ( B ) CLONE: HUMRAI ( x i ) SEQUENCE DESCRIPTION: SEQ ID NO:333:

CTGGTCCTGT ACGACATTTA CT        22

( 2 ) INFORMATION FOR SEQ ID NO:334:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Pneumocystis carinii ( v i i ) IMMEDIATE SOURCE:
        ( B ) CLONE: PMC16SRR1

( x i ) SEQUENCE DESCRIPTION: SEQ ID NO:334:

TTCTTGATTC TATGGGTGGT        20

( 2 ) INFORMATION FOR SEQ ID NO:335:

( i ) SEQUENCE CHARACTERISTICS:
        ( A ) LENGTH: 20 bases
        ( B ) TYPE: nucleic acid ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
         ( A ) ORGANISM: Cryptococcus neoformans ( v i i ) IMMEDIATE SOURCE:
         ( B ) CLONE: CPCDA ( x i ) SEQUENCE DESCRIPTION: SEQ ID NO:335:

CACGTCAATC TCTGACTGGG                                                          20

( 2 ) INFORMATION FOR SEQ ID NO:336:

( i ) SEQUENCE CHARACTERISTICS:
         ( A ) LENGTH: 20 bases
         ( B ) TYPE: nucleic acid
         ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
         ( A ) ORGANISM: Coccidiodes immitis ( v i i ) IMMEDIATE SOURCE:
         ( B ) CLONE: COIDA ( x i ) SEQUENCE DESCRIPTION: SEQ ID NO:336:

GGCGTCAGTA TTCGGCTGTC                                                          20

( 2 ) INFORMATION FOR SEQ ID NO:337:

( i ) SEQUENCE CHARACTERISTICS:
         ( A ) LENGTH: 20 bases
         ( B ) TYPE: nucleic acid
         ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
         ( A ) ORGANISM: Blastomyces dermatitidis ( v i i ) IMMEDIATE SOURCE:
         ( B ) CLONE: BLODA ( x i ) SEQUENCE DESCRIPTION: SEQ ID NO:337:

GGCGTCAGTA TTCGGCTGTC                                                          20

( 2 ) INFORMATION FOR SEQ ID NO:338:

( i ) SEQUENCE CHARACTERISTICS:
         ( A ) LENGTH: 20 bases
         ( B ) TYPE: nucleic acid
         ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Aspergillus fumagatus ( v i i ) IMMEDIATE SOURCE:
    ( B ) CLONE: ASNDA ( x i ) SEQUENCE DESCRIPTION: SEQ ID NO:338:

CGCGCGCTAC ACTGACAGGT     20

( 2 ) INFORMATION FOR SEQ ID NO:339:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:339:

CGCGCGCTAC ACTGACAGGT     20

( 2 ) INFORMATION FOR SEQ ID NO:340:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:340:

CGCGCGCTAC ACTGACAGGT     20

( 2 ) INFORMATION FOR SEQ ID NO:341:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Candida albicans (vii) IMMEDIATE SOURCE:
(B) CLONE: YSASRSUA (xi) SEQUENCE DESCRIPTION: SEQ ID NO:341:

GGGGGCAACC TCATTCTGGA  20

(2) INFORMATION FOR SEQ ID NO:342:

(i) SEQUENCE CHARACTERISTICS:
(A) LENGTH: 20 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candidi albicans (vii) IMMEDIATE SOURCE:
(B) CLONE: YSAL16S (xi) SEQUENCE DESCRIPTION: SEQ ID NO:342:

CATTCAAATT TCTGCCCTAT  20

(2) INFORMATION FOR SEQ ID NO:343:

(i) SEQUENCE CHARACTERISTICS:
(A) LENGTH: 20 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida lusitaniae (vii) IMMEDIATE SOURCE:
(B) CLONE: YSASRRNAA (xi) SEQUENCE DESCRIPTION: SEQ ID NO:343:

CATTCAAATT TCTGCCCTAT  20

(2) INFORMATION FOR SEQ ID NO:344:

(i) SEQUENCE CHARACTERISTICS:
(A) LENGTH: 20 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida lusitaniae (vii) IMMEDIATE SOURCE:
(B) CLONE: YSASRSUE ( x i ) SEQUENCE DESCRIPTION: SEQ ID NO:344:

CATTCAAATT TCTGCCCTAT 20

( 2 ) INFORMATION FOR SEQ ID NO:345:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida kefyr ( v i i ) IMMEDIATE SOURCE:
        ( B ) CLONE: YSASRSUB ( x i ) SEQUENCE DESCRIPTION: SEQ ID NO:345:

AAAATCAATG TCTTCGGACT 20

( 2 ) INFORMATION FOR SEQ ID NO:346:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRRNAC ( x i ) SEQUENCE DESCRIPTION: SEQ ID NO:346:

TGCGTAAAGC CCCGACTTCT 20

( 2 ) INFORMATION FOR SEQ ID NO:347:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida krusei ( v i i ) IMMEDIATE SOURCE:
        ( B ) CLONE: YSASRSUD ( x i ) SEQUENCE DESCRIPTION: SEQ ID NO:347:

CTCGTGAAAC TCCGTCGTGC 20

( 2 ) INFORMATION FOR SEQ ID NO:348:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRRNAB ( x i ) SEQUENCE DESCRIPTION: SEQ ID NO:348:

AAAATCAATG TCTTCGGACT 20

( 2 ) INFORMATION FOR SEQ ID NO:349:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida tropicalis ( v i i ) IMMEDIATE SOURCE:
        ( B ) CLONE: YSASRSUG ( x i ) SEQUENCE DESCRIPTION: SEQ ID NO:349:

CTNGTCAAAC TTGGNCATTT 20

( 2 ) INFORMATION FOR SEQ ID NO:350:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida viswanathii ( v i i ) IMMEDIATE SOURCE:
        ( B ) CLONE: YSASRSUH ( x i ) SEQUENCE DESCRIPTION: SEQ ID NO:350:

AAAGTCNNNG GGNNCNNGGT 20

( 2 ) INFORMATION FOR SEQ ID NO:351:

( i ) SEQUENCE CHARACTERISTICS:
        ( A ) LENGTH: 20 bases
        ( B ) TYPE: nucleic acid ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
         ( A ) ORGANISM: Candida parapsilosis ( v i i ) IMMEDIATE SOURCE:
         ( B ) CLONE: YSASRSUF ( x i ) SEQUENCE DESCRIPTION: SEQ ID NO:351:

CATTCAAATT TCTGCCCTAT 20

( 2 ) INFORMATION FOR SEQ ID NO:352:

( i ) SEQUENCE CHARACTERISTICS:
         ( A ) LENGTH: 20 bases
         ( B ) TYPE: nucleic acid
         ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
         ( A ) ORGANISM: Candida guilliermondii ( v i i ) IMMEDIATE SOURCE:
         ( B ) CLONE: YSASRSUC ( x i ) SEQUENCE DESCRIPTION: SEQ ID NO:352:

CATTCAAATT TCTGCCCTAT 20

( 2 ) INFORMATION FOR SEQ ID NO:353:

( i ) SEQUENCE CHARACTERISTICS:
         ( A ) LENGTH: 20 bases
         ( B ) TYPE: nucleic acid
         ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
         ( A ) ORGANISM: Candida glabrata ( v i i ) IMMEDIATE SOURCE:
         ( B ) CLONE: YS5CRRNAS ( x i ) SEQUENCE DESCRIPTION: SEQ ID NO:353:

GTTGTCCACT TCTTAGAGGT 20

( 2 ) INFORMATION FOR SEQ ID NO:354:

( i ) SEQUENCE CHARACTERISTICS:
         ( A ) LENGTH: 20 bases
         ( B ) TYPE: nucleic acid
         ( C ) STRANDEDNESS: single
         ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Rat alpha-1-acid gly. pro.

( v i i ) IMMEDIATE SOURCE:
    ( B ) CLONE: RATAGPA1H ( x i ) SEQUENCE DESCRIPTION: SEQ ID NO:354:

TATTACAATC TCTGACTGGT 20

( 2 ) INFORMATION FOR SEQ ID NO:355:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Rat alpha-1-acid gly(sp-daw)

( v i i ) IMMEDIATE SOURCE:
        ( B ) CLONE: RATAGPA1G ( x i ) SEQUENCE DESCRIPTION: SEQ ID NO:355:

TATTACAATC TCTGACTGGT 20

( 2 ) INFORMATION FOR SEQ ID NO:356:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: S. pneumoniae malX malM ( v i i ) IMMEDIATE SOURCE:
        ( B ) CLONE: STRMALMXP ( x i ) SEQUENCE DESCRIPTION: SEQ ID NO:356:

TAACCCAATC TATGACTGGT 20

( 2 ) INFORMATION FOR SEQ ID NO:357:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

(A) ORGANISM: Pneumocystis carinii (vii) IMMEDIATE SOURCE:
  (B) CLONE: PMC16SRR1

(xi) SEQUENCE DESCRIPTION: SEQ ID NO:357:

GAGTACAATT TAGATACCTT AACGAG 26

(2) INFORMATION FOR SEQ ID NO:358:

(i) SEQUENCE CHARACTERISTICS:
    (A) LENGTH: 26 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Cryptococcus neoformans (vii) IMMEDIATE SOURCE:
    (B) CLONE: CPCDA (xi) SEQUENCE DESCRIPTION: SEQ ID NO:358:

GAGTACAATT TAAATCCCTT AACGAG 26

(2) INFORMATION FOR SEQ ID NO:359:

(i) SEQUENCE CHARACTERISTICS:
    (A) LENGTH: 26 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Coccidiodes immitis (vii) IMMEDIATE SOURCE:
    (B) CLONE: COIDA (xi) SEQUENCE DESCRIPTION: SEQ ID NO:359:

GAGTACAATT TAAATCCCTT AACGAG 26

(2) INFORMATION FOR SEQ ID NO:360:

(i) SEQUENCE CHARACTERISTICS:
    (A) LENGTH: 26 bases
    (B) TYPE: nucleic acid
    (C) STRANDEDNESS: single
    (D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Blastomyces dermatitidis (vii) IMMEDIATE SOURCE:
    (B) CLONE: BLODA ( x i ) SEQUENCE DESCRIPTION: SEQ ID NO:360:

GAGTACAATC TAAATCCCTT AACGAG 26

( 2 ) INFORMATION FOR SEQ ID NO:361:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumagatus ( v i i ) IMMEDIATE SOURCE:
        ( B ) CLONE: ASNDA ( x i ) SEQUENCE DESCRIPTION: SEQ ID NO:361:

GAGTACAATC TAAATCCCTT AACGAG 26

( 2 ) INFORMATION FOR SEQ ID NO:362:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRR5SS ( x i ) SEQUENCE DESCRIPTION: SEQ ID NO:362:

GAGTACAATC TAAATCCCTT AACGAG 26

( 2 ) INFORMATION FOR SEQ ID NO:363:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Aspergillus fumigatus ( v i i ) IMMEDIATE SOURCE:
        ( B ) CLONE: ASNRRSSB ( x i ) SEQUENCE DESCRIPTION: SEQ ID NO:363:

GAGTACAATC TAAATCCCTT AACGAG 26

( 2 ) INFORMATION FOR SEQ ID NO:364:

( i ) SEQUENCE CHARACTERISTICS:
    ( A ) LENGTH: 26 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida albicans ( v i i ) IMMEDIATE SOURCE:
    ( B ) CLONE: YSASRSUA ( x i ) SEQUENCE DESCRIPTION: SEQ ID NO:364:

GAGTACAATG TAAATACCTT AACGAG                 26

( 2 ) INFORMATION FOR SEQ ID NO:365:

( i ) SEQUENCE CHARACTERISTICS:
    ( A ) LENGTH: 26 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candidi albicans ( v i i ) IMMEDIATE SOURCE:
    ( B ) CLONE: YSAL16S ( x i ) SEQUENCE DESCRIPTION: SEQ ID NO:365:

GAGTACAATG TAAATACCTT AACGAG                 26

( 2 ) INFORMATION FOR SEQ ID NO:366:

( i ) SEQUENCE CHARACTERISTICS:
    ( A ) LENGTH: 26 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida lusitaniae ( v i i ) IMMEDIATE SOURCE:
    ( B ) CLONE: YSASRRNAA ( x i ) SEQUENCE DESCRIPTION: SEQ ID NO:366:

GAGTACAATG TAAATACCTT AACGAG                 26

( 2 ) INFORMATION FOR SEQ ID NO:367:

( i ) SEQUENCE CHARACTERISTICS:
    ( A ) LENGTH: 26 bases
    ( B ) TYPE: nucleic acid (C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
    (A) ORGANISM: Candida lusitaniae (vii) IMMEDIATE SOURCE:
    (B) CLONE: YSASRSUE (xi) SEQUENCE DESCRIPTION: SEQ ID NO:367:

GAGTACAATG TAAATACCTT AACGAG     26

(2) INFORMATION FOR SEQ ID NO:368:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida kefyr (vii) IMMEDIATE SOURCE:
        (B) CLONE: YSASRSUB (xi) SEQUENCE DESCRIPTION: SEQ ID NO:368:

GAGTACAATG TAAATACCTT AACGAG     26

(2) INFORMATION FOR SEQ ID NO:369:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: cDNA to rRNA (iii) HYPOTHETICAL: NO (iv) ANTI-SENSE: NO (vi) ORIGINAL SOURCE:
        (A) ORGANISM: Candida krusei (vii) IMMEDIATE SOURCE:
        (B) CLONE: YSASRRNAC (xi) SEQUENCE DESCRIPTION: SEQ ID NO:369:

GAGTACAATG TAAATACCTT AACGAG     26

(2) INFORMATION FOR SEQ ID NO:370:

(i) SEQUENCE CHARACTERISTICS:
        (A) LENGTH: 26 bases
        (B) TYPE: nucleic acid
        (C) STRANDEDNESS: single
        (D) TOPOLOGY: linear (ii) MOLECULE TYPE: cDNA to rRNA (i i i) HYPOTHETICAL: NO (i v) ANTI-SENSE: NO (v i) ORIGINAL SOURCE:
    (A) ORGANISM: Candida krusei (v i i) IMMEDIATE SOURCE:
    (B) CLONE: YSASRSUD (x i) SEQUENCE DESCRIPTION: SEQ ID NO:370:

GAGTACAATG TAAATACCTT AACGAG      26

(2) INFORMATION FOR SEQ ID NO:371:

(i) SEQUENCE CHARACTERISTICS:
        (A) LENGTH: 26 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida tropicalis (v i i) IMMEDIATE SOURCE:
        (B) CLONE: YSASRRNAB (x i) SEQUENCE DESCRIPTION: SEQ ID NO:371:

GAGTACAATG TAAATACCTT AACGAG      26

(2) INFORMATION FOR SEQ ID NO:372:

(i) SEQUENCE CHARACTERISTICS:
        (A) LENGTH: 26 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Candida tropicalis (v i i) IMMEDIATE SOURCE:
        (B) CLONE: YSASRSUG (x i) SEQUENCE DESCRIPTION: SEQ ID NO:372:

GAGTACAATG TAAATACCTT AACGAG      26

(2) INFORMATION FOR SEQ ID NO:373:

(i) SEQUENCE CHARACTERISTICS:
        (A) LENGTH: 26 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:

(A) ORGANISM: Candida viswanathii (vii) IMMEDIATE SOURCE:
   (B) CLONE: YSASRSUH (xi) SEQUENCE DESCRIPTION: SEQ ID NO:373:

GAGTACAATG TAAATACCTT AACGAG                                    26

(2) INFORMATION FOR SEQ ID NO:374:

(i) SEQUENCE CHARACTERISTICS:
      (A) LENGTH: 26 bases
      (B) TYPE: nucleic acid
      (C) STRANDEDNESS: single
      (D) TOPOLOGY: linear (ii) MOLECULE TYPE: cDNA to rRNA (iii) HYPOTHETICAL: NO (iv) ANTI-SENSE: NO (vi) ORIGINAL SOURCE:
      (A) ORGANISM: Candida parapsilosis (vii) IMMEDIATE SOURCE:
      (B) CLONE: YSASRSUF (xi) SEQUENCE DESCRIPTION: SEQ ID NO:374:

GAGTACAATG TAAATACCTT AACGAG                                    26

(2) INFORMATION FOR SEQ ID NO:375:

(i) SEQUENCE CHARACTERISTICS:
      (A) LENGTH: 26 bases
      (B) TYPE: nucleic acid
      (C) STRANDEDNESS: single
      (D) TOPOLOGY: linear (ii) MOLECULE TYPE: cDNA to rRNA (iii) HYPOTHETICAL: NO (iv) ANTI-SENSE: NO (vi) ORIGINAL SOURCE:
      (A) ORGANISM: Candida guilliermondii (vii) IMMEDIATE SOURCE:
      (B) CLONE: YSASRSUC (xi) SEQUENCE DESCRIPTION: SEQ ID NO:375:

GAGTACAATG TAAATACCTT AACGAG                                    26

(2) INFORMATION FOR SEQ ID NO:376:

(i) SEQUENCE CHARACTERISTICS:
      (A) LENGTH: 26 bases
      (B) TYPE: nucleic acid
      (C) STRANDEDNESS: single
      (D) TOPOLOGY: linear (ii) MOLECULE TYPE: cDNA to rRNA (iii) HYPOTHETICAL: NO (iv) ANTI-SENSE: NO (vi) ORIGINAL SOURCE:
      (A) ORGANISM: Candida glabrata (vii) IMMEDIATE SOURCE:
      (B) CLONE: YS5CRRNAS ( x i ) SEQUENCE DESCRIPTION: SEQ ID NO:376:

GAGTACAATG TAAATACCTT AACGAG                                                                    26

( 2 ) INFORMATION FOR SEQ ID NO:377:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Yeast 18s RNA ( v i i ) IMMEDIATE SOURCE:
        ( B ) CLONE: YSCRNA5

( x i ) SEQUENCE DESCRIPTION: SEQ ID NO:377:

GAGTACAATG TAAATACCTT AACGAG                                                                    26

( 2 ) INFORMATION FOR SEQ ID NO:378:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Yeast (S. cerevisiae)

( v i i ) IMMEDIATE SOURCE:
        ( B ) CLONE: TSCRGEA ( x i ) SEQUENCE DESCRIPTION: SEQ ID NO:378:

GAGTACAATG TAAATACCTT AACGAG                                                                    26

( 2 ) INFORMATION FOR SEQ ID NO:379:

( i ) SEQUENCE CHARACTERISTICS:
        ( A ) LENGTH: 26 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Kluyveromyces lactis ( v i i ) IMMEDIATE SOURCE:
        ( B ) CLONE: YSK17SRRNA ( x i ) SEQUENCE DESCRIPTION: SEQ ID NO:379:

GAGTACAATG TAAATACCTT AACGAG                                                                    26

( 2 ) INFORMATION FOR SEQ ID NO:380:

( i ) SEQUENCE CHARACTERISTICS:
       ( A ) LENGTH: 26 bases
       ( B ) TYPE: nucleic acid
       ( C ) STRANDEDNESS: single
       ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE: Torulaspora delbrueckii
       ( A ) ORGANISM:

( v i i ) IMMEDIATE SOURCE:
       ( B ) CLONE: TOUSRSR ( x i ) SEQUENCE DESCRIPTION: SEQ ID NO:380:

GAGTACAATG TAAATACCTT AACGAG    26

( 2 ) INFORMATION FOR SEQ ID NO:381:

( i ) SEQUENCE CHARACTERISTICS:
       ( A ) LENGTH: 26 bases
       ( B ) TYPE: nucleic acid
       ( C ) STRANDEDNESS: single
       ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
       ( A ) ORGANISM: T. glabrata rRNA ( v i i ) IMMEDIATE SOURCE:
       ( B ) CLONE: YSLSRSUA ( x i ) SEQUENCE DESCRIPTION: SEQ ID NO:381:

GAGTACAATG TAAATACCTT AACGAG    26

( 2 ) INFORMATION FOR SEQ ID NO:382:

( i ) SEQUENCE CHARACTERISTICS:
       ( A ) LENGTH: 26 bases
       ( B ) TYPE: nucleic acid
       ( C ) STRANDEDNESS: single
       ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
       ( A ) ORGANISM: H. polymorpha rRNA ( v i i ) IMMEDIATE SOURCE:
       ( B ) CLONE: HASSRSUA ( x i ) SEQUENCE DESCRIPTION: SEQ ID NO:382:

GAGTACAATG TAAATACCTT AACGAG    26

( 2 ) INFORMATION FOR SEQ ID NO:383:

( i ) SEQUENCE CHARACTERISTICS:
       ( A ) LENGTH: 26 bases
       ( B ) TYPE: nucleic acid ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: S. pombe rRNA ( v i i ) IMMEDIATE SOURCE:
                    ( B ) CLONE: YSPRRNASS ( x i ) SEQUENCE DESCRIPTION: SEQ ID NO:383:

GAGTACAATG TAAATACCTT AACGAG 26

( 2 ) INFORMATION FOR SEQ ID NO:384:

( i ) SEQUENCE CHARACTERISTICS:
                    ( A ) LENGTH: 21 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Pneumocystis carinii ( v i i ) IMMEDIATE SOURCE:
                    ( B ) CLONE: PMC16SRR1

( x i ) SEQUENCE DESCRIPTION: SEQ ID NO:384:

TTAAGCCATG CATGTCTAAG T 21

( 2 ) INFORMATION FOR SEQ ID NO:385:

( i ) SEQUENCE CHARACTERISTICS:
                    ( A ) LENGTH: 21 bases
                    ( B ) TYPE: nucleic acid
                    ( C ) STRANDEDNESS: single
                    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
                    ( A ) ORGANISM: Cryptococcus neoformans ( v i i ) IMMEDIATE SOURCE:
                    ( B ) CLONE: CPCDA ( x i ) SEQUENCE DESCRIPTION: SEQ ID NO:385:

TTCGGCCCTC TATGGTGAAT C 21

( 2 ) INFORMATION FOR SEQ ID NO:386:

( i ) SEQUENCE CHARACTERISTICS:
                    ( A ) LENGTH: 21 bases
                    ( B ) TYPE: nucleic acid
                    ( C ) STRANDEDNESS: single
                    ( D ) TOPOLOGY: linear ( i i ) MOLECULE TYPE: cDNA to rRNA (i i i) HYPOTHETICAL: NO (i v) ANTI-SENSE: NO (v i) ORIGINAL SOURCE:
    (A) ORGANISM: Coccidiodes immitis (v i i) IMMEDIATE SOURCE:
    (B) CLONE: COIDA (x i) SEQUENCE DESCRIPTION: SEQ ID NO:386:

TTAAGCCATG CATGTCTAAG T     21

(2) INFORMATION FOR SEQ ID NO:387:

(i) SEQUENCE CHARACTERISTICS:
        (A) LENGTH: 21 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Blastomyces dermatitidis (v i i) IMMEDIATE SOURCE:
        (B) CLONE: BLODA (x i) SEQUENCE DESCRIPTION: SEQ ID NO:387:

TTAAGCCATG CATGTCTAAG T     21

(2) INFORMATION FOR SEQ ID NO:388:

(i) SEQUENCE CHARACTERISTICS:
        (A) LENGTH: 21 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:
        (A) ORGANISM: Aspergillus fumagatus (v i i) IMMEDIATE SOURCE:
        (B) CLONE: ASNDA (x i) SEQUENCE DESCRIPTION: SEQ ID NO:388:

ATAAGCAATT TATACGGTGA A     21

(2) INFORMATION FOR SEQ ID NO:389:

(i) SEQUENCE CHARACTERISTICS:
        (A) LENGTH: 21 bases
        (B) TYPE: nucleic acid
        (C) STRANDEDNESS: single
        (D) TOPOLOGY: linear (i i) MOLECULE TYPE: cDNA to rRNA (i i i) HYPOTHETICAL: NO (i v) ANTI-SENSE: NO (v i) ORIGINAL SOURCE:

(A) ORGANISM: Aspergillus fumigatus (vii) IMMEDIATE SOURCE:
(B) CLONE: ASNRR5SS (xi) SEQUENCE DESCRIPTION: SEQ ID NO:389:

ATAAGCAATT TATACGGTGA A 21

(2) INFORMATION FOR SEQ ID NO:390:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Aspergillus fumigatus (vii) IMMEDIATE SOURCE:
(B) CLONE: ASNRRSSB (xi) SEQUENCE DESCRIPTION: SEQ ID NO:390:

ATAAGCAATT TATACGGTGA A 21

(2) INFORMATION FOR SEQ ID NO:391:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candida albicans (vii) IMMEDIATE SOURCE:
(B) CLONE: YSASRSUA (xi) SEQUENCE DESCRIPTION: SEQ ID NO:391:

GGTAGCCATT TATGGCGAAC C 21

(2) INFORMATION FOR SEQ ID NO:392:

(i) SEQUENCE CHARACTERISTICS:
(A) LENGTH: 21 bases
(B) TYPE: nucleic acid
(C) STRANDEDNESS: single
(D) TOPOLOGY: linear (ii) MOLECULE TYPE: cDNA to rRNA (iii) HYPOTHETICAL: NO (iv) ANTI-SENSE: NO (vi) ORIGINAL SOURCE:
(A) ORGANISM: Candidi albicans (vii) IMMEDIATE SOURCE:
(B) CLONE: YSAL16S ( x i ) SEQUENCE DESCRIPTION: SEQ ID NO:392:

GGTAGCCATT TATGGCGAAC C                                                       21

( 2 ) INFORMATION FOR SEQ ID NO:393:

( i ) SEQUENCE CHARACTERISTICS:
          ( A ) LENGTH: 21 bases
          ( B ) TYPE: nucleic acid
          ( C ) STRANDEDNESS: single
          ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
          ( A ) ORGANISM: Candida lusitaniae ( v i i ) IMMEDIATE SOURCE:
          ( B ) CLONE: YSASRRNAA ( x i ) SEQUENCE DESCRIPTION: SEQ ID NO:393:

TTAAGCCATG CATGTCTAAG T                                                       21

( 2 ) INFORMATION FOR SEQ ID NO:394:

( i ) SEQUENCE CHARACTERISTICS:
          ( A ) LENGTH: 21 bases
          ( B ) TYPE: nucleic acid
          ( C ) STRANDEDNESS: single
          ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
          ( A ) ORGANISM: Candida lusitaniae ( v i i ) IMMEDIATE SOURCE:
          ( B ) CLONE: YSASRSUE ( x i ) SEQUENCE DESCRIPTION: SEQ ID NO:394:

GCTAGCCTNG TCTGGCGCGC N                                                       21

( 2 ) INFORMATION FOR SEQ ID NO:395:

( i ) SEQUENCE CHARACTERISTICS:
          ( A ) LENGTH: 21 bases
          ( B ) TYPE: nucleic acid
          ( C ) STRANDEDNESS: single
          ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
          ( A ) ORGANISM: Candida kefyr ( v i i ) IMMEDIATE SOURCE:
          ( B ) CLONE: YSASRSUB ( x i ) SEQUENCE DESCRIPTION: SEQ ID NO:395:

GCTAGCNCTT GCTGGTTNAC T                                                       21

( 2 ) INFORMATION FOR SEQ ID NO:396:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida krusei ( v i i ) IMMEDIATE SOURCE:
    ( B ) CLONE: YSASRRNAC ( x i ) SEQUENCE DESCRIPTION: SEQ ID NO:396:

CGTTTTCATT AATCAAGAAC G         21

( 2 ) INFORMATION FOR SEQ ID NO:397:

( i ) SEQUENCE CHARACTERISTICS:
    ( A ) LENGTH: 21 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida krusei ( v i i ) IMMEDIATE SOURCE:
    ( B ) CLONE: YSASRSUD ( x i ) SEQUENCE DESCRIPTION: SEQ ID NO:397:

TTAAGCCATG CATGTCTAAG T         21

( 2 ) INFORMATION FOR SEQ ID NO:398:

( i ) SEQUENCE CHARACTERISTICS:
    ( A ) LENGTH: 19 bases
    ( B ) TYPE: nucleic acid
    ( C ) STRANDEDNESS: single
    ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida tropicalis ( v i i ) IMMEDIATE SOURCE:
    ( B ) CLONE: YSASRRNAB ( x i ) SEQUENCE DESCRIPTION: SEQ ID NO:398:

GCTAGCCTTT TGGCGAACC         19

( 2 ) INFORMATION FOR SEQ ID NO:399:

( i ) SEQUENCE CHARACTERISTICS:
    ( A ) LENGTH: 19 bases
    ( B ) TYPE: nucleic acid ( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida tropicalis ( v i i ) IMMEDIATE SOURCE:
( B ) CLONE: YSASRSUG ( x i ) SEQUENCE DESCRIPTION: SEQ ID NO:399:

GCTAGCCTTT TGGCGAACC   19

( 2 ) INFORMATION FOR SEQ ID NO:400:

( i ) SEQUENCE CHARACTERISTICS:
( A ) LENGTH: 19 bases
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida viswanathii ( v i i ) IMMEDIATE SOURCE:
( B ) CLONE: YSASRSUH ( x i ) SEQUENCE DESCRIPTION: SEQ ID NO:400:

GCTAGCCTTT TGGCGAACC   19

( 2 ) INFORMATION FOR SEQ ID NO:401:

( i ) SEQUENCE CHARACTERISTICS:
( A ) LENGTH: 20 bases
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
( A ) ORGANISM: Candida parapsilosis ( v i i ) IMMEDIATE SOURCE:
( B ) CLONE: YSASRSUF ( x i ) SEQUENCE DESCRIPTION: SEQ ID NO:401:

GCTAGCCTTT TTGGCGAACC   20

( 2 ) INFORMATION FOR SEQ ID NO:402:

( i ) SEQUENCE CHARACTERISTICS:
( A ) LENGTH: 21 bases
( B ) TYPE: nucleic acid
( C ) STRANDEDNESS: single
( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
    ( A ) ORGANISM: Candida guilliermondii ( v i i ) IMMEDIATE SOURCE:
    ( B ) CLONE: YSASRSUC ( x i ) SEQUENCE DESCRIPTION: SEQ ID NO:402:

GGTCCGCCTT TTTGGCGAGT A          21

( 2 ) INFORMATION FOR SEQ ID NO:403:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: Candida glabrata ( v i i ) IMMEDIATE SOURCE:
        ( B ) CLONE: YS5CRRNAS ( x i ) SEQUENCE DESCRIPTION: SEQ ID NO:403:

ATAAGCAATT TATACAGTGA A          21

( 2 ) INFORMATION FOR SEQ ID NO:404:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
        ( A ) ORGANISM: S. enterica ( v i i ) IMMEDIATE SOURCE:
        ( B ) CLONE: STYRFB ( x i ) SEQUENCE DESCRIPTION: SEQ ID NO:404:

GGTAGCCGTT TATGGCCGCT T          21

( 2 ) INFORMATION FOR SEQ ID NO:405:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:

( A ) ORGANISM: Cloistridium pastcurianum ( v i i ) IMMEDIATE SOURCE:
          ( B ) CLONE: CLONIFH5

( x i ) SEQUENCE DESCRIPTION: SEQ ID NO:405:

GGTAGCTATT TATGGAAAAG G                                         21

( 2 ) INFORMATION FOR SEQ ID NO:406:

( i ) SEQUENCE CHARACTERISTICS:
          ( A ) LENGTH: 21 bases
          ( B ) TYPE: nucleic acid
          ( C ) STRANDEDNESS: single
          ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
          ( A ) ORGANISM: C. pasteurianum nifH ( v i i ) IMMEDIATE SOURCE:
          ( B ) CLONE: CLONIFH ( x i ) SEQUENCE DESCRIPTION: SEQ ID NO:406:

GGTAGCTATT TATGGAAAAG G                                         21

( 2 ) INFORMATION FOR SEQ ID NO:407:

( i ) SEQUENCE CHARACTERISTICS:
          ( A ) LENGTH: 21 bases
          ( B ) TYPE: nucleic acid
          ( C ) STRANDEDNESS: single
          ( D ) TOPOLOGY: linear ( i i ) MOLECULE TYPE: cDNA to rRNA ( i i i ) HYPOTHETICAL: NO ( i v ) ANTI-SENSE: NO ( v i ) ORIGINAL SOURCE:
          ( A ) ORGANISM: C. pasteurianum nifH ( v i i ) IMMEDIATE SOURCE:
          ( B ) CLONE: CLONIFH1

( x i ) SEQUENCE DESCRIPTION: SEQ ID NO:407:

GGTAGCTATT TATGGAAAAG G                                         21